US007041503B2

(12) United States Patent
Nye et al.

(10) Patent No.: US 7,041,503 B2
(45) Date of Patent: May 9, 2006

(54) MODIFIED MYELIN BASIC PROTEIN MOLECULES

(75) Inventors: Steven H. Nye, Mequon, WI (US); Michael J. Lenardo, Potomac, MD (US); Henry F. McFarland, Gaithersburg, MD (US); Louis A. Matis, Southport, CT (US); Eileen Elliott Mueller, East Haven, CT (US); John P. Mueller, East Haven, CT (US); Clara M. Pelfrey, Gaithersburg, MD (US); Stephen P. Squinto, Bethany, CT (US); James A. Wilkins, Woodbridge, CT (US)

(73) Assignees: The United States of America as represented by the Department of Health and Human Services, Washington, DC (US); Alexion Pharmaceuticals, Inc., Cheshire, CT (US)

( * ) Notice: Subject to any disclaimer, the term of this patent is extended or adjusted under 35 U.S.C. 154(b) by 565 days.

(21) Appl. No.: 08/431,644

(22) Filed: May 2, 1995

(65) Prior Publication Data
US 2004/0180808 A1    Sep. 16, 2004

(51) Int. Cl.
*C12N 5/00*    (2006.01)
*C12N 5/02*    (2006.01)
(52) U.S. Cl. ..................... 435/375; 435/377; 435/7.24; 435/975; 530/300; 530/324; 530/350
(58) Field of Classification Search ................ 530/300, 530/350, 324, 325, 326, 327, 839; 514/2, 514/12; 435/975, 325, 372.3, 7.24, 375, 435/377; 436/63, 506, 8, 15, 86
See application file for complete search history.

(56) References Cited

U.S. PATENT DOCUMENTS

| | | | |
|---|---|---|---|
| 4,853,332 A | 8/1989 | Mark et al. | |
| 5,871,997 A | 2/1999 | Rother et al. | |
| 5,935,575 A | 8/1999 | Lenardo et al. | |
| 5,989,546 A | 11/1999 | Lenardo | |
| 6,039,947 A | * 3/2000 | Weiner et al. | ........... 424/184.1 |
| 6,083,503 A | 7/2000 | Lenardo | |
| 6,083,504 A | 7/2000 | Cotropia | |

FOREIGN PATENT DOCUMENTS

| | | |
|---|---|---|
| WO | WO 94/03202 A1 | 2/1994 |
| WO | WO 94/28926 A1 | 12/1994 |
| WO | WO 96/34622 A1 | 11/1996 |

OTHER PUBLICATIONS

Voskhul et al, J. Immunology, 153(10):4834-4844, 1994.*
Voskhul et al, J. Neuroimmurdl 46(1-2):137-144, 1993.*
Kamholz et al, Proc. Natl. Acad-Sci USA, 83: 4962-4966, 1987.*
Pareyra et al., Nerochemical Research 13(6): 583-595, 1988.*
Raines et al, Handbook of Clinical Neurology 3(47): 429-466, 1985),*
Alvord et al, Annals Neurology, 6(6): 461-468, 1978.*
Traugott et al, J. Neurosciences, 56: 65-73, 1982).*
Weiner et al, Science 259: 1263, 1993.*
Bielokova et al (Nature Medicine 6(10): 1167-1175, Oct. 2000).*
Popot et. al. Major Myelin Proteolipid: The 4-Alpha Helix Toplogy J. Membrane Biol. 120, 223-246 (1991).
Weimbs et al. A Point Mutation at the X-Chromosomal Proteolipid Protein Locus in Pelzaeus- Merzbacher Disease Leads to Disruption of Myelinogenesis Biol. Chem. Hoppe-Seyler. vol. 371, pp. 1175-1183, Dec. 1990.
Hudson L D et al: Mutation of the Proteolipid Protein Gene PLP in a human X Chromosome- Linked Myelin Disorder Proc. Natl. Acad. Sci. USA. vol. 86, pp. 8128-8131, No. 20 Oct. 1989.
Simons R et al: Single Base Substitution in Condon 74 of the MD Rat Myelin Proteolipid Protein Gene. Annals of the New York Academy of Sciences, New Yo NY. U.S., vol. 605, 1990. pp. 146-154.
Simons R et al: The Myelin- Deficient Rat has a Single Base Substitution in the Third exon of the Myelin Proteolipid Protein Gene Journal of Neurochemistry, New York N.Y. US, vol. 54, No. 3, Mar. 1990 pp. 1079-1081.
Tsuchida T. et al: Autoreactive CD8+T−Cell Responses to Human Myelin Protein Derived Peptides. Proceeding of the National Academy of Science U.S.A. Washington, US. vol. 91, No. 23, Nov. 1994 pp. 10859-10863.
Nye et al. Purification of Immunologically Active Recombinant 21.5 kDa Isofor of Human Myelin Basic Protein. Molecular Immunology, vol. 32, No. 14/15 pp. 1131-1141.
Zhao et al. The immune response to a subdominant epitode in myelin basic protein exon-2 results in immunity to intra- and intermolecular dominant epitopes. Journal of Neuroimmunology 61 pp. 179-184 (1995).

(Continued)

Primary Examiner—Patricia A. Duffy
(74) Attorney, Agent, or Firm—Leydig, Voit & Mayer, Ltd.

(57) ABSTRACT

Compositions and methods are provided for the clinical assessment, diagnosis, and treatment of multiple sclerosis. The compositions of the invention are molecules related to the 21.5 kDa fetal isoform of human myelin basic protein, and include nucleic acids and polypeptides. The nucleic acid molecules of the invention are useful in the efficient production of modified and unmodified 21.5 kDa myelin basic protein polypeptides, such polypeptides being useful for assaying T cells for responsiveness to myelin basic protein epitopes. The polypeptides of the invention are also useful as therapeutic agents that act by inducing T cell responses, including apoptosis, as a means of treating multiple sclerosis.

19 Claims, 13 Drawing Sheets

OTHER PUBLICATIONS

Activation of a myelin basic protein-specific human T cell clone by antigen-presenting cells from rhesus monkey. Meinl et al. International Immunology, vol. 7, No. 9, pp. 1489-1495.

Identification of a cDNA coding for a fifth form of myelin basic protein in mouse. Newman et al. Proc. Natl. Acad. Sci. USA vol. 84, pp. 886-890, Feb. 1987 Neurobiology.

Evidence for the Expression of Four Myelin Basic Protein Variants in the Developing Human Spinal Cord Through cDNA Cloning. Roth et al. Journal of Neuroscience Research 17:321-328 (1987).

Identification of three forms of human myelin basic protein by cDNA cloning. Kamholz et al. Proc. Natl. Acad. Sci. USA vol. 83, pp. 4962-4966, Jul. 1986 Neurobiology.

H.L. Weiner et al.: Double-Blind Pilot Trial of Oral tolerization with Myeli Antigens in Multiple sclerosis Science, vol. 259, Feb. 26, 1993 pp. 1321-1324.

Abbas et al., *Cell. Mol. Immunology* 2$^{nd}$ *Ed.*, Ch. 19, 377-392 (1994).
Adorini et al., *Immunol. Today*, 14(6), 285-289, (1993).
Alderson et al., *J. Exp. Med.*, 181, 71-77 (1995).
Allegretta et al., *Science*, 247, 718-721 (1990).
Boehme et al., *Eur. J. Immunol.*, 23, 1552-1560 (1993).
Bolton, *Mult. Scier.*, 1, 143-149 (1995).
Brown et al., *Lab. Invest.*, 45(3), 278-284 (1981).
Brück et al., *Ann. Neurol.*, 35, 65-73 (1994).
Burns et al., *J. Exp. Med.*, 169, 27-39 (1989).
Chou et al., *J. Neuroimmunol.*, 38, 105-114 (1992).
Chou et al., *J. Neurosci. Res.*, 23, 207-216 (1989).
Cohen et al., *Annu. Rev. Immunol.*, 10, 267-293 (1992).
Cotter et al., *Anticancer Res.*, 10, 1153-1160 (1990).
CRISPE, *Immunity*, 1, 347-349 (1994).
Critchfield et al., *Science*, 263, 1139-1143 (1994).
Deibler et al., *Prep. Biochem.*, 2(2), 139-165 (1972).
Diehl et al, *Proc. Natl. Acad. Sci. USA*, 83, 9807-9811 (1986).
Duvall et al., *Immunol. Today*, 7(4), 115-119 (1986).
Einstein et al., *J. Neurochem.*, 9, 353-361 (1962).
Elliott et a., *J. Clin. Invest.*, 98(7), 1602-1612 (1996).
Endoh et al., *J. Immunol.*, 137(12), 3832-3835 (1986).
Evans et al., *Gene*, 84, 135-142 (1989).
Fritz et al., *J. Immunol.*, 130(1), 191-194 (1983).
Fritz et al., *J. Neuroimmunol.*, 51, 1-6 (1994).
Greer et al., *J. Immunol.*, 149(3), 783-788 (1992).
Grosjean et al., *Gene*, 18, 199-209 (1982).
HAUSER, *Harrison's Principles of Int. Med. 13$^{th}$Ed.*, Ch. 373, 2287-2295 (1994).
Hernan et al., *Biochem.*, 31(36), 8619-8628 (1992).
Ho et al., *Gene*, 77, 51-59 (1989).
Huang et al., *Mol. Cell. Biol.*, 10(4), 1805-1810 (1990).
Jayaraman et al., *Proc. Natl. Acad. Sci. USA*, 88, 4084-4088 (1991).
Kalghatgi et al., *J. Chromatogr.*, 398, 335-339 (1987).
Kamholz et al., *J. Neurosci. Res.*, 21, 62-70 (1988).
Kaufman et al., *Nature*, 366, 69-72 (1993).
Kawabe et al., *Nature*, 349, 245-248 (1991).
Kennedy et al., *J. Immunol.*, 144(3), 909-915 (1990).
Kerlero De Rosbo et al., *J. Clin. Invest.*, 92, 2602-2608 (1993).
Kerr et al., *Apoptosis: The Molecular Basis of Cell Death*, 5-29 (1991).
Kronquist et al., *J. Neurosci. Res.*, 18, 395-401 (1987).
Kuchroo et al., *J. Immunol.*, 148(12), 3776-3782 (1992).
Kuchroo et al., *J. Immunol.*, 153, 3326-3336 (1994).
Lees et al., *Neuronal and Glial Proteins*, Ch. 11, 267-298 (1988).
Lehmann et al., *Nature*, 358, 155-157 (1992).
LENARDO, *Nature*, 353, 858-861 (1991).
Linthicum et al., *Cell. Immunol.*, 73, 299-310 (1982).
Lockshin et al, *Apoptosis: The Molecular Basis of Cell Death*, 47-60 (1991).
Marrack et al., *Science*, 238, 1073-1078 (1987).
Martin et al., *Annu. Rev. Immunol.*, 10, 153-187 (1992).
Martin et al., *J. Immunol.*, 145(2), 540-548 (1990).
Massacesi et al., *Ann. Neurol.*, 37(4), 519-530 (1995).
Matis et al., *Proc. Natl. Acad. Sci., USA*, 80, 6019-6023 (1983).
McCarron et al., *J. Neuroimmunol.*, 29, 73-79 (1990).
McFarland et al., *J. Immunol.*, 166, 2116-2121 (2001).
McRae et al., *J. Neuroimmunol.*, 38, 229-240 (1992).
Meinl et al., *J. Clin. Invest.*, 92, 2633-2643 (1993).
Miller et al., *Immunol. Today*, 15(8), 356-361 (1994).
Miller et al., *J. Neuroimmunol.*, 39, 243-250 (1992).
MITCHISON, *Proc. R. Soc. London Ser. B*, 161, 275-292 (1964).
Morgenstern et al., *Nucl. Acids Res.*, 18(12), 3587-3596 (1990).
Oettinger et al., *J. Neuroimmunol.*, 44, 157-162 (1993).
Ota et al., *Nature*, 346, 183-187 (1990).
Pelfrey et al., *J. Neuroimmunol.*, 46, 33-42 (1993).
Pelfrey et al., *J. Neuroimmunol.*, 53, 153-161 (1994).
Pette et al., *Neurology*, 40, 1770-1776 (1990).
Prineas et al., *Ann. Neurol.*, 33, 137-151 (1993).
Raine et al., *J. Neuropathol. Exp. Neurol.*, 52(3), 199-204 (1993).
Ransohoff et al., *Curr. Opin. Neurol.*, 7, 242-249 (1994).
Richert et al., *J. Neuroimmunol.*, 23, 55-66 (1989).
Russell et al., *Proc. Natl. Acad. Sci., USA*, 90, 4409-4413 (1993).
Saeki et al., *Proc. Natl. Acad. Sci., USA*, 89, 6157-6161 (1992).
Sakai et al., *Proc. Natl. Acad. Sci., USA*, 86, 9470-9474 (1989).
Sato et al., *J. Biol. Chem.*, 269(25), 17267-17273 (1994).
Schwartz et al., *Fundamental Immunology*, 3$^{rd}$ Ed., Ch. 30, 1033-1097 (1993).
Segal et al., *J. Neuromimmunol.*, 51, 7-19 (1994).
Sercarz et al., *Nature*, 184, 1080-1082 (1959).
Singer et al., *Immunity*, 1, 365-371 (1994).
Smith et al., *Nature*, 337, 181-184 (1989).
Sobel et al., *J. Immunol.*, 149(4), 1444-1451 (1992).
Sprent, *Cell*, 76, 315-322 (1994).
Spiram et al., *Cell. Immunol.*, 75, 378-382 (1983).
Studier et al., *Meth. Enzymol.*, 185, 60-89 (1990).
Su et al., *J. Neuroimmunol.*, 34, 181-190 (1991).
Sun et al., *Eur. J. Immunol.*, 21, 1461-1468 (1991).
Tabira, *Ann. NY Acad. Sci.*, 540, 187-201 (1988).
Traugott et al, *J. Neurological Sci.*, 56, 65-73 (1982).
Trotter et al., *J. Neuroimmunol.*, 33, 55-62 (1991).
Trotter et al., *J. Neurological Sci.*, 79, 173-188 (1987).
Tuohy et al., *J. Immunol.*, 141(4), 1126-1130 (1988).
Tuohy et al., *J. Immunol.*, 142(5), 1523-1527 (1989).
Tuohy et al., *J. Neuroimmunol.*, 39, 67-74 (1992).
Van Der Veen et al., *J. Neuroimmunol.*, 21, 183-191 (1989).
Van Der Veen et al., *J. Neuroimmunol.*, 26, 139-145 (1990).
Van Der Veen et al., *J. Neuroimmunol.*, 38, 139-146 (1992).
Van Noort et al., *J. Chromatogr. B*, 653, 155-161 (1994).
Von Boehmer, *Ann. Rev. Immunol.*, 6, 309-326 (1988).
Voskhul et al., *J. Neuroimmunol.*, 42, 187-192 (1993).

Wada et al., *Nucl. Acids Res.*, 20 ( Suppl.), 2111-2118 (1992).
Wauben et al., *J. Immunol.*, 152, 4211-4220 (1994).
Weimbs et al., *Biochem.*, 31, 12289-12296 (1992).
Whitham et al., *J. Immunol.*, 146(1), 101-107 (1991).
Whitham et al., *J. Immunol.*, 147(11) 3803-3808 (1991).
Williams et al., *Nucl. Acids. Res.*, 16(22), 10453-10467 (1988).
Wosnick et al., *Gene*, 60, 115-127 (1987).
Yoon, *Science*, 259, 1263 (1993).
Zamvil et al., *Nature*, 324, 258-260 (1986).
Zhang et al., *J. Exp. Med.*, 179, 973-984 (1994).
Zhang et al., *Science*, 261, 1451-1454 (1993).
Abo et al., *Bio. Molec. Biol. Int.*, 30(5), 945-958 (1993).
Allegretta et al., *J. Clin. Invest.*, 94, 105-109 (1994).
Alvord et al., *Ann. Neurol.*, 6, 469-473 (1979).
Alvord et al., *Prog. Clin. Biol. Res.*, 146, 359-363 (1984).
Ammerer, *Meth. Enzymol.*, 101, 192-201 (1983).
Amor et al., *J. Immunol.*, 153, 4349-4356 (1994).
Aruga et al., *J. Neurochem.*, 56, 1222-1226 (1991).
Barnett et al., *J. Neuroimmunol.*, 44, 15-26 (1993).
Bishopp, *Bioworld Today*, 8 (77), (1997).
Brunner et al., *Nature*, 373, 441-444 (1995).
Carnegie et al., *Biochem. J.*, 123, 57-67 (1971).
Chang et al., *Nature*, 275, 617-624 (1978).
Chen et al., *Science*, 265, 1237-1240 (1994).
Chiang et al., *Int. Arch. Allery Immunol.*, 98, 181-188 (1992).
Chou et al., *J. Neurosci. Res.*, 28, 280-290 (1991).
Correale et al., *J. Immunol.*, 154, 2959-2968 (1995).
Devaux et al., *Chemical Abstracts*, 123(218402), (1996).
Dhein et al., *Nature*, 373, 438-441 (1995).
Goeddel et al., *Nucl. Acids Res.*, 8(18), 4057-4074 (1980).
Grima et al., *J. Neurochem.*, 59(6), 2318-2323 (1992).
Higgins et al., *J. Immunol.*, 140(2), 440-445 (1988).
Horvath et al., *Biochemistry*, 29(11), 2635-2638 (1990).
Inobe et al., *Neurology*, 42( Suppl. 3 ), Abstr. 87P, 159-160 (1992).
Jingwu et al., *Ann. Neurol.*, 32(3), 330-338 (1992).
Johns et al., *J. Immunol.*, 154, 5536-5541 (1995).
Johnson et al., *J. Neuroimmunol.*, 13, 99-108 (1986).
Ju et al., *Nature*, 373, 444-448 (1995).
Liblau et al., *Eur. J. Immunol.*, 21, 1391-1395 (1991).
Luckow et al., *Bio/Technology*, 6, 47-55 (1988).
Martin et al., *J. Immunol.*, 148(5), 1359-1366 (1992).
Miller et al., *Neurology*, 42(suppl. 3), 559S, 301 (1992).
Miller et al., *Proc. Natl. Acad. Sci. USA*, 89, 421-425 (1992).
Moir et al., *Meth. Enzymol.*, 194, 491-507 (1991).
Nagata et al., *Immunol. Today*, 16(1), 39-43 (1995).
Pham-Dinh et al., *J. Neurochem.*, 63(6), 2353-2356 (1994).
Proost et al., *Biochem. Biophys. Res. Commun.*, 192(3), 1175-1181 (1993).
Qin et al., *Eur. J. Immunol.* 19, 373-380 (1989).
Racke et al., *J. Immunol.*, 154, 450-458 (1995).
Roitt et al., *Immunology*, 4th Ed., 11.1-11.2 (1996).
Rollins et al., *Hum. Gene Ther.*, 7, 619-626 (1996).
Salvetti et al., *Eur. J. Immunol.*, 23, 1232-1239 (1993).
Schena et al., *Meth. Enzymol.*, 194, 389-398 (1991).
Shpaer, *J. Mol. Biol.* 188, 555-564 (1986).
Sobel et al., *Neurochem. Res.*, 19(8), 915-921 (1994)
Steinman, *Cell*, 80, 7-10 (1995).
Strasser, *Nature*, 373, 385-386 (1995).
Streicher et al., *Biol. Chem. Hoppe-Seyler*, 370, 503-510 (1989).
Taguchi et al., *J. Immunol. Meth.*, 128, 65-73 (1990).
Talib et al., *Gene*, 98, 289-293 (1991).
Tisch et al., *Nature*, 366, 72-75 (1993).
Trotter et al., *Neuroimmunology, Abst.* 1117, 196A (1993).
Tuohy, *Neurochem. Res.*, 19(8), 935-944 (1994).
Utz et al., *Proc. Natl. Acad. Sci. USA*, 91, 5567-5571 (1994).
Vandenbark et al., *Nature*, 341, 541-544 (1989).
Wucherpfennig et al., *J Immunol.*, 152, 5581-5592 (1994).
Old et al., *Principles of Gene Manipulation*, 3rd Ed., 146-147 (1985).

* cited by examiner

```
    Nde I
fCATATGGCGTCTCAGAAACGTCCGTCCCAGCGTCACGGCTCCAAATACCTGGCCACCGCC60
a   ATG     A    GA A    C     AG    A     G         A  A
    MetAlaSerGlnLysArgProSerGlnArgHisGlySerLysTyrLeuAlaThrAla overlap: oligos 1 and 2
fAGCACCATGGACCATGCCCGTCATGGCTTCCTGCCGCGTCACCGTGACACCGGCATCCTG120
a  T           A G         C   AA G  AA    G          T
  SerThrMetAspHisAlaArgHisGlyPheLeuProArgHisArgAspThrGlyIleLeu fGACTCCATCGGCCGCTTCTTCGGCGGTGACCGTGGTGCGCCGAAACGTGGCTCTGGCAAA180
a       G     T      A G       A G      A  G              ---
  AspSerIleGlyArgPhePheGlyGlyAspArgGlyAlaProLysArgGlySerGlyLys overlap: oligos 3 and 2
fGTGCCGTGGCTGAAACCGGGCCGTAGCCCGCTGCCGTCTCATGCCCGTAGCCAGCCGGGC240
a ----------------------------------------------------------
  ValProTrpLeuLysProGlyArgSerProLeuProSerHisAlaArgSerGlnProGly fCTGTGCAACATGTACAAAGACTCCCACCACCCGGCTCGTACCGCGCACTATGGCTCCCTG300
a-------------- G   A           AA A  T   T
  LeuCysAsnMetTyrLysAspSerHisHisProAlaArgThrAlaHisTyrGlySerLeu overlap: oligos 3 and 4
fCCGCAGAAATCCCACGGCCGTACCCAGGATGAAAACCCGGTGGTGCACTTCTTCAAAAAC360
a       C   G A      G  A          C A C              G
  ProGlnLysSerHisGlyArgThrGlnAspGluAsnProValValHisPhePheLysAsn fATTGTGACCCCGCGTACCCCGCCGCCGTCTCAGGGCAAAGGCCGTGGCCTGTCCCTGAGC420
a      G T  C  A  A  C       G    A  G  GA A
  IleValThrProArgThrProProProSerGlnGlyLysGlyArgGlyLeuSerLeuSer overlap: oligo 5 and 4                                *
fCGTTTCAGCTGGGGCGCCGAAGGCCAGCGTCCGGGCTTCGGTTACGGCGGCCGTGCGTCC480
aA A  T     G            AA A T   A  A
  ArgPheSerTrpGlyAlaGluGlyGlnArgProGlyPheGlyTyrGlyGlyArgAlaSer overlap: oligos 5 and 6
                                                *       *
fGACTATAAATCTGCTCACAAAGGCTTCAAAGGCGTGGATGCCCAGGGTACCTTGTCCAAA540
a      G      GA    GA C             C  GC T
  AspTyrLysSerAlaHisLysGlyPheLysGlyValAspAlaGlnGlyThrLeuSerLys fATTTTCAAACTGGGCGGCCGTGATAGCCGTTCTGGCTCTCCGATGGCTAGACGTCATCAC600
a    T G   A AA    T   C    A A C          C------
  IlePheLysLeuGlyGlyArgAspSerArgSerGlySerProMetAlaArgArgHisHis HindIII
fCATCACCATCACTAATAAGCTT622
a------------TAA
  HisHisHisHisEndEnd
```

*Fig 11*

Summary of Human MBP-Specific T Cell Proliferation Data

| Antigen | Human MBP-Specific T cell lines[a] | | | | | | | |
|---|---|---|---|---|---|---|---|---|
| | 2A2 (31-50) | 1G1/3A11/1H7[b] (59-84) | 3H5 (87-106) | 3H1 (106-125) | 2A4 (136-155) | 4G1 (141-170) | 5B2 (151-170) | Gimer (11-29) |
| MBP21.5 | +[c] | + | +[c] | + | + | ND | ND | + |
| MBP21.5C81S | + | + | + | ND[d] | ND | +[e] | +[e] | ND |

[a] Numbers in parentheses below the T cell line designation represent epitope specificity of human lines. Input recombinant antigen was 10 µg/ml unless noted.
[b] MBP exon 2 specific human T cell lines.
[c] Antigen concentration 20 µg/ml
[d] Not done
[e] Antigen concentration 50 µg/ml

Fig 13

SEQUENCE LISTING

```
<160> NUMBER OF SEQ ID NOS: 27

<210> SEQ ID NO 1
<211> LENGTH: 197
<212> TYPE: PRT
<213> ORGANISM: human

<400> SEQUENCE: 1

Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
            20                  25                  30

His Arg Asp Thr Gly Ile Leu Asp Ser Ile Gly Arg Phe Phe Gly Gly
        35                  40                  45

Asp Arg Gly Ala Pro Lys Arg Gly Ser Gly Lys Val Pro Trp Leu Lys
    50                  55                  60

Pro Gly Arg Ser Pro Leu Pro Ser His Ala Arg Ser Gln Pro Gly Leu
65                  70                  75                  80

Cys Asn Met Tyr Lys Asp Ser His His Pro Ala Arg Thr Ala His Tyr
                85                  90                  95

Gly Ser Leu Pro Gln Lys Ser His Gly Arg Thr Gln Asp Glu Asn Pro
            100                 105                 110

Val Val His Phe Phe Lys Asn Ile Val Thr Pro Arg Thr Pro Pro Pro
        115                 120                 125

Ser Gln Gly Lys Gly Arg Gly Leu Ser Leu Ser Arg Phe Ser Trp Gly
    130                 135                 140

Ala Glu Gly Gln Arg Pro Gly Phe Gly Tyr Gly Gly Arg Ala Ser Asp
145                 150                 155                 160

Tyr Lys Ser Ala His Lys Gly Phe Lys Gly Val Asp Ala Gln Gly Thr
                165                 170                 175

Leu Ser Lys Ile Phe Lys Leu Gly Gly Arg Asp Ser Arg Ser Gly Ser
            180                 185                 190

Pro Met Ala Arg Arg
        195

<210> SEQ ID NO 2
<211> LENGTH: 203
<212> TYPE: PRT
<213> ORGANISM: human
```

<400> SEQUENCE: 2

```
Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
            20                  25                  30

His Arg Asp Thr Gly Ile Leu Asp Ser Ile Gly Arg Phe Phe Gly Gly
        35                  40                  45

Asp Arg Gly Ala Pro Lys Arg Gly Ser Gly Lys Val Pro Trp Leu Lys
    50                  55                  60

Pro Gly Arg Ser Pro Leu Pro Ser His Ala Arg Ser Gln Pro Gly Leu
65                  70                  75                  80

Cys Asn Met Tyr Lys Asp Ser His His Pro Ala Arg Thr Ala His Tyr
                85                  90                  95

Gly Ser Leu Pro Gln Lys Ser His Gly Arg Thr Gln Asp Glu Asn Pro
            100                 105                 110

Val Val His Phe Phe Lys Asn Ile Val Thr Pro Arg Thr Pro Pro Pro
        115                 120                 125

Ser Gln Gly Lys Gly Arg Gly Leu Ser Leu Ser Arg Phe Ser Trp Gly
    130                 135                 140

Ala Glu Gly Gln Arg Pro Gly Phe Gly Tyr Gly Gly Arg Ala Ser Asp
145                 150                 155                 160

Tyr Lys Ser Ala His Lys Gly Phe Lys Gly Val Asp Ala Gln Gly Thr
                165                 170                 175

Leu Ser Lys Ile Phe Lys Leu Gly Gly Arg Asp Ser Arg Ser Gly Ser
            180                 185                 190

Pro Met Ala Arg Arg His His His His His His
            195                 200
```

<210> SEQ ID NO 3
<211> LENGTH: 203
<212> TYPE: PRT
<213> ORGANISM: human

<400> SEQUENCE: 3

```
Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
            20                  25                  30

His Arg Asp Thr Gly Ile Leu Asp Ser Ile Gly Arg Phe Phe Gly Gly
        35                  40                  45

Asp Arg Gly Ala Pro Lys Arg Gly Ser Gly Lys Val Pro Trp Leu Lys
    50                  55                  60

Pro Gly Arg Ser Pro Leu Pro Ser His Ala Arg Ser Gln Pro Gly Leu
65                  70                  75                  80

Ser Asn Met Tyr Lys Asp Ser His His Pro Ala Arg Thr Ala His Tyr
                85                  90                  95

Gly Ser Leu Pro Gln Lys Ser His Gly Arg Thr Gln Asp Glu Asn Pro
            100                 105                 110

Val Val His Phe Phe Lys Asn Ile Val Thr Pro Arg Thr Pro Pro Pro
        115                 120                 125

Ser Gln Gly Lys Gly Arg Gly Leu Ser Leu Ser Arg Phe Ser Trp Gly
    130                 135                 140

Ala Glu Gly Gln Arg Pro Gly Phe Gly Tyr Gly Gly Arg Ala Ser Asp
145                 150                 155                 160
```

-continued

```
Tyr Lys Ser Ala His Lys Gly Phe Lys Gly Val Asp Ala Gln Gly Thr
                165                 170                 175

Leu Ser Lys Ile Phe Lys Leu Gly Gly Arg Asp Ser Arg Ser Gly Ser
            180                 185                 190

Pro Met Ala Arg Arg His His His His His
        195                 200
```

<210> SEQ ID NO 4
<211> LENGTH: 172
<212> TYPE: PRT
<213> ORGANISM: human

<400> SEQUENCE: 4

```
His Met Ala Ser Gln Lys Arg Pro Ser Gln Arg His Gly Ser Lys Tyr
1               5                   10                  15

Leu Ala Thr Ala Ser Thr Met Asp His Ala Arg His Gly Phe Leu Pro
            20                  25                  30

Arg His Arg Asp Thr Gly Ile Leu Asp Ser Ile Gly Arg Phe Phe Gly
        35                  40                  45

Gly Asp Arg Gly Ala Pro Lys Arg Gly Ser Gly Lys Asp Ser His His
50                  55                  60

Pro Ala Arg Thr Ala His Tyr Gly Ser Leu Pro Gln Lys Ser His Gly
65                  70                  75                  80

Arg Thr Gln Asp Glu Asn Pro Val Val His Phe Lys Asn Ile Val
                85                  90                  95

Thr Pro Arg Thr Pro Pro Ser Gln Gly Lys Gly Arg Gly Leu Ser
            100                 105                 110

Leu Ser Arg Phe Ser Trp Gly Ala Glu Gly Gln Arg Pro Gly Phe Gly
            115                 120                 125

Tyr Gly Gly Arg Ala Ser Asp Tyr Lys Ser Ala His Lys Gly Phe Lys
        130                 135                 140

Gly Val Asp Ala Gln Gly Thr Leu Ser Lys Ile Phe Lys Leu Gly Gly
145                 150                 155                 160

Arg Asp Ser Arg Ser Gly Ser Pro Met Ala Arg Arg
                165                 170
```

<210> SEQ ID NO 5
<211> LENGTH: 130
<212> TYPE: DNA
<213> ORGANISM: artificial sequence
<220> FEATURE:
<223> OTHER INFORMATION: overlapping oligonucleotide

<400> SEQUENCE: 5

```
ggaattccgt aaggaggtat agcatatggc gtctcagaaa cgtccgtccc agcgtcacgg    60
ctccaaatac ctggccaccg ccagcaccat ggaccatgcc cgtcatggct tcctgccgcg   120
tcaccgtgac                                                         130
```

<210> SEQ ID NO 6
<211> LENGTH: 129
<212> TYPE: DNA
<213> ORGANISM: artificial sequence
<220> FEATURE:
<223> OTHER INFORMATION: overlapping oligonucleotide

<400> SEQUENCE: 6

```
gacggcagcg ggctacggcc cggtttcagc cacggcactt tgccagagcc acgtttcggc    60
gcaccacggt caccgccgaa gaagcggccg atggagtcca ggatgccggt gtcacggtga   120
```

```
cgcggcagg                                                                    129

<210> SEQ ID NO 7
<211> LENGTH: 133
<212> TYPE: DNA
<213> ORGANISM: artificial sequence
<220> FEATURE:
<223> OTHER INFORMATION: overlapping oligonucleotide

<400> SEQUENCE: 7
ccgggccgta gcccgctgcc gtctcatgcc cgtagccagc cgggcctgtg caacatgtac        60
aaagactccc accaccggc tcgtaccgcg cactatggct ccctgccgca gaaatcccac        120
ggccgtaccc agg                                                              133

<210> SEQ ID NO 8
<211> LENGTH: 131
<212> TYPE: DNA
<213> ORGANISM: artificial sequence
<220> FEATURE:
<223> OTHER INFORMATION: overlapping oligonucleotide

<400> SEQUENCE: 8
cggcgcccca gctgaaacgg ctcagggaca ggccacggcc tttgccctga cacggcggcg        60
gggtacgcgg ggtcacaatg tttttgaaga agtgcaccac cgggttttca tcctgggtac        120
ggccgtggga t                                                                131

<210> SEQ ID NO 9
<211> LENGTH: 119
<212> TYPE: DNA
<213> ORGANISM: artificial sequence
<220> FEATURE:
<223> OTHER INFORMATION: overlapping oligonucleotide

<400> SEQUENCE: 9
gccgtttcag ctggggcgcc gaaggccagc gtccgggctt cggctacggc ggccgtgcgt        60
ccgactataa atctgctcac aaaggcttca aggcgtgga tgcccagggc accctgtcc         119

<210> SEQ ID NO 10
<211> LENGTH: 111
<212> TYPE: DNA
<213> ORGANISM: artificial sequence
<220> FEATURE:
<223> OTHER INFORMATION: overlapping oligonucleotide

<400> SEQUENCE: 10
ccccaagctt attagtgatg gtgatggtga tgacgtctag ccatcggaga gccagaacgg        60
ctatcacggc cgcccagttt gaaaattttg gacagggtgc cctgggcatc c                111

<210> SEQ ID NO 11
<211> LENGTH: 4059
<212> TYPE: DNA
<213> ORGANISM: artificial sequence
<220> FEATURE:
<223> OTHER INFORMATION: eukaryotic vector pAPEX-1

<400> SEQUENCE: 11
acgcgttgac attgattatt gactagttat taatagtaat caattacggg gtcattagtt        60
catagcccat atatggagtt ccgcgttaca taacttacgg taaatggccc cgcctggctg        120
accgcccaac gacccccgcc cattgacgtc aataatgacg tatgttccca tagtaacgcc        180
```

-continued

```
aatagggact ttccattgac gtcaatgggt ggactattta cggtaaactg cccacttggc      240
agtacatcaa gtgtatcata tgccaagtac gccccctatt gacgtcaatg acggtaaatg      300
gcccgcctgg cattatgccc agtacatgac cttatgggac tttcctactt ggcagtacat      360
ctacgtatta gtcatcgcta ttaccatggt gatgcggttt tggcagtaca tcaatgggcg      420
tggatagcgg tttgactcac ggggatttcc aagtctccac cccattgacg tcaatgggag      480
tttgttttgg caccaaaatc aacgggactt tccaaaatgt cgtaacaact ccgccccatt      540
gacgcaaatg gcggtaggc gtgtacggtg ggaggtctat ataagcagag ctcgtttagt       600
gaaccgtcag aattctgttg ggctcgcggt tgattacaaa ctcttcgcgg tctttccagt      660
actcttggat cggaaacccg tcggcctccg aacggtactc cgccaccgag ggacctgagc      720
gagtccgcat cgaccggatc ggaaaacctc tcgactgttg gggtgagtac tccctctcaa      780
aagcgggcat gacttctgcg ctaagattgt cagtttccaa aaacgaggag gatttgatat      840
tcacctggcc cgcggtgatg cctttgaggg tggccgcgtc catctggtca gaaaagacaa      900 tcttttgtt gtcaagcttg aggtgtggca ggcttgagat ctggccatac acttgagtga       960
caatgacatc cactttgcct ttctctccac aggtgtccac tcccaggtcc aactgcaggt     1020
cgaccggctt ggtaccgagc tcggatccac tagtaacggc cgccagtgtg ctggaattct     1080
gcagatatcc atcacactgg cggccgctcg agcatgcatc tagaacttgt ttattgcagc     1140
ttataatggt tacaaataaa gcaatagcat cacaaatttc acaaataaag catttttttc     1200
actgcattct agttgtggtt tgtccaaact catcaatgta tcttatcatg tctggatcga     1260
tcccgccatg gtatcaacgc catatttcta tttacagtag ggacctcttc gttgtgtagg     1320
taccgctgta ttcctaggga aatagtagag gcaccttgaa ctgtctgcat cagccatata     1380
gcccccgctg ttcgacttac aaacacaggc acagtactga caaacccata cacctcctct     1440
gaaataccca tagttgctag ggctgtctcc gaactcatta caccctccaa agtcagagct     1500
gtaatttcgc catcaagggc agcgagggct tctccagata aaatagcttc tgccgagagt     1560
cccgtaaggg tagacacttc agctaatccc tcgatgaggt ctactagaat agtcagtgcg     1620
gctcccattt tgaaaattca cttacttgat cagcttcaga agatggcgga gggcctccaa     1680
cacagtaatt ttcctcccga ctcttaaaat agaaaatgtc aagtcagtta agcaggaagt     1740
ggactaactg acgcagctgg ccgtgcgaca tcctctttta attagttgct aggcaacgcc     1800
ctccagaggg cgtgtggttt tgcaagagga agcaaaagcc tctccaccca ggcctagaat     1860
gtttccaccc aatcattact atgacaacag ctgttttttt tagtattaag cagaggccgg     1920 ggaccctgg gcccgcttac tctggagaaa aagaagagag gcattgtaga ggcttccaga     1980
ggcaacttgt caaaacagga ctgcttctat ttctgtcaca ctgtctggcc ctgtcacaag     2040
gtccagcacc tccataccc ctttaataag cagtttggga acgggtgcgg gtcttactcc      2100
gcccatcccg cccctaactc cgcccagttc cgcccattct ccgccccatg ctgactaat     2160 tttttttatt tatgcagagg ccgaggccgc ctcggcctct gagctattcc agaagtagtg     2220
aggaggcttt tttggaggcc taggcttttg caaaaggag ctcccagcaa aaggccagga      2280
accgtaaaaa ggccgcgttg ctggcgtttt tccataggct ccgcccccct gacgagcatc     2340
acaaaaatcg acgctcaagt cagaggtggc gaaacccgac aggactataa agataccagg     2400
cgtttccccc tggaagctcc ctcgtgcgct ctcctgttcc gaccctgccg cttaccggat     2460
acctgtccgc ctttctccct tcgggaagcg tggcgctttc tcaatgctca cgctgtaggt     2520
atctcagttc ggtgtaggtc gttcgctcca agctgggctg tgtgcacgaa ccccccgttc     2580
```

```
agcccgaccg ctgcgcctta tccggtaact atcgtcttga gtccaacccg gtaagacacg    2640
acttatcgcc actggcagca gccactggta acaggattag cagagcgagg tatgtaggcg    2700
gtgctacaga gttcttgaag tggtggccta actacggcta cactagaagg acagtatttg    2760
gtatctgcgc tctgctgaag ccagttacct tcggaaaaag agttggtagc tcttgatccg    2820
gcaaacaaac caccgctggt agcggtggtt ttttgtttg caagcagcag attacgcgca    2880 gaaaaaagg atctcaagaa gatcctttga tcttttctac ggggtctgac gctcagtgga    2940
acgaaaactc acgttaaggg attttggtca tgagattatc aaaaggatc ttcacctaga    3000 tccttttaaa ttaaaaatga agttttaaat caatctaaag tatatatgag taaacttggt    3060
ctgacagtta ccaatgctta atcagtgagg cacctatctc agcgatctgt ctatttcgtt    3120
catccatagt tgcctgactc cccgtcgtgt agataactac gatacgggag ggcttaccat    3180
ctggccccag tgctgcaatg ataccgcgag acccacgctc accggctcca gatttatcag    3240
caataaacca gccagccgga agggccgagc gcagaagtgg tcctgcaact ttatccgcct    3300
ccatccagtc tattaattgt tgccgggaag ctagagtaag tagttcgcca gttaatagtt    3360
tgcgcaacgt tgttgccatt gctacaggca tcgtggtgtc acgctcgtcg tttggtatgg    3420
cttcattcag ctccggttcc caacgatcaa ggcgagttac atgatccccc atgttgtgca    3480
aaaaagcggt tagctccttc ggtcctccga tcgttgtcag aagtaagttg gccgcagtgt    3540
tatcactcat ggttatggca gcactgcata attctcttac tgtcatgcca tccgtaagat    3600
gcttttctgt gactggtgag tactcaacca agtcattctg agaatagtgt atgcggcgac    3660
cgagttgctc ttgcccggcg tcaatacggg ataataccgc gccacatagc agaactttaa    3720
aagtgctcat cattggaaaa cgttcttcgg ggcgaaaact ctcaaggatc ttaccgctgt    3780
tgagatccag ttcgatgtaa cccactcgtg cacccaactg atcttcagca tcttttactt    3840
tcaccagcgt ttctgggtga gcaaaaacag gaaggcaaaa tgccgcaaaa aagggaataa    3900
gggcgacacg gaaatgttga atactcatac tcttcctttt tcaatattat tgaagcattt    3960
atcagggtta ttgtctcatg agcggataca tatttgaatg tatttagaaa aataaacaaa    4020 tagggggttcc gcgcacattt ccccgaaaag tgccacctg                          4059
```

<210> SEQ ID NO 12
<211> LENGTH: 8540
<212> TYPE: DNA
<213> ORGANISM: artificial sequence
<220> FEATURE:
<223> OTHER INFORMATION: eukaryotic vector pAPEX-3p

<400> SEQUENCE: 12

```
gtgaccaata caaaacaaaa gcgcccctcg taccagcgaa gaaggggcag agatgccgta     60
gtcaggttta gttcgtccgg cggcggggga tctgtatggt gcactctcag tacaatctgc    120
tctgatgccg catagttaag ccagtatctg ctccctgctt gtgtgttgga ggtcgctgag    180
tagtgcgcga gcaaaattta agctacaaca aggcaaggct tgaccgacaa ttgcatgaag    240
aatctgctta gggttaggcg ttttgcgctg cttcgcgatg tacgggccag atatacgcgt    300
tgacattgat tattgactag ttattaatag taatcaatta cggggtcatt agttcatagc    360
ccatatatgg agttccgcgt tacataactt acggtaaatg gcccgcctgg ctgaccgccc    420
aacgaccccc gcccattgac gtcaataatg acgtatgttc ccatagtaac gccaataggg    480
actttccatt gacgtcaatg ggtggactat ttacggtaaa ctgcccactt ggcagtacat    540
```

```
caagtgtatc atatgccaag tacgcccect attgacgtca atgacggtaa atggcccgcc      600
tggcattatg cccagtacat gaccttatgg gactttccta cttggcagta catctacgta      660
ttagtcatcg ctattaccat ggtgatgcgg ttttggcagt acatcaatgg gcgtggatag      720
cggtttgact cacggggatt tccaagtctc cacccattg acgtcaatgg gagtttgttt       780
tggcaccaaa atcaacggga ctttccaaaa tgtcgtaaca actccgcccc attgacgcaa      840
atgggcggta ggcgtgtacg gtgggaggtc tatataagca gagctcgttt agtgaaccgt      900
cagaattctg ttgggctcgc ggttgattac aaactcttcg cggtctttcc agtactcttg      960
gatcggaaac ccgtcggcct ccgaacggta ctccgccacc gagggacctg agcgagtccg     1020
catcgaccgg atcggaaaac ctctcgactg ttggggtgag tactccctct caaaagcggg     1080
catgacttct gcgctaagat tgtcagtttc caaaaacgag gaggatttga tattcacctg     1140
gcccgcggtg atgcctttga gggtggccgc gtccatctgg tcagaaaaga caatctttt      1200
gttgtcaagc ttgaggtgtg gcaggcttga gatctggcca tacacttgag tgacaatgac     1260
atccactttg cctttctctc cacaggtgtc cactcccagg tccaactgca ggtcgaccgg     1320
cttggtaccg agctcggatc ctctagagtc gacctgcagg catgcaagct tggcactggc     1380
cgtcgtttta caacgtcgtg actgggaaaa ccctggcgtt acccaactta atcgccttgc     1440
agcacatccc cctttcgcca gctggcgtaa tagcgaagag gcccgcaccg atccagacat     1500
gataagatac attgatgagt ttggacaaac cacaactaga atgcagtgaa aaaatgctt     1560
tatttgtgaa atttgtgatg ctattgcttt atttgtaacc attataagct gcaataaaca     1620
agttaacaac aacaattgca ttcattttat gtttcaggtt cagggggagg tgtgggaggt     1680
tttttaaagc aagtaaaacc tctacaaatg tggtatggct gattatgatc cccaggaagc     1740
tcctctgtgt cctcataaac cctaacctcc tctacttgag aggacattcc aatcataggc     1800
tgcccatcca ccctctgtgt cctcctgtta attaggtcac ttaacaaaaa ggaaattggg     1860
taggggtttt tcacagaccg cttctaagg gtaattttaa aatatctggg aagtcccttc      1920
cactgctgtg ttccagaagt gttggtaaac agcccacaaa tgtcaacagc agaaacatac     1980
aagctgtcag cttgcacaa gggcccaaca ccctgctcat caagaagcac tgtggttgct      2040
gtgttagtaa tgtgcaaaac aggaggcaca ttttcccac ctgtgtaggt tccaaaatat      2100
ctagtgtttt catttttact tggatcagga acccagcact ccactggata agcattatcc     2160
ttatccaaaa cagccttgtg gtcagtgttc atctgctgac tgtcaactgt agcatttttt     2220
ggggttacag tttgagcagg atatttggtc ctgtagtttg ctaacacacc ctgcagctcc     2280
aaaggttccc caccaacagc aaaaaaatga aaatttgacc cttgaatggg ttttccagca     2340
ccatttcat gagttttttg tgtccctgaa tgcaagttta acatagcagt taccccaata     2400
acctcagttt taacagtaac agcttcccac atcaaaatat ttccacaggt taagtcctca     2460
tttgtagaat tcgccagcac agtggtcgac cctgtggatg tgtgtcactt agggtgtgga     2520
aagtccccag gctccccagc aggcagaagt atgcaaagca tgcatctcaa ttagtcagca     2580
accaggtgtg gaaagtcccc aggctcccca gcaggcagaa gtatgcaaag catgcatctc     2640
aattagtcag caaccatagt cccgccccta ctccgcccca tccgccccta aactccgccc     2700
agttccgccc attctccgcc ccatggctga ctaatttttt ttatttatgc agaggccgag     2760
gccgcctcgg cctctgagct attccagaag tagtgaggag cttttttgg aggcctaggc      2820
ttttgcaaaa gcttaccatg accgagtaca agcccacggt gcgcctcgcc acccgcgacg     2880
acgtccccg ggccgtacgc accctcgccg ccgcgttcgc cgactacccc gccacgcgcc      2940
```

-continued

```
acaccgtcga cccggaccgc cacatcgagc gggtcaccga gctgcaagaa ctcttcctca   3000
cgcgcgtcgg gctcgacatc ggcaaggtgt gggtcgcgga cgacggcgcc gcggtggcgg   3060
tctggaccac gccggagagc gtcgaagcgg gggcggtgtt cgccgagatc ggcccgcgca   3120
tggccgagtt gagcggttcc cggctggccg cgcagcaaca gatggaaggc ctcctggcgc   3180
cgcaccggcc caaggagccc gcgtggttcc tggccaccgt cggcgtctcg cccgaccacc   3240
agggcaaggg tctgggcagc gccgtcgtgc tccccggagt ggaggcggcc gagcgcgccg   3300
gggtgcccgc cttcctggag acctccgcgc ccgcaaccct cccttctac gagcggctcg    3360
gcttcaccgt caccgccgac gtcgagtgcc cgaaggaccg cgcgacctgg tgcatgaccc   3420
gcaagcccgg tgcctgacgc ccgcccacg acccgcagcg cccgaccgaa aggagcgcac    3480
gaccccatgc atcgataaaa taaagatttt tatttagtct ccagaaaaag gggggaatga   3540
aagaccccac ctgtaggttt ggcaagctag aacttgttta ttgcagctta taatggttac   3600
aaataaagca atagcatcac aaatttcaca aataaagcat ttttttcact gcattctagt   3660
tgtggtttgt ccaaactcat caatgtatct tatcatgtct ggatcgatcc cgccatggta   3720
tcaacgccat atttctattt acagtaggga cctcttcgtt gtgtaggtac cccgggttcg   3780
aaatcgaatt cgccaatgac aagacgctgg gcggggtttg tgtcatcata gaactaaaga   3840
catgcaaata tatttcttcc ggggacaccg ccagcaaacg cgagcaacgg ccacggggga   3900
tgaagcagcc cggcggcacc tcgctaacgg attcaccact ccaagaattg gagccaatca   3960
attcttgcgg agaactgtga atgcgcaaac caacccttgg cagaacatat ccatcgcgtc   4020
cgccatctcc agcagccgca cgcggcgcat ctcggggccg acgcgctggg ctacgtcttg   4080
ctggcgttcg cgacgcgagg ctggatggcc ttccccatta tgattcttct cgcttccggc   4140
ggcatcggga tgcccgcgtt gcaggccatg ctgtccaggc aggtagatga cgaccatcag   4200
ggacagcttc aaggatcgct cgcggctctt accagcgcca gcaaaaggcc aggaaccgta   4260
aaaaggccgc gttgctggcg ttttttccata ggctccgccc ccctgacgag catcacaaaa   4320
atcgacgctc aagtcagagg tggcgaaacc cgacaggact ataaagatac caggcgtttc   4380
cccctggaag ctccctcgtg cgctctcctg ttccgaccct gccgcttacc ggatacctgt   4440
ccgcctttct cccttcggga agcgtggcgc tttctcatag ctcacgctgt aggtatctca   4500
gttcggtgta ggtcgttcgc tccaagctgg gctgtgtgca cgaaccccc gttcagcccg     4560
accgctgcgc cttatccggt aactatcgtc ttgagtccaa cccggtaaga cacgacttat   4620
cgccactggc agcagccact ggtaacagga ttagcagagc gaggtatgta ggcggtgcta   4680
cagagttctt gaagtggtgg cctaactacg gctacactag aaggacagta tttggtatct   4740
gcgctctgct gaagccagtt accttcggaa aaagagttgg tagctcttga tccggcaaac   4800
aaaccaccgc tggtagcggt ggtttttttg tttgcaagca gcagattacg cgcagaaaaa   4860
aaggatctca agaagatcct ttgatctttt ctacgggtc tgacgctcag tggaacgaaa     4920
actcacgtta agggattttg gtcatgagat tatcaaaaag gatcttcacc tagatccttt   4980
taaattaaaa atgaagtttt aaatcaatct aaagtatata tgagtaaact ggtctgaca    5040
gttaccaatg cttaatcagt gaggcaccta tctcagcgat ctgtctattt cgttcatcca   5100
tagttgcctg actccccgtc gtgtagataa ctacgatacg ggagggctta ccatctggcc   5160
ccagtgctgc aatgataccg cgagacccac gctcaccggc tccagattta tcagcaataa   5220
accagccagc cggaagggcc gagcgcagaa gtggtcctgc aactttatcc gcctccatcc   5280
```

| | |
|---|---|
| agtctattaa ttgttgccgg gaagctagag taagtagttc gccagttaat agtttgcgca | 5340 |
| acgttgttgc cattgctgca ggcatcgtgg tgtcacgctc gtcgtttggt atggcttcat | 5400 |
| tcagctccgg ttcccaacga tcaaggcgag ttacatgatc ccccatgttg tgcaaaaaag | 5460 |
| cggttagctc cttcggtcct ccgatcgttg tcagaagtaa gttggccgca gtgttatcac | 5520 |
| tcatggttat ggcagcactg cataattctc ttactgtcat gccatccgta agatgctttt | 5580 |
| ctgtgactgg tgagtactca accaagtcat tctgagaata gtgtatgcgg cgaccgagtt | 5640 |
| gctcttgccc ggcgtcaaca cgggataata ccgcgccaca tagcagaact ttaaaagtgc | 5700 |
| tcatcattgg aaaacgttct cgggggcgaa aactctcaag gatcttaccg ctgttgagat | 5760 |
| ccagttcgat gtaacccact cgtgcaccca actgatcttc agcatctttt actttcacca | 5820 |
| gcgtttctgg gtgagcaaaa acaggaaggc aaaatgccgc aaaaaaggga ataagggcga | 5880 |
| cacggaaatg ttgaatactc atactcttcc ttttcaata ttattgaagc atttatcagg | 5940 |
| gttattgtct catgagcgga tacatatttg aatgtattta gaaaaataaa caaatagggg | 6000 |
| ttccgcgcac atttccccga aaagtgccac ctgacgtcta agaaaccatt attatcatga | 6060 |
| cattaaccta taaaaatagg cgtatcacga ggcccttttcg tcttcaagaa ttctcatgtt | 6120 |
| tgacagctta tcgtagacat catgcgtgct gttggtgtat ttctggccat ctgtcttgtc | 6180 |
| accattttcg tcctcccaac atggggcaat tgggcatacc catgttgtca cgtcactcag | 6240 |
| ctccgcgctc aacaccttct cgcgttggaa acattagcg acatttacct ggtgagcaat | 6300 |
| cagacatgcg acggctttag cctggcctcc ttaaattcac ctaagaatgg gagcaaccag | 6360 |
| caggaaaagg acaagcagcg aaaattcacg cccccttggg aggtggcggc atatgcaaag | 6420 |
| gatagcactc ccactctact actgggtatc atatgctgac tgtatatgca tgaggatagc | 6480 |
| atatgctacc cggatacaga ttaggatagc atatactacc cagatataga ttaggatagc | 6540 |
| atatgctacc cagatataga ttaggatagc ctatgctacc cagatataaa ttaggatagc | 6600 |
| atatactacc cagatataga ttaggatagc atatgctacc cagatataga ttaggatagc | 6660 |
| ctatgctacc cagatataga ttaggatagc atatgctacc cagatataga ttaggatagc | 6720 |
| atatgctatc cagatatttg ggtagtatat gctacccaga tataaattag gatagcatat | 6780 |
| actaccctaa tctctattag gatagcatat gctacccgga tacagattag gatagcatat | 6840 |
| actacccaga tatagattag gatagcatat gctacccaga tatagattag gatagcctat | 6900 |
| gctacccaga tataaattag gatagcatat actacccaga tatagattag gatagcatat | 6960 |
| gctacccaga tatagattag gatagcctat gctacccaga tatagattag gatagcatat | 7020 |
| gctatccaga tatttgggta gtatatgcta cccatggcaa cattagccca ccgtgctctc | 7080 |
| agcgacctcg tgaatatgag gaccaacaac cctgtgcttg gcgctcaggc gcaagtgtgt | 7140 |
| gtaatttgtc ctccagatcg cagcaatcgc gcccctatct tggcccgccc acctacttat | 7200 |
| gcaggtattc cccgggggtgc cattagtggt tttgtgggca agtggtttga ccgcagtggt | 7260 |
| tagcggggtt acaatcagcc aagttattac acccttattt tacagtccaa aaccgcaggg | 7320 |
| cggcgtgtgg gggctgacgc gtgccccac tccacaattt caaaaaaaag agtggccact | 7380 |
| tgtctttgtt tatgggcccc attggcgtgg agcccgtttt aattttcggg ggtgttagag | 7440 |
| acaaccagtg gagtccgctg ctgtcggcgt ccactctctt tccccttgtt acaaatagag | 7500 |
| tgtaacaaca tggttcacct gtcttggtcc ctgcctggga cacatcttaa taacccagt | 7560 |
| atcatattgc actaggatta tgtgttgccc atagccataa attcgtgtga gatggacatc | 7620 |
| cagtctttac ggcttgtccc caccccatgg atttctattg ttaaagatat tcagaatgtt | 7680 |

```
tcattcctac actagtattt attgcccaag gggtttgtga gggttatatt ggtgtcatag      7740
cacaatgcca ccactgaacc ccccgtccaa attttattct gggggcgtca cctgaaacct      7800
tgttttcgag cacctcacat acaccttact gttcacaact cagcagttat tctattagct      7860
aaacgaagga gaatgaagaa gcaggcgaag attcaggaga gttcactgcc cgctccttga      7920
tcttcagcca ctgcccttgt gactaaaatg gttcactacc ctcgtggaat cctgaccccca     7980 tgtaaataaa accgtgacag ctcatggggt gggagatatc gctgttcctt aggacccttt      8040
tactaaccct aattcgatag catatgcttc ccgttgggta acatatgcta ttgaattagg      8100
gttagtctgg atagtatata ctactacccg ggaagcatat gctacccgtt tagggttaac      8160 aaggggggcct tataaacact attgctaatg ccctcttgag ggtccgctta tcggtagcta     8220
cacaggcccc tctgattgac gttggtgtag cctcccgtag tcttcctggg cccctgggag      8280
gtacatgtcc cccagcattg gtgtaagagc ttcagccaag agttacacat aaaggcaatg      8340
ttgtgttgca gtccacagac tgcaaagtct gctccaggat gaaagccact cagtgttggc      8400
aaatgtgcac atccatttat aaggatgtca actacagtca gagaaccccct ttgtgtttgg     8460 tccccccccg tgtcacatgt ggaacagggc ccagttggca agttgtacca accaactgaa      8520
gggattacat gcactgcccc                                                  8540

<210> SEQ ID NO 13
<211> LENGTH: 22
<212> TYPE: DNA
<213> ORGANISM: artificial sequence
<220> FEATURE:
<223> OTHER INFORMATION: primer

<400> SEQUENCE: 13
catatggcgt cacagaagag ac                                               22

<210> SEQ ID NO 14
<211> LENGTH: 26
<212> TYPE: DNA
<213> ORGANISM: artificial sequence
<220> FEATURE:
<223> OTHER INFORMATION: primer

<400> SEQUENCE: 14
ggatccttag cgtctagcca tgggtg                                           26

<210> SEQ ID NO 15
<211> LENGTH: 36
<212> TYPE: DNA
<213> ORGANISM: artificial sequence
<220> FEATURE:
<223> OTHER INFORMATION: primer

<400> SEQUENCE: 15
gtctttgtac atgttcgaca ggcccggctg gctacg                                36

<210> SEQ ID NO 16
<211> LENGTH: 14
<212> TYPE: DNA
<213> ORGANISM: artificial sequence
<220> FEATURE:
<223> OTHER INFORMATION: primer

<400> SEQUENCE: 16
cagcaccatg gacc                                                        14
```

```
<210> SEQ ID NO 17
<211> LENGTH: 128
<212> TYPE: DNA
<213> ORGANISM: artificial sequence
<220> FEATURE:
<223> OTHER INFORMATION: sense oligonucleotide

<400> SEQUENCE: 17
ggtgcgccaa agcggggctc tggcaaggta ccctggctaa agccgggccg gagccctctg      60
ccctctcatg cccgcagcca gcctgggctg tgcaacatgt acaaggactc acaccacccg     120
gcaagaac                                                              128

<210> SEQ ID NO 18
<211> LENGTH: 19
<212> TYPE: DNA
<213> ORGANISM: artificial sequence
<220> FEATURE:
<223> OTHER INFORMATION: antisense oligonucleotide

<400> SEQUENCE: 18
gctagttatt gctcagcgg                                                   19

<210> SEQ ID NO 19
<211> LENGTH: 20
<212> TYPE: DNA
<213> ORGANISM: artificial sequence
<220> FEATURE:
<223> OTHER INFORMATION: T7 promoter oligonucleotide

<400> SEQUENCE: 19
taatacgact cactataggg                                                  20

<210> SEQ ID NO 20
<211> LENGTH: 39
<212> TYPE: DNA
<213> ORGANISM: artificial sequence
<220> FEATURE:
<223> OTHER INFORMATION: antisense oligonucleotide

<400> SEQUENCE: 20
ggctttagcc agggtacctt gccagagccc cgctttggc                             39

<210> SEQ ID NO 21
<211> LENGTH: 5248
<212> TYPE: DNA
<213> ORGANISM: artificial sequence
<220> FEATURE:
<223> OTHER INFORMATION: bacterial expression vector pET Trc S05/NI

<400> SEQUENCE: 21 tgcgaatgg gacgcgccct gtagcggcgc attaagcgcg gcgggtgtgg tggttacgcg       60
cagcgtgacc gctacacttg ccagcgccct agcgcccgct cctttcgctt tcttcccttc     120
ctttctcgcc acgttcgccg gctttccccg tcaagctcta aatcggggc tcccctttagg     180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggattt tgccgatttc ggcctattgg ttaaaaaatg agctgattta       420
acaaaaattt aacgcgaatt ttaacaaaat attaacgttt acaatttcag gtggcacttt     480
tcggggaaat gtgcgcggaa cccctatttg tttattttc taaatacatt caaatatgta     540
```

-continued

```
tccgctcatg agacaataac cctgataaat gcttcaataa tattgaaaaa ggaagagtat      600
gagtattcaa catttccgtg tcgcccttat tccctttttt gcggcatttt gccttcctgt      660
ttttgctcac ccagaaacgc tggtgaaagt aaaagatgct gaagatcagt tgggtgcacg      720
agtgggttac atcgaactgg atctcaacag cggtaagatc cttgagagtt ttcgccccga      780
agaacgtttt ccaatgatga gcacttttaa agttctgcta tgtggcgcgg tattatcccg      840
tattgacgcc gggcaagagc aactcggtcg ccgcatacac tattctcaga atgacttggt      900
tgagtactca ccagtcacag aaaagcatct tacggatggc atgacagtaa gagaattatg      960
cagtgctgcc ataaccatga gtgataacac tgcggccaac ttacttctga caacgatcgg     1020
aggaccgaag gagctaaccg cttttttgca acatggggg atcatgtaa ctcgccttga      1080
tcgttgggaa ccggagctga atgaagccat accaaacgac gagcgtgaca ccacgatgcc     1140
tgcagcaatg gcaacaacgt tgcgcaaact attaactggc gaactactta ctctagcttc     1200
ccggcaacaa ttaatagact ggatggaggc ggataaagtt gcaggaccac ttctgcgctc     1260
ggcccttccg gctggctggt ttattgctga taaatctgga gccggtgagc gtgggtctcg     1320
cggtatcatt gcagcactgg ggccagatgg taagccctcc cgtatcgtag ttatctacac     1380
gacgggagt caggcaacta tggatgaacg aaatagacag atcgctgaga taggtgcctc     1440
actgattaag cattggtaac tgtcagacca gtttactca tatatactt agattgattt     1500
aaaacttcat ttttaattta aaaggatcta ggtgaagatc cttttttgata atctcatgac     1560
caaaatccct taacgtgagt tttcgttcca ctgagcgtca gaccccgtag aaaagatcaa     1620
aggatcttct tgagatcctt ttttttctgcg cgtaatctgc tgcttgcaaa caaaaaaacc     1680
accgctacca gcggtggttt gtttgccgga tcaagagcta ccaactcttt ttccgaaggt     1740
aactggcttc agcagagcgc agataccaaa tactgtcctt ctagtgtagc cgtagttagg     1800
ccaccacttc aagaactctg tagcaccgcc tacatacctc gctctgctaa tcctgttacc     1860
agtggctgct gccagtggcg ataagtcgtg tcttaccggg ttggactcaa gacgatagtt     1920
accggataag cgcagcggt cgggctgaac ggggggttcg tgcacacagc ccagcttgga     1980
gcgaacgacc tacaccgaac tgagatacct acagcgtgag ctatgagaaa gcgccacgct     2040
tcccgaaggg agaaaggcgg acaggtatcc ggtaagcggc agggtcggaa caggagagcg     2100
cacgagggag cttccagggg gaaacgcctg gtatctttat agtcctgtcg ggtttcgcca     2160
cctctgactt gagcgtcgat ttttgtgatg ctcgtcaggg gggcggagcc tatggaaaaa     2220
cgccagcaac gcggcctttt tacggttcct ggccttttgc tggccttttg ctcacatgtt     2280
ctttcctgcg ttatccctg attctgtgga taaccgtatt accgcctttg agtgagctga     2340
taccgctcgc cgcagccgaa cgaccgagcg cagcgagtca gtgagcgagg aagcggaaga     2400
gcgcctgatg cggtattttc tccttacgca tctgtgcggt atttcacacc gcatatatgg     2460
tgcactctca gtacaatctg ctctgatgcc gcatagttaa gccagtatac actccgctat     2520
cgctacgtga ctgggtcatg gctgcgcccc gacacccgcc aacacccgct gacgcgccct     2580
gacgggcttg tctgctcccg gcatccgctt acagacaagc tgtgaccgtc tccgggagct     2640
gcatgtgtca gaggttttca ccgtcatcac cgaaacgcgc gaggcagctg cggtaaagct     2700
catcagcgtg gtcgtgaagc gattcacaga tgtctgcctg ttcatccgcg tccagctcgt     2760
tgagtttctc cagaagcgtt aatgtctggc ttctgataaa gcgggccatg ttaagggcgg     2820
ttttttcctg tttggtcact gatgcctccg tgtaaggggg atttctgttc atgggggtaa     2880
```

-continued

```
tgataccgat gaaacgagag aggatgctca cgatacgggt tactgatgat gaacatgccc    2940
ggttactgga acgttgtgag ggtaaacaac tggcggtatg gatgcggcgg gaccagagaa    3000
aaatcactca gggtcaatgc cagcgcttcg ttaatacaga tgtaggtgtt ccacagggta    3060
gccagcagca tcctgcgatg cagatccgga acataatggt gcagggcgct gacttccgcg    3120
tttccagact ttacgaaaca cggaaaccga agaccattca tgttgttgct caggtcgcag    3180
acgttttgca gcagcagtcg cttcacgttc gctcgcgtat cggtgattca ttctgctaac    3240
cagtaaggca accccgccag cctagccggg tcctcaacga caggagcacg atcatgcgca    3300
cccgtggggc cgccatgccg gcgataatgg cctgcttctc gccgaaacgt ttggtggcgg    3360
gaccagtgac gaaggcttga gcgagggcgt gcaagattcc gaataccgca agcgacaggc    3420
cgatcatcgt cgcgctccag cgaaagcggt cctcgccgaa aatgacccag agcgctgccg    3480
gcacctgtcc tacgagttgc atgataaaga agacagtcat aagtgcggcg acgatagtca    3540
tgccccgcgc ccaccggaag gagctgactg ggttgaaggc tctcaagggc atcggtcgag    3600
atcccggtgc ctaatgagtg agctaactta cattaattgc gttgcgctca ctgcccgctt    3660
tccagtcggg aaacctgtcg tgccagctgc attaatgaat cggccaacgc gcggggagag    3720
gcggtttgcg tattgggcgc cagggtggtt tttcttttca ccagtgagac gggcaacagc    3780
tgattgccct tcaccgcctg gccctgagag agttgcagca agcggtccac gctggtttgc    3840
cccagcaggc gaaaatcctg tttgatggtg gttaacggcg ggatataaca tgagctgtct    3900
tcggtatcgt cgtatcccac taccgagata tccgcaccaa cgcgcagccc ggactcggta    3960
atggcgcgca ttgcgcccag cgccatctga tcgttggcaa ccagcatcgc agtgggaacg    4020
atgccctcat tcagcatttg catggttttgt tgaaaaccgg acatggcact ccagtcgcct    4080
tcccgttccg ctatcggctg aatttgattg cgagtgagat atttatgcca gccagccaga    4140
cgcagacgcg ccgagacaga acttaatggg cccgctaaca gcgcgatttg ctggtgaccc    4200
aatgcgacca gatgctccac gcccagtcgc gtaccgtctt catgggagaa aataatactg    4260
ttgatgggtg tctggtcaga gacatcaaga aataacgccg gaacattagt gcaggcagct    4320
tccacagcaa tggcatcctg gtcatccagc ggatagttaa tgatcagccc actgacgcgt    4380
tgcgcgagaa gattgtgcac cgccgcttta caggcttcga cgccgcttcg ttctaccatc    4440
gacaccacca cgctggcacc cagttgatcg gcgcgagatt taatcgccgc gacaatttgc    4500
gacggcgcgt gcagggccag actggaggtg gcaacgccaa tcagcaacga ctgtttgccc    4560
gccagttgtt gtgccacgcg gttgggaatg taattcagct ccgccatcgc cgcttccact    4620 tttcccgcg ttttcgcaga aacgtggctg gcctggttca ccacgcggga aacggtctga    4680
taagagacac cggcatactc tgcgacatcg tataacgtta ctggtttcac attcaccacc    4740
ctgaattgac tctcttccgg gcgctatcat gccataccgc gaaaggtttt gcgccattcg    4800
atggtgtccg ggatctcgac gctctccctt atgcgactcc tgcattagga agcagcccag    4860
tagtaggttg aggccgttga gcaccgccgc cgcaaggaat ggtgcatgcg gtaccagctg    4920
ttgacaatta atcatccggc tcgtataata gtactgtgtg gaattgtgag cgctcacaat    4980
tccacacatc tagaaataat tttgtttaac tttaagaagg agatatacca tggagatctg    5040
gatccatcga tgaattcgag ctccgtcgac aagcttgcgg ccgcactcga gcaccaccac    5100
caccaccact gagatccggc tgctaacaaa gcccgaaagg aagctgagtt ggctgctgcc    5160
accgctgagc aataactagc ataacccctt ggggcctcta aacgggtctt gaggggtttt    5220
ttgctgaaag gaggaactat atccggat                                       5248
```

<210> SEQ ID NO 22
<211> LENGTH: 594
<212> TYPE: DNA
<213> ORGANISM: human

<400> SEQUENCE: 22

| | | | | | |
|---|---|---|---|---|---|
| atggcgtcac | agaagagacc | ctcccagagg | cacggatcca | agtacctggc | cacagcaagt | 60 |
| accatggacc | atgccaggca | tggcttcctc | ccaaggcaca | gagacacggg | catccttgac | 120 |
| tccatcgggc | gcttctttgg | cggtgacagg | ggtgcgccca | agcggggctc | tggcaaggta | 180 |
| ccctggctaa | agccgggccg | gagccctctg | ccctctcatg | cccgcagcca | gcctgggctg | 240 |
| tgcaacatgt | acaaggactc | acaccacccg | gcaagaactg | ctcactatgg | ctccctgccc | 300 |
| cagaagtcac | acggccggac | ccaagatgaa | accccgtag | tccacttctt | caagaacatt | 360 |
| gtgacgcctc | gcacaccacc | cccgtcgcag | ggaaagggga | gaggactgtc | cctgagcaga | 420 |
| tttagctggg | gggccgaagg | ccagagacca | ggatttggct | acggaggcag | agcgtccgac | 480 |
| tataaatcgg | ctcacaaggg | attcaaggga | gtcgatgccc | aggcacgct | ttccaaaatt | 540 |
| ttcaagctgg | gaggaagaga | tagtcgctct | ggatcaccca | tggctagacg | ctga | 594 |

<210> SEQ ID NO 23
<211> LENGTH: 612
<212> TYPE: DNA
<213> ORGANISM: artificial sequence
<220> FEATURE:
<223> OTHER INFORMATION: bacterialized human nucleic acid

<400> SEQUENCE: 23

| | | | | | |
|---|---|---|---|---|---|
| atggcgtctc | agaaacgtcc | gtcccagcgt | cacggctcca | atacctggc | caccgccagc | 60 |
| accatggacc | atgcccgtca | tggcttcctg | ccgcgtcacc | gtgacaccgg | catcctggac | 120 |
| tccatcggcc | gcttcttcgg | cggtgaccgt | ggtgcgccga | acgtggctc | tggcaaagtg | 180 |
| ccgtggctga | aaccgggccg | tagcccgctg | ccgtctcatg | cccgtagcca | gccgggcctg | 240 |
| tgcaacatgt | acaaagactc | ccaccacccg | gctcgtaccg | cgcactatgg | ctccctgccg | 300 |
| cagaaatccc | acggccgtac | ccaggatgaa | aacccggtgg | tgcacttctt | caaaaacatt | 360 |
| gtgaccccgc | gtaccccgcc | gccgtctcag | ggcaaaggcc | gtggcctgtc | cctgagccgt | 420 |
| ttcagctggg | gcgccgaagg | ccagcgtccg | ggcttcggtt | acggcggccg | tgcgtccgac | 480 |
| tataaatctg | ctcacaaagg | cttcaaaggc | gtggatgccc | agggtaccgt | gtccaaaatt | 540 |
| ttcaaactgg | gcggccgtga | tagccgttct | ggctctccga | tggctagacg | tcatcaccat | 600 |
| caccatcact | aa | | | | | 612 |

<210> SEQ ID NO 24
<211> LENGTH: 612
<212> TYPE: DNA
<213> ORGANISM: artificial sequence
<220> FEATURE:
<223> OTHER INFORMATION: bacterialized human nucleic acid

<400> SEQUENCE: 24

| | | | | | |
|---|---|---|---|---|---|
| atggcgtctc | agaaacgtcc | gtcccagcgt | cacggctcca | atacctggc | caccgccagc | 60 |
| accatggacc | atgcccgtca | tggcttcctg | ccgcgtcacc | gtgacaccgg | catcctggac | 120 |
| tccatcggcc | gcttcttcgg | cggtgaccgt | ggtgcgccga | acgtggctc | tggcaaagtg | 180 |
| ccgtggctga | aaccgggccg | tagcccgctg | ccgtctcatg | cccgtagcca | gccgggcctg | 240 |

```
tcgaacatgt acaaagactc ccaccacccg gctcgtaccg cgcactatgg ctccctgccg    300
cagaaatccc acggccgtac ccaggatgaa acccgtgg tgcacttctt caaaaacatt     360
gtgaccccgc gtaccccgcc gccgtctcag ggcaaaggcc gtggcctgtc cctgagccgt    420
ttcagctggg gcgccgaagg ccagcgtccg ggcttcggtt acggcggccg tgcgtccgac    480
tataaatctg ctcacaaagg cttcaaaggc gtggatgccc aggtaccctt gtccaaaatt    540
ttcaaactgg gcggccgtga tagccgttct ggctctccga tggctagacg tcatcaccat    600
caccatcact aa                                                        612
```

```
<210> SEQ ID NO 25
<211> LENGTH: 519
<212> TYPE: DNA
<213> ORGANISM: human

<400> SEQUENCE: 25
catatggcgt cacagaagag accctcccag aggcacggat ccaagtacct ggccacagca    60
agtaccatgg accatgccag gcatggcttc ctcccaaggc acagagacac gggcatcctt   120
gactccatcg ggcgcttctt tggcggtgac agggtgcgc caaagcgggg ctctggcaag    180
gactcacacc acccggcaag aactgctcac tatggctccc tgccccagaa gtcacacggc    240
cggacccaag atgaaaaccc cgtagtccac ttcttcaaga acattgtgac gcctcgcaca    300 ccaccccgt cgcagggaaa gggagagga ctgtccctga gcagatttag ctgggggcc     360 gaaggccaga gaccaggatt tggctacgga ggcagagcgt ccgactataa atcggctcac    420
aagggattca agggagtcga tgcccagggc acgctttcca aaattttta gctggggagga   480 agagatagtc gctctggatc acccatggct agacgctaa                          519
```

```
<210> SEQ ID NO 26
<211> LENGTH: 622
<212> TYPE: DNA
<213> ORGANISM: human

<400> SEQUENCE: 26
catatggcgt ctcagaaacg tccgtcccag cgtcacggct ccaaatacct ggccaccgcc    60
agcaccatgg accatgcccg tcatggcttc ctgccgcgtc accgtgacac cggcatcctg   120
gactccatcg gccgcttctt cggcggtgac cgtggtgcgc cgaaacgtgg ctctggcaaa    180
gtgccgtggc tgaaaccggg ccgtagcccg ctgccgtctc atgcccgtag ccagccgggc    240
ctgtgcaaca tgtacaaaga ctcccaccac ccggctcgta ccgcgcacta tggctccctg    300
ccgcagaaat cccacggccg tacccaggat gaaaacccgg tggtgcactt cttcaaaaac    360
attgtgaccc cgcgtacccc gccgccgtct cagggcaaag gccgtggcct gtccctgagc    420
cgtttcagct ggggcgccga aggccagcgt ccgggcttcg gttacggcgg ccgtgcgtcc    480
gactataaat ctgctcacaa aggcttcaaa ggcgtggatg cccagggtac cttgtccaaa    540
attttcaaac tgggcggccg tgatagccgt tctggctctc cgatggctag acgtcatcac    600
catcaccatc actaataagc tt                                             622
```

```
<210> SEQ ID NO 27
<211> LENGTH: 203
<212> TYPE: PRT
<213> ORGANISM: human

<400> SEQUENCE: 27

Met Ala Ser Gln Lys Arg Pro Ser Gln Arg His Gly Ser Lys Tyr Leu
```

-continued

```
1               5                   10                  15
Ala Thr Ala Ser Thr Met Asp His Ala Arg His Gly Phe Leu Pro Arg
            20                  25                  30
His Arg Asp Thr Gly Ile Leu Asp Ser Ile Gly Arg Phe Phe Gly Gly
            35                  40                  45
Asp Arg Gly Ala Pro Lys Arg Gly Ser Gly Lys Val Pro Trp Leu Lys
    50                  55                  60
Pro Gly Arg Ser Pro Leu Pro Ser His Ala Arg Ser Gln Pro Gly Leu
65                  70                  75                  80
Cys Asn Met Tyr Lys Asp Ser His His Pro Ala Arg Thr Ala His Tyr
                85                  90                  95
Gly Ser Leu Pro Gln Lys Ser His Gly Arg Thr Gln Asp Glu Asn Pro
            100                 105                 110
Val Val His Phe Phe Lys Asn Ile Val Thr Pro Arg Thr Pro Pro Pro
        115                 120                 125
Ser Gln Gly Lys Gly Arg Gly Leu Ser Leu Ser Arg Phe Ser Trp Gly
    130                 135                 140
Ala Glu Gly Gln Arg Pro Gly Phe Gly Tyr Gly Gly Arg Ala Ser Asp
145                 150                 155                 160
Tyr Lys Ser Ala His Lys Gly Phe Lys Gly Val Asp Ala Gln Gly Thr
                165                 170                 175
Leu Ser Lys Ile Phe Lys Leu Gly Gly Arg Asp Ser Arg Ser Gly Ser
                180                 185                 190
Pro Met Ala Arg Arg His His His His His His
            195                 200
23
```

MODIFIED MYELIN BASIC PROTEIN MOLECULES

FIELD OF THE INVENTION

The present invention relates to the treatment of autoimmune diseases. In particular, the invention provides compositions and methods facilitating the diagnosis and treatment of Multiple Sclerosis (MS). More particularly, engineered human Myelin Basic Protein (MBP) molecules, i.e., MBP polypeptides and nucleic acid molecules encoding MBP polypeptides, and methods for their use are provided.

BACKGROUND OF THE INVENTION

The discussion in this section is not limited to subject matter that qualifies as "prior art" against the present invention. Therefore, no admission of such prior art status shall be implied or inferred by reason of inclusion of particular subject matter in this discussion, and no declaration against the present inventors' interests shall be implied by reason of such inclusion.

Autoimmune Diseases

Autoimmune diseases result from the loss of tolerance to certain self antigens, resulting in an inappropriate attack by the immune system upon these antigens. Numerous mechanisms normally function to maintain immune self-tolerance in both the antibody-mediated (humoral) and cellular aspects of the immune system. It is when these mechanisms malfunction that autoimmune diseases occur.

Illnesses resulting from such misdirected immune system activity affect more than 10 million Americans. Therapies that treat the causes, rather than the symptoms of these diseases have long been sought. While various agents have been found that provide beneficial reductions in autoimmune activity, such treatments, in general, have the undesirable and dangerous effect of also compromising normal immune functions, and are thus considered sub optimal.

Multiple Sclerosis

Multiple Sclerosis (MS) is a progressive neurodegenerative autoimmune disorder affecting about 350,000 Americans. Females are twice as likely as males to develop the disease. MS usually affects patients who are between the ages of 15 and 50 years, most commonly young women between the ages of 20 and 40. MS derives its name from the multiple scarred (sclerotic) areas of degeneration visible on macroscopic examination of the central nervous system (CNS) of affected individuals. The degeneration associated with MS includes demyelination, chronic inflammation, and gliosis (scarring) of affected areas of the brain, optic nerve, and spinal cord.

MS is characterized by different types and stages of disease progression. Patients are diagnosed as having relapsing and remitting MS when they experience periods of exacerbations and remissions. Rapidly progressive or chronically progressive MS is diagnosed depending upon the pace of disease progression. These stages usually occur later in the course of the disease when the extent of recovery from individual attacks decreases and there are clinically stable periods between periods of deterioration. Inactive MS typically occurs late in disease progression and is characterized by fixed neurologic deficits of variable magnitude.

MS is always debilitating and may sometimes lead to paralysis and death. Although the factors triggering the initial onset of MS remain unknown, evidence is persuasive that MS pathology results from the autoimmune actions of certain white blood cells, especially neuroantigen-specific T cells.

Pathologically, MS is characterized by chronic inflammation, demyelination, and gliosis of white matter. The classic lesions of MS, termed plaques, are well-demarcated gray or pink areas easily distinguished from surrounding white matter. (The coloration of white matter is due to the high concentrations of myelin in this tissue.) The acute MS lesion is characterized by demyelination associated with tissue infiltration by mononuclear cells, predominantly T cells (both helper and cytotoxic) and macrophages, with B cells and plasma cells rarely being present. These inflammatory infiltrates appear to mediate the demyelination that is characteristic of the disease. Since activated T cells release cytokines that promote macrophage infiltration and activation, T cells are considered the primary mediators of pathogenic autoimmune attack in MS. More detailed discussions of T cells and myelin are found below under "T Cell Physiology," "T Cells and Autoimmune Pathogenesis," and "T Cells Target Defined Autoantigens in MS."

Current treatments for MS vary. Depending on the severity of disease and the response to treatment, a variety of options for drug therapy are available. Drugs used to treat MS include steroids such as prednisone and methylprednisolone, hormones such as adrenocorticotropic hormone (ACTH), antimetabolites such as azathioprine, alkylating agents such as cyclophosphamide, and T-cell inhibitory agents such as cyclosporine. The administration of any of these drugs is dangerous, as they all typically produce some level of generalized immunosuppression and leave the patient more prone to infection. Patients may also experience side effects such as nausea, hair loss, hypertension, and renal dysfunction when treated with such drugs. In addition, some of these drugs are carcinogenic.

New approaches to treating MS include interferon-beta therapy, which can lessen the frequency of MS attacks and slow disease progression. Other new approaches include administration of antigens involved in MS autoimmune responses, as discussed below.

Diagnosis of MS

MS is typically diagnosed based on medical history and physical examinations. No clinical signs or diagnostic tests are unique to MS. Diagnosis of a patient with a single, initial symptom commonly associated with MS cannot be definitive, although symptoms of relapsing and remitting disease increases the likelihood of an MS diagnosis. Two or more episodes of worsening each lasting 24 hours or occurring at least a month apart, or slow stepwise progression of signs and symptoms over at least six months are considered strong indications of MS. MRI findings implicating involvement in two or more areas of CNS white matter and evidence of systemic disease are also indicative of MS.

Currently, various laboratory tests are performed to confirm the diagnosis and assess the progression of the disease. Such tests include analysis of human cerebrospinal fluid (CSF) and blood for chemical and cellular signs of MS pathology.

CSF abnormalities associated with MS consist of mononuclear cell pleocytosis and the presence of autoreactive (typically myelin reactive) T cells, an elevation in the level of total Ig, and the presence of oligoclonal Ig, typically seen as two or more oligoclonal bands. In approximately 80 percent of patients, the CSF content of IgG is increased in the presence of a normal concentration of total protein. This results from the selective production of IgG within the CNS.

Oligoclonal banding of CSF IgG is detected by agarose gel electrophoresis techniques. Two or more oligoclonal bands are found in 75 to 90 percent of MS patients. The presence of oligoclonal banding correlates with an elevated total IgG level in MS. Other Ig abnormalities in MS CSF include free kappa or lambda light chains and elevated levels of other Ig isotypes including IgA.

Metabolites derived from myelin breakdown also may be detected in CSF. Elevated levels of MBP or its fragments may be detected, e.g., by radioimmunoassay, both in MS and in some patients with other neurologic diseases.

In addition to many of the pathologic signs described above for CSF, blood of MS patients may show increased levels of IgG synthesis, polymorphonuclear leukocytes, decreased serum $B_{12}$ levels, elevated erythrocyte sedimentation rate, and presence of autoantibodies or autoreactive T cells. As discussed below, the "reactive T cell index" is a particularly useful cellular finding for monitoring the clinical course of MS.

While these various indicators of MS disease are clinically useful, other means of following the course and extent of autoimmune activity in MS patients using relatively inexpensive and easily quantifiable tests, such as blood or cerebrospinal fluid tests (as opposed to expensive imaging techniques such as MRI) are needed.

T Cells, Antigen Presenting Cells, and T Cell Epitopes

As mentioned above, MS pathogenesis is believed to be mediated by the inappropriate actions of white blood cells (leukocytes), most importantly T cells. T cells are mononuclear white blood cells that provide many essential immune functions. The importance of T cells in human autoimmune diseases has been increasingly appreciated in the past decade. Studies using treatments that result in generalized immunosuppression have defined a critical role for a subset of T cells, known as $CD4^+$ or helper T cells, as primary regulators of all immune responses (both cellular and humoral) to protein or peptide antigens.

T cells mediate tissue injury by indirect and direct means. T cells of both $CD8^+$ (cytotoxic) and $CD4^+$ (helper) subsets secrete a variety of inflammatory cytokines that can damage tissues indirectly by activating various other types of white blood cells. Examples of such T cell effects include activation of antibody secreting B cells (stimulating humoral immune activity) and activation of macrophages, which can cause acute tissue damage and inflammation by releasing hydrolytic enzymes, reactive oxygen species, and additional pro-inflammatory cytokines. In addition to these indirect effects of T cell activity, direct tissue damage can be mediated by $CD8^+$ cytotoxic T cells attacking cells displaying target antigens.

One unique aspect of the physiology of T cells is the presence of membrane bound antibody-like binding structures called T cell receptors (TCRs) on their cell surfaces. Like antibodies, TCRs bind with high specificity to particular antigens. Like antibody-producing cells, which develop as multitudinous clones of cells, each clone producing antibodies with unique specificities, T cells develop as a vast number of distinct clones, and any particular T cell clone expresses a single type of TCR with a defined binding specificity. T cell clones with TCRs that bind specifically to self antigens are responsible for the development of autoimmune diseases.

In addition to being cell surface, rather than soluble molecules, TCRs differ from antibodies in the way they recognize antigens. While antibodies bind to antigens in various contexts (e.g., antigens that are native, denatured, soluble, or membrane bound), TCRs only bind to most antigens after the antigens have been broken down (processed) by certain cells known as antigen presenting cells (APCs) and the resulting peptides displayed (presented) on the cell surfaces of the APCs in association with class II or class I proteins of the major histocompatibility complex (MHC). The details of the mechanism by which antigen processing is carried out by APCs are poorly understood. There is consequently considerable uncertainty regarding the ability of APCs to process a given antigen in such a way as to produce and display a particular peptide unless that antigen has already been characterized in this respect.

One exception to the requirement that APCs process and present antigens in order for the antigens to stimulate T cells via their TCRs is the case of small peptide antigens. Such peptides can bind directly to MHC class I molecules on cell surfaces without being processed by APCs, and may then be "recognized" and bound by specific TCRs and thereby stimulate T cells.

Studies of the interactions of antibodies and TCRs with their specific antigens have shown that a particular polypeptide antigen typically comprises numerous submolecular features, known as epitopes, that each can serve as a distinct binding site for a particular antibody or (subsequent to APC processing of the polypeptide and MHC display of a derived peptide comprising the T cell epitope) a particular TCR.

Thus, TCRs and antibodies are similar in that each only recognizes a small portion of a polypeptide antigen. They differ in that an antibody typically recognizes its specific epitope within the context of the intact polypeptide, while a TCR only recognizes a specific epitope as an MHC class II or class I associated peptide fragment of a processed polypeptide on the surface of an APC. Importantly, this TCR epitope recognition process can only occur if an APC can process the polypeptide antigen so as to generate and display the appropriate peptide. Thus, even though a peptide that is recognized by a specific TCR may be present in a particular polypeptide antigen, it is uncertain whether peptides capable of stimulating T cells expressing that specific TCR will be derived from that polypeptide antigen in vivo. This is because it is uncertain whether APCs can generate the peptide recognized by the specific TCR by processing the particular polypeptide antigen.

This lack of certainty regarding the results of APC processing of a particular polypeptide antigen stems from several factors. One reason why an APC may not process a particular polypeptide antigen so as to display a specific peptide epitope contained within the polypeptide is that the APC efficiently cleaves the polypeptide at a site within the epitope and thereby destroys it. A second reason is that the polypeptide cannot enter into or be effectively broken down by the subcellular compartments of APCs responsible for polypeptide processing.

Certain aspects of the primary structure (linear amino acid sequence), secondary structure (3D structure resulting from interactions of amino acid residues that are close to one another in the linear amino acid sequence), or tertiary structure (3D structure resulting from interactions of amino acid residues that are far from one another in the linear amino acid sequence but come into proximity with each other as a result of folding of the polypeptide chain) can impact APC processing. The amino acid sequence of a polypeptide is clearly the most important factor in determining its potential to be processed and displayed by APCs so as to stimulate specific T cells. The peptide recognized by the specific T cell's TCRs must be contained within the amino acid sequence of the polypeptide. The amino acid sequence also determines the potential secondary and tertiary structure (i.e., the folding) of the polypeptide.

The folding of a polypeptide can also significantly impact APC processing. Both the first and second reasons given above for the uncertainty of the display by APCs of a specific epitope derived from a particular polypeptide can result from the way in which the polypeptide is folded. Proteolytic cleavage during processing within the APC can be influenced by the exposure or masking of a cleavage site due to folding. Entry of polypeptides into subcellular compartments is well known to be influenced by the 3D structure of the polypeptide, which structure is a function of folding.

T Cells and Autoimmune Diseases

In autoimmune diseases, only a limited number of T cell clones, reactive with various epitopes of a small number of autoantigens, become activated and are involved in pathogenesis. Various mechanisms have been postulated to play a role in this pathogenic activation of disease-causing autoreactive T cells. Primary activation of antigen presenting cells (APCs) by infection or local inflammation is implicated in one such mechanism. APCs activated in this way can then provide powerful co-stimulation for hitherto unreactive T cells.

Other proposed mechanisms involve the polyclonal activation of previously quiescent autoreactive T cells by superantigens, such as bacterial toxins; or a coincidental molecular mimicry between foreign and self antigens (Abbas et. al. 1994). In this last case, the host immune system mounts a response to an epitope on a protein expressed by a pathogen, such as a virus, that resembles a homologous epitope on a host protein. Autoimmune attack then results from the cross-reactive immune response that ensues. In addition to external factors, underlying the emergence of all T cell-mediated autoimmune disease is a complex pattern of inherited susceptibility determined by multigenic factors.

In several autoimmune diseases, including MS (as discussed in detail immediately below under "T Cells Target Defined Autoantigens in MS"), some or all of the autoantigens targeted by pathogenic T cells have been identified. Knowledge of these self antigens and the specific epitopes within these antigens that are targeted by autoreactive T cells in an autoimmune disorder such as MS provides an approach to therapy, as discussed in detail below under "Treatment of MS by Administration of Antigens" and "Therapeutic Induction of Apoptosis".

T Cells Target Defined Autoantigens in MS

Although, as discussed above, the precise etiology of MS remains unknown, autoimmune attack is clearly responsible for the destruction of central nervous system (CNS) myelin that is the hallmark of the disease. Myelin is the characteristic component of the myelin sheath that surrounds the axons of certain neurons, acts as an electrical insulator, and is essential for the proper signal transmission functions of these neurons. The demyelination associated with MS thus causes a loss of function in affected neurons, disrupting neuronal signaling and leading to paralysis and severe impairment of sensory functions.

The myelin sheath is made by oligodendrocytes (in the central nervous system) and Schwann cells (in the peripheral nervous system). Myelin is composed of regularly alternating layers of lipids (e.g., cholesterol, phospholipids, and sphingolipids) and proteins.

The four major protein components of myelin, i.e., myelin basic protein (MBP), proteolipid protein (PLP), myelin associated glycoprotein (MAG) and myelin oligodendrocyte protein (MOG), are recognized by autoreactive T lymphocytes isolated from MS patients (Martin et al. 1992; Kerlero de Rosbo et al. 1993).

Myelin basic protein (MBP) is a major protein component of myelin, comprising approximately 30% of the total protein content of the myelin sheath. MBP has been shown to be a major target autoantigen in MS, and T cells reactive with MBP play a key role in its pathogenesis (see, for example, Schwartz, R S, "Autoimmunity and Autoimmune Diseases" in Paul, Fundamental Immunology, 3rd Ed. Raven Press, New York, 1993, pp. 1033–1097; Brown and McFarlin 1981. *Lab Invest* 45, pp. 278–284; Lehmann et al. 1992. *Nature* 358, pp. 155–157; Martin et al. 1992. *Ann Rev Immunol* 10, pp. 153–187; Sprent 1994. *Cell* 76, pp. 315–322; Su and Sriram. 1991. *J of Neuroimmunol* 34, pp. 181–190; and Weimbs and Stoffel. 1992. *Biochemistry* 31, pp. 12289–12296).

MBP-specific T lymphocytes are found in the blood of MS patients. While they can sometimes be found in the blood of healthy individuals, they are typically present in the cerebrospinal fluid (CSF) of patients with MS. Significantly, such T cells are not found in CSF from healthy individuals (Kerlero de Rosbo et al. 1993; Zhang et al. 1994).

The immune responses of MS patients towards MBP clearly differ from those of healthy individuals. MBP reactive T cells are preferentially activated in MS patients, as demonstrated by the observation that the frequency of MBP-specific T cells expressing markers of activation (e.g., IL-2 receptors) is elevated in MS patients (see, for example, zhang, et al., 1994).

Gene mutation frequency analysis also provides evidence that MBP reactive T lymphocytes are specifically activated in MS patients. Since gene mutation is more frequent in dividing than in resting T cells, an increased mutation frequency in T cells of a particular specificity provides an indication of the specific activation of those cells in vivo (Allegretta et al. 1990).

T lymphocytes from MS patients were cultured in thioguanine to test the frequency of mutations in the hprt gene that would render them resistant to this purine analogue. A high frequency of thioguanine resistant T cell clones, up to 10 times the frequency of T cells from normal individuals, was found in MS patients, and a significant percentage of these mutant clones proliferated in response to brain MBP, although they had never been intentionally exposed to this antigen. In contrast, no resistant clones obtained from normal subjects recognized MBP.

MBP is also considered to be a primary autoantigen in MS because of its ability to induce experimental allergic encephalomyelitis (EAE) in animals. EAE is an experimentally induced condition that closely resembles MS and provides the only animal model of MS. In addition, transfer of T cells from an individual suffering from MS or EAE to a healthy animal can produce EAE in the recipient, a method of disease induction referred to as "adoptive transfer". For example, in human to animal transfer studies, CSF mononuclear cells (including T cells) from MS patients caused paralysis, ataxia, and inflammatory brain lesions when injected into the CSF in the brain ventricles of severe combined immunodeficiency (SCID) mice (Saeki et al. 1992). Also, immunization of animals with MBP can elicit the CNS inflammation, paralysis, and other signs and symptoms of EAE (see, for example, Martin et al. 1990, and Abbas et al. 1994).

Although it is clear that MBP is one of the primary antigens targeted by autoreactive T cells in MS, studies have revealed a marked heterogeneity of MBP epitopes that can induce T cell proliferative responses. These studies have not consistently revealed a single MBP epitope that is recognized with higher frequency by reactive T cells of MS patients than those of normal healthy individuals (Chou et al. 1989; Richert et al. 1989; Martin et al. 1990; Ota et al. 1990; Pette et al. 1990; Martin et al. 1992; Meinl et al. 1993).

Different molecular forms (isoforms) of MBP are generated by differential splicing of MBP hnRNAs, resulting in the presence in the encoded protein of some or all of the seven exons of the single MBP gene. In healthy adults, MBP is found almost exclusively as an 18.5 kDa molecule which is produced from an mRNA comprising all exons of the MBP gene except exon 2 (Kamholtz et al. 1988). Other forms of MBP include a full length (all 7 exons) 21.5 kDa isoform, and two other minor isoforms (17.2 and 20.2 kDa). The expression of the two exon 2 containing isoforms (21.5 kDa and 20.2 kDa) appears to increase with myelin formation, during both early fetal development and remyelination of damaged tissue (Kamholtz et al. 1988; Roth et al. 1987). These two isoforms are referred to in the art, and herein, as "fetal" isoforms, although they are also found in remyelinating damaged adult tissue.

MS plaques contain higher areas of remyelination and thus should contain higher levels of the 21.5 isoform of MBP than found in healthy adult CNS tissue, suggesting that an immune response to an epitope within the common 26 amino acid region (corresponding to the sequence spanning amino acid residue 60 to amino acid residue 85 of SEQ ID NO:1) of each of the two fetal isoforms of MBP coded for by exon 2 (which regions are referred to as "X2MBP" or simply "X2") could exacerbate the clinical course of established disease (Prineas et al. 1993; Raine and Wu, 1993; Bruck et al. 1994).

Since remyelination may occur cyclically in the course of MS, each cycle of remyelination could theoretically serve to drive an ongoing immune response by activating resting X2MBP specific T cells in the CNS. Supporting this hypothesis, several lines of evidence suggest the involvement of an epitope encoded by exon 2 of the MBP gene (i.e., an epitope within X2MBP) in MS pathogenesis.

Studies of the role of alternate isoforms of MBP in MS require the availability of quantities of purified myelin antigens in order to evaluate their immunological properties. Such studies have therefore generally have been limited to utilizing synthetically-derived peptides, e.g., peptides comprising X2MBP. Recently, CD4+ MHC class II-restricted T cells reactive with peptides containing exon 2 encoded sequences of human MBP were isolated from peripheral blood of both MS patients and normal healthy controls (Voskuhl et al., 1993a; Voskuhl et al. 1994). In a family afflicted with MS, the frequency of T lymphocytes specific for an X2 comprising peptide was higher than the frequency of T cells specific for epitopes within the 18.5 kDa isoform of MBP that does not contain X2 (Voskuhl et al., 1993b). In addition to this data from human subjects, a murine X2 comprising peptide was recently found to be immunogenic in SJL/J mice, and severe EAE was induced by adoptive transfer of exon 2 peptide-sensitized lymphocytes (Segal et al., 1994; Fritz and Zhao, 1994).

Taken together, these human and animal findings demonstrate that an in vivo cellular immune response to the myelin derived antigen MBP causes at least some of the pathogenesis associated with multiple sclerosis. It should be noted, however, that all of the studies regarding X2 epitopes used synthetic peptides as antigens and none of them used full length MBP 21.5 protein. In light of the uncertainty regarding processing and display of particular epitopes of untested proteins by APCs, it has been questioned in the art whether these results are truly relevant to in vivo MS pathogenesis.

Treatment of MS by Administration of Antigens

The ideal therapeutic treatment for any disease is one that specifically blocks pathogenesis without affecting normal physiology. In the case of autoimmune diseases, an approach to such ideal therapy is a treatment that specifically induces immune tolerance to autoimmune disease-associated self antigens without affecting immune responses to foreign antigens. New therapeutic agents and treatment strategies are being sought that will allow the induction of tolerance to specific autoantigens, while leaving all other aspects of immune function unaltered. Attempts have been made to therapeutically modify T cell responses via the administration of antigens to suppress specific autoreactive T cells and thereby elicit tolerance to disease-associated autoantigens. A distinct advantage of such antigen-specific therapy is that it can achieve the therapeutic modulation of the activities of only those T cells that, by reacting with the self antigens, are responsible for the development of pathology. This specificity provides therapeutic benefits without altering the important immune activities of T cells reactive with other antigens.

MS antigens have been studied as tolerization inducers for the treatment of MS/EAE, since therapies that suppress autoreactive T cells may significantly alleviate nervous tissue demyelination and resulting symptoms (see, for example, Adronni et al. 1993 and Critchfield et al. 1994). A number of treatment protocols and antigens have been used in these studies, with animal rather than human forms of the antigens predominantly being used. For example, Weiner et al. Science 1993, 259:1321–1324, used MBP purified from bovine myelin and Miller et al. 1992 used guinea pig, rat, and mouse MBPS. In studies using human antigen, MBP was purified from cadaveric human brain (See, for example, Zhang, et al. 1994).

Oral tolerance involves regulatory $CD8^+$ T cells that suppress immune responses both in vitro and in vivo through the secretion of cytokines, including TGF-beta (Chen et al. Science 1994, 265:1237–1240). The down-regulation of the activity of T cells mediated by this mechanism is not specific to particular T cell clones, and does not involve the production of antigen-specific suppressor factors, but acts on any T cells in close enough proximity to the suppressive T cells to be affected by their secreted cytokines.

Recent studies have investigated the tolerizing effects of oral administration of bovine myelin to MS patients (Weiner et al. 1993 Science 259:1321–1324; Yoon, 1993 Science 259:1263). While fewer of the patients treated with oral myelin developed exacerbations of their MS symptoms than the patients treated with placebo, the results of the study were inconclusive, as the patients were not properly randomized. In fact, the authors cautioned that "It must be strongly emphasized that this study does not demonstrate efficacy of oral myelin in the treatment of MS." Thus, while oral tolerization studies support the usefulness of myelin proteins as immunomodulatory agents for the treatment of MS, new, more effective antigens, and alternative modes of administration of such antigens for the immunomodulatory treatment of MS continue to be sought.

Clearly, for the treatment of human disease, human-derived antigens have advantages over animal-derived antigens, as they are the actual autoantigens targeted for autoimmune attack in human disease, and suppression of disease should be most effective when homologous protein is administered (Miller et al. 1992). In fact, it is known that immunodominant epitopes (i.e. the antigenic regions of the protein most often recognized by CD4[+] autoreactive T cells) of important MS autoantigens differ depending on the species from which the antigen is derived, even though many myelin antigens exhibit high interspecies homology at the amino acid sequence level. For example, as determined by analysis of T cells obtained from MS patients, an immunodominant epitope of human MBP is contained with the region spanning amino acids 84–102 and another is found in the region spanning amino acids 143–168. In contrast, a major immunodominant eptiope of murine MBP is found in the region spanning amino acids 1–9 (Zamvil et al. Nature 324:258, 1986) and a major immunodominant epitope of rat MBP is found in the region spanning amino acids 68–88 (Burns, et al. J. Ex. Med. 169:27, 1989).

The use of antigens isolated from human CNS tissue as therapeutic agents is, however, undesirable. This is due not only to problems associated with purifying antigens from CNS tissue generally and the difficulty of obtaining human raw materials, but, more importantly, to the problem of eliminating the possibility of pathogenic contamination. A particularly intractable problem is the purification of CNS-derived proteins so as to eliminate possible contamination with the prion particles that transmit the spongiform encephalopathies Creutzfeldt-Jakob disease and kuru. The prion particles are resistant to any known means of sterilization that will not also destroy the proteins being purified.

A useful approach to obtaining human antigens that avoids these problems is the production of protein antigens using recombinant DNA technology, typically by preparing DNA molecules encoding the antigens and using the DNAs to drive expression of the antigens in non-human host cells. Oettinger et al. (1993) have prepared a recombinant DNA molecule comprising unmodified human sequences encoding the 18.5 kDa form of human MBP and used this DNA to express recombinant human 18.5 kDa MBP in *Escherichia coli*.

T Cell Deletion

Alterations in the T cell repertoire occur naturally during T cell development. Only a small fraction of thymocytes (immature T cells) survive the development and selection events in the thymus that result in emigration of developing T cells to the peripheral circulation where they complete their maturation (von Boehmer, 1988; Marrack and Kappler, 1987). Experimental evidence strongly suggests that a large number of thymocytes that bear receptors for autoantigens are initially present in the thymus. During T cell development in the thymus, those cells reactive with self antigens are deleted (killed) as part of the normal developmental pathway. This intrathymic tolerization process is referred to as "thymic tolerance".

Developing T cells do not encounter certain autoantigens in the thymus, but may encounter them as mature peripheral T cells. Tolerance to such autoantigens is normally produced outside the thymus, and is referred to as "peripheral tolerance". Peripheral tolerance can occur by at least two mechanisms, one of which is a similar but distinct process to thymic tolerization that results in the deletion of those mature peripheral T cells that are specifically reactive with a previously unencountered autoantigen. In addition, T cells with certain specific reactivities can be induced to become inactive (anergic). Peripheral deletion and the induction of anergy are physiologic mechanisms that result in the development of "peripheral tolerance". As a result of thymic and peripheral tolerization, mature T cells are normally tolerant to most autoantigens.

The mechanism by which tolerization via T cell deletion is generated has recently been shown to depend upon repeated exposure to an antigen under certain defined conditions. Specific T cell deletion can therefore be induced by the appropriate administration of exogenous compounds comprising the relevant epitopes. As only a limited number of autoantigens (notably comprising a much greater number of epitopes) are involved in the pathogenesis of any individual autoimmune disease, it is possible, when they are known, to administer the self epitopes targeted in a disease to sufferers in the form of one or more isolated autoantigen-derived compounds containing the epitopes involved in pathogenesis.

Apoptosis

The deletion of autoreactive T cells is an example of programmed cell death, which represents an important process in the regulation of many biological systems. Programmed cell death occurs by a mechanism referred to as apoptosis, in which cells respond to certain stimuli by undergoing a specific sequence of predetermined events that effectively constitute cellular suicide. Apoptosis clearly plays a large role in shaping and maintaining the T cell repertoire and contributes to the establishment of self-tolerance by actively eliminating cells expressing autoreactive TCRs.

It has recently been discovered that T cells are sensitive to apoptotic cell death induced by a variety of stimuli at multiple points in their lifespan (see, for example, Lenardo 1991. *Nature* 353, pp. 858–860; Boehme and Lenardo 1993. *Eur J Immunol* 23, pp. 1552–1560; Critchfield et al. 1994. *Science* 263, pp. 1139–1143). Positive selection factors are also believed to play a role in regulating the survival of specific T cell clones. The reduction or expansion of the number of individual T cells of a particular clone in an organism by these and other mechanisms serve to modulate the responsiveness of the organism's immune system to a particular antigen. It is now firmly established in several autoimmune disease models, as well as in certain viral infections, that apoptosis can be induced (upon exposure to antigen under certain defined conditions) in mature peripheral antigen-specific T lymphocytes as well as in immature thymocytes.

Apoptosis occurs in many biological systems (see, for example, Kerr et al. 1991; Lockshin and Zakeri, 1991; Cohen et al. 1992; Duvall and Wyllie, 1986; Cotter et al. 1990). A cell undergoing apoptosis undergoes a specific program of events—cellular and biochemical processes that depend upon active metabolism and contribute to the cell's self-destruction. In apoptotic T cells, the nucleus shrinks, the chromatin condenses, the genetic material (DNA) progressively degrades into small (nucleosomal repeat sized) fragments, there is cytoplasmic compaction, the cell membrane forms blebs, and the cell eventually collapses (Kawabe and Ochi, 1991; Smith et al. 1989). Cells cannot recover from apoptosis, it results in irreversible cell death (Kawabe and Ochi, 1991; Smith et al. 1989).

Recent reports have indicated a role for the TNF-related cytokine known as the FAS ligand and its receptor, CD95 (the FAS receptor), in the induction of apoptosis in T cells (Strasser, Nature 1995, 373:385; Dhein et al., Nature 1995, 373:438; Brunner et al., Nature 1995, 373:441; and Ju et al., Nature 1995, 373:444).

T cells that do not undergo apoptosis, but which have become activated, will carry out their "effector" functions by causing cytolysis, or by secreting lymphokines that cause B cell responses or other immune effects (Paul, 1989). These effector functions are the cause of tissue damage in autoimmune and other diseases.

Therapeutic Induction of Apoptosis

A powerful approach to avoiding or treating autoimmune diseases is to permanently eliminate by apoptosis only those T cells reactive with autoantigens targeted in the particular autoimmune disease being treated, while leaving the vast majority of the T cell repertoire intact. In vivo studies have demonstrated that EAE can be treated by administration of myelin antigens at a dose and interval effective to induce apoptosis of T cells reactive with the antigens (se, for example, Critchfield et al. 1994. Science 263, pp. 1139–1143).

This approach is described in U.S. patent application Ser. No. 07/751,090, which was abandoned in favor of continuing U.S. patent application Ser. No. 08/122,345, which issued as U.S. Pat. No. 6,083,503 in the name of Michael J. Lenardo, and entitled Interleukin-2 Stimulated T Lymphocyte Cell Death for the Treatment of Autoimmune Diseases, Allergic Responses, and Graft Rejection, and U.S. patent application Ser. No. 07/926,290, which was abandoned in favor of continuing U.S. patent application Ser. No. 08/348,286, which issued as U.S. Pat. No. 5,935,575, in the name of Michael J. Lenardo, and entitled Interleukin-4 Stimulated T Lymphocyte Cell Death for the Treatment of Allergic Disorders.

The accompanying figures, which are incorporated in and constitute part of the specification, illustrate certain aspects of the invention, and together with the description, serve to explain the principles of the invention. It is to be understood, of course, that both the figures and the description are explanatory only and are not restrictive of the invention.

BRIEF DESCRIPTION OF THE DRAWINGS

FIG. 11. Sequence comparison of recombinant human MBP+X2$^{Cys81/bact.}$ (fetal form, "f", SEQ ID NO: 26) to that of Adult brain-derived human MBP (adult form "a") and the encoded polypeptide (SEQ ID NO. 27). The adult brain-derived human MBP sequence (Genbank accession #M13577) is noted only in positions that deviate from the *E. coli* preferred codon sequence of MBP+X2$^{Cys81/bact.}$. The initiator (ATG) and stop codons (TAA) are indicated for both genes. Dashes in the adult brain-derived human MBP sequence reflect the positions of exon 2 (bp 177–255) and the histidine tag (bp 595–612) additions to this version of MBP+X2$^{Cys81/bact.}$ (i.e., MBP+X2$^{Cys81/bact.}$ with 6 carboxy terminal histidine residues, also referred to as a histidine tag). Regions of overlap between synthetic oligonucleotides used for the construction of the MBP+X2$^{Cys81/bact.}$ gene are underlined. C to T bp mutations from the intended MBP+X2$^{Cys81/bact.}$ gene sequence are noted by asterisks above positions 462, 528 and 532. These changes conserve the MBP+X2$^{Cys81}$ amino acid sequence. Sense oligonucleotide 1 (SEQ ID NO:5) includes the sequence GGAATTCCG-TAAGGAGGTAT AG (not shown in this figure) located 5' to the NdeI cloning site, and extends through base 108. Oligonucleotide 6 (bp 516–622, SEQ ID NO:10) is an antisense oligonucleotide to the sequence shown and includes the tetranucleotide CCCC (not shown in this figure) located 3' to the HindIII site. Four other oligonucleotides used include sense oligonucleotides 3 (SEQ ID NO:7) and 5 (SEQ ID NO:9) and antisense oligonucleotides 2 (SEQ ID NO:6) and 4 (SEQ ID NO:8). The cysteine at amino acid 81 is noted in bold face type.

FIG. 13. Details of the specific molecules tested and results obtained with each T cell line shown in FIG. 12.

SUMMARY OF THE INVENTION

Figure 1:
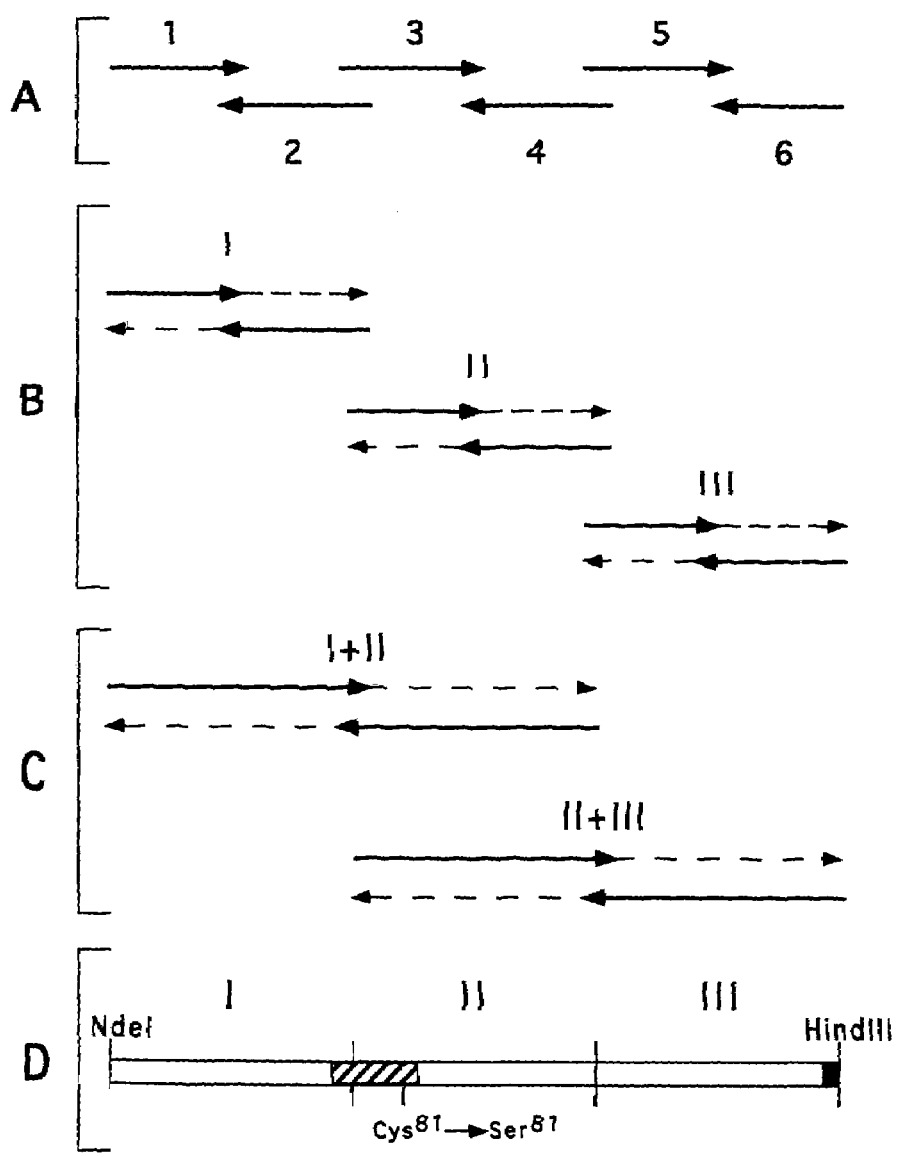
FIG. 1. PCR strategy for construction of a synthetic MBP21.5 gene (cDNA). Indicated by bracket A is the alignment of overlapping oligonucleotides 1 through 6 (SEQ ID NO:5, SEQ ID NO:6, SEQ ID NO:7, SEQ ID NO:8, SEQ ID NO:9, and SEQ ID NO:10) that were used to construct the MBP+X2$^{Cys81/Bact.}$ gene. Three subdomains of the gene (I, II, and III as shown by the diagram indicated by bracket B) were initially synthesized. Larger domains (I+II, II+III) were formed by overlapping PCR using the appropriate outside oligonucleotides (oligonucleotides 1 and 4, and oligonucleotides 3 and 6, respectively) as shown by the diagram indicated by bracket C. The full-length molecule was completed by overlapping-PCR of domains I+II and II+III using outside oligonucleotides 1 and 6. A map of the final product is shown by the diagram indicated by bracket D. In this diagram, the hatched region in this map of the full-length molecule depicts the location of exon 2, with the cysteine at amino acid residue 81 ($Cys^{81}$) shown as altered to serine ($Ser^{81}$). The dark box at the 3' end of the gene (right hand side of the diagram) illustrates the addition of sequences encoding the histidine tag that was added to facilitate purification.

Accordingly, it is an object of the present invention to provide compositions and methods for the diagnosis, clinical assessment, and therapeutic treatment of MS in human patients, and for the assessment of the potential responsiveness of MS patients to such therapeutic treatment. The polypeptide and nucleic acid molecules of the invention comprise MBP sequences, i.e., sequences corresponding to any span of at least 10 contiguous amino acid residues of SEQ ID NO: 1 or SEQ ID NO:3. As used herein and in the claims, an "MBP polypeptide" is a polypeptide comprising such an MBP sequence, and "an amino acid sequence encoded by at least part of exon 2 of the human MBP gene" is a sequence of at least 10 contiguous amino acids corresponding to at least 10 contiguous amino acids from the region spanning amino acids 60–85 of SEQ ID NO:1.

The invention provides compositions comprising novel recombinant human MBP 21.5 polypeptides (i.e., MBP polypeptides that comprise an amino acid sequence encoded by at least part of exon 2 of the human MBP gene). Preferably, these MBP polypeptides include amino acid sequences encoded by all seven exons of the human MBP gene. In certain preferred embodiments, the sequence encoded by exon 2 is modified to facilitate large scale production and purification of the polypeptide. Also provided are DNA constructs which encode MBP 21.5 polypeptides and which have been engineered to optimize the production and isolation of such molecules from bacterial cells.

The methods of the invention comprise the use of the compositions of the invention in the diagnosis and clinical assessment of MS, as well as in the therapeutic treatment of MS and in the assessment of the potential responsiveness of MS patients to such therapeutic treatment.

DESCRIPTION OF THE PREFERRED EMBODIMENTS

As discussed above, the present invention relates to MBP 21.5 polypeptides (proteins) for use in the treatment, diagnosis, and clinical assessment of MS, and to nucleic acid molecules useful in producing MBP 21.5 polypeptides.

As used in this specification and in the claims "MBP 21.5 polypeptides" refers to one or more of the following polypeptides: the polypeptide of SEQ ID NO:1 (human 21.5 kDa MBP, "MBP+X2"), the polypeptide of SEQ ID NO:1 with amino acid 81 being any standard amino acid ("MBP+X2$^{Xxx81}$"), the polypeptide of SEQ ID NO:1 with cysteine 81 replaced with any other standard amino acid ("MBP+X2$^{Xaa81}$"), the polypeptide of SEQ ID NO:1 with cysteine 81 replaced with an uncharged amino acid (i.e., an amino acid that is uncharged at a pH of between 6 and 7) having a molecular weight of less than about 150 ("MBP+ X2$^{Xaa81<150}$"), and the polypeptide of SEQ ID NO:1 with cysteine 81 replaced with serine ("MBP+X2$^{Ser81}$").

"MBP 21.5 polypeptides" also comprise variations of the foregoing four sequences, provided that the sequence continues to include at least some of the sequence of amino acids encoded by exon 2 of the human MBP gene, and further provided that the polypeptide can induce a "T cell response" in a population of MBP reactive T cells isolated from an MS patient. The term "T cell response" is discussed below.

I. MBP 21.5 Polypeptides

A preferred MBP 21.5 polypeptide of the invention is a bacterially expressed human recombinant MBP containing amino acids encoded by exon 2 of the human MBP gene and having a molecular weight of approximately 21.5 kDa in which Cys 81 has been replaced with another standard amino acid (this polypeptide is referred to herein as "MBP+ X2$^{Xaa81}$", and nucleic acid molecules encoding it are referred to as "MBP+X2$^{Xaa81/hum.}$" or "MBP+X2$^{Xaa81/bact.}$" with the superscript $^{hum.}$ or $^{bact.}$ indicating the codon usage in the coding region of the nucleic acid molecule, as discussed below). As used in the art, a "standard" amino acid is one of the 20 amino acids commonly found in proteins.

As used herein, the amino acid sequence encoded by exon 2 will be referred to as X2MBP or simply X2. In accordance with the invention, the X2MBP sequence may be located at any position in the MBPX+X2$^{Xxx81}$ polypeptide, although the naturally occurring position of the native exon 2 encoded sequence (as shown in SEQ ID NO:1, SEQ ID NO:2, and SEQ ID NO:3) is preferred. Other polypeptides comprising X2MBP sequences are described in copending U.S. patent application Ser. No. 08/431,648 filed concurrently herewith in the names of John P. Mueller, Michael J. Lenardo, Louis A. Matis, Eileen Elliott Mueller, Steven H. Nye, Clara M. Pelfrey, Stephen P. Squinto, and James A. Wilkins, and entitled "Modified Proteolipid Protein Molecules", which is incorporated herein by reference.

Preferably, the replacement amino acid does not cause epitope conversion, i.e., T cell recognition of the immunodominant epitope or epitopes of X2MBP is substantially unaltered by the replacement of Cys 81 with the particular replacement amino acid. Prior to the present invention it was unknown whether replacement of amino acid residue 81 with another standard amino acid would cause such epitope conversion (i.e., whether such alterations would be epitope neutral).

Lack of epitope conversion by the substitution of any standard amino acid can be determined in accordance with the present invention by testing the responses of T cells (e.g., T cell lines) specifically reactive with X2MBP (X2MBP-specific T cells) to MBP+X2$^{Xaa81}$ or, preferably, to a test peptide (the X2$^{Xaa81}$ peptide) comprising the exon 2 encoded region of MBP+X2$^{Xaa81}$ as described in detail below. The test peptide is preferably a 26 amino acid peptide with a sequence corresponding to amino acid residues 59 to 84 of SEQ ID NO:1 with Cys 81 replaced with the other standard amino acid (the "X2$^{Xaa81}$ 26mer").

X2MBP-specific T cells can be obtained as T cell lines by conventional methods using a peptide containing the amino acid sequence encoded by exon 2 (hereinafter referred to as an "X2MBP peptide"). For example, the methods described by Voskuhl et al. 1993a may be used. See also Voskuhl et al., 1993b; Segal et al., 1994; Voskuhl et al., 1994; and Fritz and Zhao, 1994.

Preferably human T cell lines are obtained by such standard methods following stimulation with an X2MBP peptide that has just the 26 amino acids encoded by exon 2, i.e., an X2MBP peptide whose a sequence corresponds to amino acid residues 59 to 84 of SEQ ID NO:1 (the "X2 26mer"). In particular, stimulation with the X2 26mer is preferred to stimulation with the 40 amino acid X2MBP peptide or the 18.5 kDa isoform of MBP described in the Voskuhl et al. 1993a publication.

In accordance with the present invention, X2MBP-specific T cell lines thus obtained are used, inter alia, to determine the epitope neutrality of a particular amino acid substitution at position 81. This is accomplished by assessing the reaction of the cells of the X2MBP-specific human T cell line to the X2$^{Xaa81}$ peptide. (MBP+X2$^{Xaa81}$ can also be used to test epitope neutrality, but this is less preferred.) If the X2MBP-specific T cells respond to the X2$^{Xaa81}$ peptide containing the particular amino acid substitution to an extent that satisfies the criterion for X2MBP-specificity set forth by Voskuhl et al. 1993a, i.e. if the particular X2$^{Xaa81}$ peptide demonstrates a stimulation index of greater than 2, as compared to medium alone controls, then epitope neutrality of a particular replacement amino acid is confirmed. Preferably the stimulation index is greater than 3.

In accordance with the present invention, such an epitope neutral replacement can generally be achieved using an uncharged amino acid that has a molecular weight of less than about 150 and that preferably is not strongly hydrophobic.

Amino acids that satisfy these requirements include Ala, Asn, Gly, Pro, Thr, and Ser. Most preferably, the replacement is Ser, resulting in an MBP 21.5 polypeptide comprising an exon 2 encoded region in which Cys 81 has been changed to Ser 81 (hereinafter this polypeptide is referred to as "MBP+X2$^{Ser81}$", and nucleic acid molecules encoding it are referred to as "MBP+X2$^{Ser81/hum.}$" or "MBP+X2$^{Ser81/bact.}$", with the superscripts $^{hum.}$ and $^{bact.}$ indicating the codon usage in the coding region of the nucleic acid molecule, as discussed below).

Prior to the present invention, it was not known whether bacterially expressed MBP+X2 polypeptides would be recognized and responded to by T cells to the same extent as mammalian expressed MBP polypeptides (e.g., human derived MBP–X2). This uncertainty was due, inter alia, to the differences in protein folding during the expression of proteins in bacteria or mammalian cells. Bacterially expressed proteins are typically not folded into the native conformation of proteins expressed in mammalian cells. As discussed within the Background of the Invention section above under the heading "T Cells, Antigen Presenting Cells, and T Cell Epitopes", protein folding can determine whether a specific epitope is appropriately processed by APCs. For this reason, bacterially expressed proteins may not be processed and presented by APCs in the same manner as native proteins, and may therefore not be recognized by T cells.

The exon 2 sequences in MBP+X2$^{Cys81}$ were cause for additional uncertainty, as such sequences had only been shown to stimulate T cells when added to T cells as synthetic peptides, (which do not have to be processed by APCs in order to be recognized by TCRs and responded to by T cells). Prior to the present invention, it had never been shown that the 21.5 kDa isoform of MBP (regardless of source) could be correctly processed by APCs so as to stimulate encephalitogenic T cells, a question of particular interest with regard to the role of X2 epitopes in MS pathogenesis. The present invention has allowed the demonstration that this is the case, demonstrating the clinical relevance of the previously reported X2MBP peptide work.

II. Nucleic Acid Molecules Encoding MBP 21.5 Polypeptides

Nucleic acid molecules useful in the practice of the present invention can be prepared using a variety of techniques now known or subsequently developed in the art. For example, using techniques well known in the art they can be produced using cloned genes. The terms gene and genes, as used herein, encompass expressed (e.g., protein-encoding) nucleic acid molecules, either with intron-comprising sequences or without introns, e.g. cDNAs. The cloned genes are manipulated by conventional techniques, e.g., PCR amplification and/or restriction digestion of nucleic acid molecules of to generate restriction fragments encoding portions of the MBP 21.5 polypeptides. These fragments can be assembled using, for example, PCR fusion or enzymatic ligation of the restriction digestion products. The assembled constructions or fragments thereof can be modified by mutagenic techniques such as oligonucleotide mediated site-directed mutagenesis.

Numerous publications are available that teach these conventional methods, including Sambrook, et al. 1989; Ho et al. Gene 1989 77:51–59; Ausubel et al. 1994, *Current Protocols in Molecular Biology*, Wiley Interscience, John Wiley and Sons, New York. Alternatively, the nucleic acid molecules encoding the MBP 21.5 polypeptides used in the practice of the invention or any or all of the nucleic acid fragments used to assemble such nucleic acid molecules can be synthesized by chemical means (see, for example, Talib et al. 1991 and Ausubel et al. 1994).

SEQ ID NO:1 sets forth the amino acid and nucleotide sequences for the native human 21.5 kDa fetal isoform of MBP. A nucleic acid molecule encoding MBP+X2$^{Xaa81}$ can be produced by modifying at least one of nucleotides 241 through 243 (i.e., codon 81) of SEQ ID NO:23 so that the codon corresponds to the desired replacement amino acid. Such modification can be achieved using a variety of nucleic acid manipulation techniques now known or subsequently developed in the art, including conventional recombinant DNA techniques such as oligonucleotide mediated site-directed mutagenesis, PCR mutagenesis, or de novo synthesis of the desired polynucleotide, as discussed above.

For MBP+X2$^{Ser81}$, the native TGC codon can be changed to any of AGC, AGT, TCA, TCC, TCG, and TCT. In general, the change is preferably to TCG, as this change results in the creation of a new TCGA restriction site at this location. The creation of a new restriction site at this location facilitates the identification and separation of a nucleic acid molecule comprising the desired modification from the mixture of modified and unmodified nucleic acid molecules that is typically obtained as an intermediate step in the overall process of producing a nucleic acid molecule encoding MBP+X2$^{Xaa81}$, such as a nucleic acid molecule encoding MBP+X2$^{Ser81}$. When considerations of optimization of protein production override considerations of ease of nucleic acid manipulation, and when MBP+X2$^{Ser81}$ is to be produced in bacteria, e.g., *E. coli* (where the TCG codon is not a bacterially preferred codon) the change is preferably to TCC, TCT, or AGC, since these codons are preferred in bacteria.

SEQ ID NO:2 sets forth the amino acid sequence for the native human 21.5 kDa fetal isoform of MBP and SEQ ID NO: 23 sets forth a modified nucleotide sequence encoding this protein wherein the codons for various of the amino acids have been "bacterialyzed" to enhance the production of the protein in bacteria. As known in the art, bacteria tend to use certain codons for particular amino acids in preference to other possible codons which encode the same amino acid. Accordingly, it is believed that the protein synthetic machinery of the bacteria may work more effectively when processing the preferred codons. However, as also known in the art, it is unpredictable whether substituting preferred codons for non-preferred codons will in fact result in a substantial enhancement in production of a particular protein in bacteria. As discussed in detail in the Examples, below, the bacterialization of SEQ ID NO:23 increased production of MBP in *E. coli* by at least 50 percent.

In SEQ ID NO:2, the bacterialization has been performed by substituting bacterially preferred codons for native human codons which did not already correspond to bacterially preferred codons (criterion 1). In selecting which codons to change, particular attention was paid to the following seven amino acids: Arg (17 of 21 codons changed); Gly (13 of 28 codons changed); Pro (10 of 17 codons changed); Lys (12 of 14 codons changed); Leu (3 of 11 codons changed); Thr (6 of 8 codons changed); and Val (3 of 5 codons changed). These amino acids were emphasized because of a strong bias for the use of certain of their redundant codons in *E. coli*. (Wada et al., 1992.). Of these seven, Arg, Pro, and Lys were considered the most important since they constitute 26% of the amino acid residues in MBP 21.5. As an alternate criterion, some codons were changed to a codon which is preferentially used in highly expressed bacterial genes (criterion 2, see Grosjean and Fiers, 1982). A complete listing of codon changes incorporated in the nucleic acid molecule corresponding to SEQ ID NO:3 (except for the native cysteine codon 81 being retained in this comparison instead of the Ser codon for amino acid number 81 found in SEQ ID NO:3) is given in Table 1, where the native (fetal) human MBP21.5 sequence data are indicated as "huMBP 21.5" and the bacterialized recombinant MBP (MBP+X2$^{Cys81/bact.}$) sequence data are indicated as "recMBP 21.5".

As used herein and in the claims, the expression "bacterially preferred codon" refers to a codon selected on the basis of either of the above two criteria, and the superscripts (1) "$^{hum.}$" and (2) "$^{bact.}$" designate MBP-encoding nucleic acid sequences with (1) native human codons and (2) at least some codons that have been changed from native human codons to bacterially preferred codons.

More or less bacterialization can be performed if desired, the criterion being whether a desired level of production increase is achieved. Also, the bacterialyzed sequence can be further altered to produce MBP+X2$^{Xaa81/bact.}$, or preferably MBP+X2$^{Ser81/bact.}$. The bacterialization and the further alterations at codon 81 can be performed using the nucleic acid manipulation techniques discussed above and in the Examples.

As discussed above, SEQ ID NO:3 shows such a bacterialyzed nucleotide sequence encoding MBP+X2$^{Ser81}$, and further comprising an additional 18 nucleotide sequence at the 3' end (immediately preceding the termination codon, i.e., nucleotides 592–609 of SEQ ID NO:3) that encodes six histidine residues at the carboxy terminus of the encoded polypeptide (such a multiple histidine addition of at least four residues being referred to as a histidine tag). This histidine tag is not found in the native MBP+X2$^{Cys81/hum.}$ protein, and has been added to facilitate purification of the polypeptide product of the expression of this MBP+X2$^{Ser81/bact.}$ gene.

Histidine tags act as metal chelators and allow the use of metal chelation chromatography or the like to rapidly and efficiently purify polypeptides containing such tags from mixtures of proteins. In accordance with the invention, such a histidine tag may be added to any of the polypeptides of the invention, or a sequence encoding such a tag may be added to any of the nucleic acid molecules of the invention so as to allow the ready purification of the polypeptides of the invention.

The protein encoding nucleic acid molecules of the invention can be inserted into an appropriate expression vector, i.e., a vector that contains the necessary elements for the transcription and translation of the inserted protein-encoding sequence, and then used to produce MBP 21.5 polypeptides. A variety of host vector systems may be utilized to express the protein encoding sequence. These include, but are not limited to, mammalian cell systems infected with a virus such as vaccinia virus, adenovirus, a retrovirus, etc.; mammalian cell systems transfected with plasmids; insect cell systems infected with a virus such as baculovirus; microorganisms such as yeast containing yeast expression vectors, or bacteria transformed with bacteriophage DNA, plasmid DNA, cosmid DNA, or the like.

Useful expression vectors for bacterial use can comprise a selectable marker and bacterial origin of replication derived from commercially available plasmids including those comprising genetic elements of the well-known cloning vector pBR322 (American Type Culture Collection, 12301 Parklawn Drive, Rockville, Md. 20852, United States of America; ATCC Accession No. 37017). These pBR322 "backbone sections," or functionally equivalent sequences, are combined with an appropriate promoter and the structural gene to be expressed.

Preferred bacterial expression vectors include, but are not limited to, the phage T7 promoter plasmids pET14b, and pET22b (Novagen, Madison, Wis.). These vectors are preferably expressed in *E. coli* BL21(DE3) (Novagen, Madison, Wis.). This strain is lysogenic for a recombinant bacteriophage DE3 lysogen, which contains the gene for T7 polymerase behind the *E. coli* lacUV5 promoter (Studier et al., 1990). Other preferred bacterial expression vectors are Trc vectors including the pET Trc SO5/NI vector (SEQ ID NO:21) the pTrc 99A vector (Pharmacia) and the pSE vectors (Invitrogen, San Diego, Calif.).

Other promoters commonly used in recombinant microbial expression vectors include, but are not limited to, the lactose promoter system (Chang, et al., 1978, *Nature* 275: 615), the tryptophan (trp) promoter (Goeddel, et al., 1980, *Nucl Acids Res* 8, pp. 4057) and the tac promoter, or a fusion between the tac and trp promoters referred to as the trc promoter (Sambrook, et al., supra). Particularly preferred promoters are bacteriophage promoters, e.g., the T7 promoter discussed above, that can be used in conjunction with the expression of the corresponding bacteriophage RNA polymerase, e.g., T7 RNA polymerase, in the host cell.

Recombinant MBP 21.5 polypeptides may also be expressed in fungal hosts, preferably yeast of the genus *Saccharomyces* such as *S. cerevisiae*. Fungi of other genera such as *Aspergillus, Pichia* or *Kluyveromyces* may also be employed. Fungal vectors will generally contain an origin of replication from the 2 μm yeast plasmid or another autonomously replicating sequence (ARS), a promoter, DNA encoding the MBP 21.5 polypeptide, sequences directing polyadenylation and transcription termination, and a selectable marker gene. Preferably, fungal vectors will include origins of replication and selectable markers permitting transformation of both *E. coli* and fungi.

Suitable promoter systems in fungi include the promoters for metallothionein, 3-phosphoglycerate kinase, or other glycolytic enzymes such as enolase, hexokinase, pyruvate kinase, and glucokinase, as well as the glucose-repressible alcohol dehydrogenase promoter (ADH2), the constitutive promoter from the alcohol dehydrogenase gene, ADH1, and others. See, for example, Schena, et al. 1991, *Meth Enzymol* 194, pp. 389–398. Secretion signals, such as those directing the secretion of yeast alpha-factor or yeast invertase, can be incorporated into the fungal vector to promote secretion of the MBP 21.5 polypeptide into the fungal growth medium. See Moir, et al., 1991, *Meth Enzymol* 194, pp. 491–507.

Preferred fungal expression vectors can be constructed using DNA sequences from pBR322 for selection and replication in bacteria, and fungal DNA sequences, including the ADH1 promoter and the alcohol dehydrogenase ADH1 termination sequence, as found in vector pAAH5 (Ammerer, 1983, *Meth Enzymol* 101:192).

Various mammalian or insect cell culture systems can be employed to express the recombinant MBP 21.5 polypeptides of the invention. Suitable baculovirus systems for production of heterologous proteins in insect cells are reviewed by Luckow, et al., 1988, *Bio/Technology* 6, pp. 47. Examples of suitable mammalian host cell lines include the COS cell of monkey kidney origin, mouse C127 mammary epithelial cells, mouse Balb/3T3 cells, mouse MOP8 cells, Chinese hamster ovary cells (CHO), HeLa, myeloma, and baby hamster kidney (BHK) cells. Mammalian expression vectors may comprise non-transcribed elements such as an origin of replication, a suitable promoter and an enhancer linked to the MBP encoding sequence to be expressed, and other 5' or 3' flanking sequences such as ribosome binding sites, polyadenylation sequences, splice donor and acceptor sites, and transcriptional termination sequences.

The transcriptional and translational control sequences in mammalian expression vector systems to be used in transforming vertebrate cells may be provided by viral sources. For example, commonly used promoters and enhancers are derived from Polyoma virus, Adenovirus, Simian Virus 40 (Sv40), and human cytomegalovirus (CMV), including the cytomegalovirus immediate-early gene 1 promoter and enhancer.

Particularly preferred eukaryotic vectors for the expression of recombinant MBP polypeptides are pAPEX-1 (SEQ ID NO:11 and, more preferably, pAPEX-3p, SEQ ID NO:12. The vector pAPEX-1 is a derivative of the vector pcDNAI/ Amp (Invitrogen) which was modified to increase protein expression levels. First, the 3'-untranslated Sv40 small-t antigen intron was removed by deletion of a 601 base pair XbaI/HpaI fragment since this intron is susceptible to aberrant splicing into upstream coding regions (Evans and Scarpulla, 1989 Gene 84:135; Huang and Gorman, 1990, Molec. Cell Biol. 10:1805). Second, a chimeric adenovirus-immunoglobulin hybrid intron was introduced into the 5'-untranslated region by replacing a 484 base pair NdeI-NotI fragment with a corresponding 845 base pair NdeI-NotI fragment from the vector pRc/CMV7SB (Sato et al., 1994, J. Biol. Chem. 269:17267). Finally, to increase plasmid DNA yields from *E. coli*, the resulting CMV promoter expression cassette was shuttled into the vector pGEM-4Z (Promega Corp. Madison, Wis.).

The vector pAPEX-3 is a derivative of the vector pDR2 (Clontech Laboratories, Inc. Palo Alto, Calif.) in which the EBNA gene was first removed by deletion of a 2.4 kb ClaI/AccI fragment. The RSV promoter was then replaced with the CMV promoter and the adenovirus/immunoglobulin chimeric intron by exchanging a 450 bp MluI/BamHI fragment from pDR2 with a 1.0 kb MluI/BamHI fragment from the vector pAPEX-1. For construction of pAPEX-3P, a 1.7 kb BstBI/SwaI fragment containing the HSV tk promoter and hygromycin phosphotransferase (hyg) gene was removed from pAPEX-3 and replaced with a 1.1 kb SnaBI/NheI fragment containing the SV40 early promoter and puromycin acetyltransferase (pac) gene (Morgenstern and Land, 1990, Nucleic Acids Res. 18:3587–3596) plus a 137 bp XbaI/ClaI fragment containing an SV40 polyadenylation signal from the vector pAPEX-1.

A particularly preferred host cell for the expression of recombinant MBP-encoding inserts in the PAPEX vectors is the human 293 EBNA cell line (Invitrogen, San Diego, Calif.).

Another preferred eukaryotic vector for the expression of recombinant MBPs is pcDNAI/Amp (Invitrogen Corporation, San Diego, Calif.). The pcDNAI/Amp expression vector contains the human cytomegalovirus immediate-early gene I promoter and enhancer elements, the Simian Virus 40 (SV40) consensus intron donor and acceptor splice sequences, and the SV40 consensus polyadenylation signal. This vector also contains an SV40 origin of replication that allows for episomal amplification in cells (e.g., Cos cells, MOP8 cells, etc.) transformed with SV40 large T antigen, and an ampicillin resistance gene for propagation and selection in bacterial hosts.

Purified recombinant MBPs are prepared by culturing suitable host/vector systems to express the recombinant MBP translation products of the nucleic acid molecules of the present invention, which are then purified from the culture media or cell extracts of the host system, e.g., the bacteria, insect cells, fungal, or mammalian cells. Fermentation of cells that express recombinant MBP proteins containing a histidine tag sequence (a sequence comprising a stretch of at least 5 histidine residues) as a secreted product greatly simplifies purification. Such a histidine tag sequence enables binding under specific conditions to metals such as nickel, and thereby to nickel (or other metal) columns for purification.

Purified MBP 21.5 polypeptides are prepared by culturing suitable host/vector systems to express the recombinant translation products of the DNA compositions of the invention, which are then purified from the cells, cell extracts, culture media, or the like, of the host system, e.g., the bacterial, fungal, insect, or mammalian cells.

In general terms, the purification is performed using a suitable set of concentration and fractionation (e.g., chromatography) steps. A particularly preferred purification step involves acid extraction, as described in the examples, below, under the heading "Purification and characterization of MBP Polypeptides".

The purified MBP 21.5 polypeptides of the invention, however prepared, will in general be characterized by the presence of some impurities. These impurities may include proteins, carbohydrates, or other molecules in amounts and of a character which depend on the production and purification processes used. These components will ordinarily be of viral, prokaryotic, eukaryotic, or synthetic origin, and preferably are non-pyrogenic and present in innocuous contaminant quantities, on the order of less than about 1% by weight.

III. Clinical Applications

As discussed above, the MBP 21.5 polypeptides and MBP nucleic acid molecules of the invention can be used in the diagnosis, clinical assessment, and treatment of MS, and for the assessment of the potential responsiveness of MS patients to therapeutic treatment involving the administration of the MBP 21.5 polypeptides. Procedures for such diagnosis and assessment involve an assay entailing the incubation of replicate cultures of T cells in the presence and absence of one or more of the MBP 21.5 polypeptides discussed herein, and the detection of T cell activation and/or T cell apoptosis (referred to in this specification and in the claims as a "T cell response") resulting from incubation in the presence, but not the absence, of the one or more polypeptides.

More specifically, such an assay comprises isolating and partially purifying T cells from a patient, combining the isolated T cells with a polypeptide selected from the group consisting of the polypeptide of SEQ ID NO:1, the polypeptide of SEQ ID NO:1 with cysteine 81 replaced with any other standard amino acid, the polypeptide of SEQ ID NO:1 with cysteine 81 replaced with an uncharged amino acid having a molecular weight of less than about 150, and the polypeptide of SEQ ID NO:1 with cysteine 81 replaced with serine, and measuring the level of a T cell response induced by the polypeptide. Methods for measuring T cell responses are described below.

In accordance with the present invention, such an assay may be provided as a kit for the detection of MBP reactive T cells comprising an isolated MBP 21.5 polypeptide in close confinement and/or proximity with an agent for use in the detection of a T cell response, such as any of the agents described below under the subheading "Detection of T Cell Responses". In a preferred embodiment of such a kit, the kit further comprises a label indicating that the kit is for use in the diagnosis and/or clinical assessment of multiple sclerosis.

A finding of T cells in a patient's CSF that exhibit a T cell response when incubated with MBP 21.5 polypeptides in this fashion is taken as an indication that the patient is suffering from MS. A finding of such MBP responsive T cells in CSF and/or blood of an MS patient is an indication that the patient is an appropriate candidate for treatment with MBP 21.5 polypeptides. The levels of such T cells in the blood of CSF may be monitored as an indication of disease progression and/or response to treatment.

The number of such reactive T cells in a patient's blood and/or CSF (the "reactive T cell index") can be monitored over time, and can be used as an indicator of the clinical progression of the disease, with increasing numbers indicating exacerbation and decreasing numbers indicating improvement. The reactive T cell index also serves as a predictor of when a therapeutic treatment would be appropriate, e.g., a sudden increase in the index would suggest that therapeutic intervention should be commenced or intensified. If the index is monitored during a course of treatment, whether or not the treatment involves the administration of MBP 21.5 polypeptides, a significant decline in the reactive T cell index is an indication of therapeutic success, while a significant rise in the index indicates therapeutic failure, and suggests that the therapeutic regimen should be adjusted.

A. Detection of T Cell Responses

Assays of T cell activation and of apoptosis are well known to those of skill in the art. Detailed discussions of and protocols for such assays can be found in numerous publications including, Voskuhl et al 1993, supra. Such assays measure alterations of certain key indicators of T cell activation, and/or apoptosis.

For T cell activation, these indicators generally include reagents for the detection of T cell proliferation, cytokine release, and expression of cytokine receptors and other activation-associated cell surface markers. For apoptosis, these indicators generally include dyes, stains, and other reagents for the observation/detection of nuclear shrinkage and/or cell death; metabolic inhibitors capable of inhibiting apoptotic cell death; stains, enzymes, labeled nucleic acid precursors, and other indicators of DNA degradation.

All assays of T cell activation and of apoptosis involve the use of cell culture (tissue culture) supplies, typically including culture vessels such as multi-well plates, dishes, and flasks, as well as test tubes and centrifuge tubes, liquid measuring devices such as pipettes, droppers, and dropper bottles, cell culture media, and buffer solutions. Many of these assays also involve a readout that involves a labeled antibody, often a secondary antibody against a primary, unlabeled antibody that specifically binds to the indicator being measured. In addition, these assays involve numerous other reagents and instruments, as discussed below and in the Examples. As used in this specification, and in the claims, an "agent for use in the detection of a T cell response" is any of the reagents (including antibodies), supplies, media, and instruments discussed herein that can be used for such detection.

Unless reagents specific for T cells are used as indicators, the measurements of T cell responses will generally involve the labeling and/or further purification of T cells from preparations of white blood cells, which are typically obtained (i.e., partially purified) by centrifugation and/or filtration of the body fluid (e.g., cerebrospinal fluid or decoagulated blood) in which they are isolated. As used hereinafter, and in the claims, "isolated T cells" are T cells that have been removed from the body of a living subject, but not necessarily further purified (e.g., by centrifugation to remove white blood cells from a body fluid or by separation of T cells from other blood cells). The isolation of T cells thus involves lancets, needles, syringes, evacuated blood collection tubes, and other blood and/or CSF collection supplies, and may further involve the use of filtration and centrifugation supplies.

Methods for specifically labeling T cells typically involve conventional immunohistochemical and/or FACS techniques involving antibodies to T cell specific markers, which are generally T cell receptors, subunits thereof, and associated molecules such as CD3. Such antibodies are commercially available from numerous sources.

Methods for at least partially purifying T cells include cell sorting by FACS using the above-mentioned antibodies, various affinity purification methods, including passage over glass beads and/or nylon wool, the use of antibodies to markers for other white blood cell types to remove cells other than T cells from mixtures of white blood cells, and differential centrifugation, e.g., centrifugal elutriation and density gradient centrifugation using density gradient media such as polysucrose (FICOLL), albumin, colloidal silica, and the like.

Detection of T cell proliferation can be accomplished by labeling or partially purifying T cells as discussed above and applying methods used to detect cell proliferation generally. One such method involves labeling newly synthesized DNA by culturing the T cells in the presence of detectable nucleic acid precursor molecules that can be incorporated into nascent DNA by living cells. Such precursors include $^3$H thymidine and other radioactively labeled precursors, and BrdU and other conveniently detectable non-radioactive precursors. When radioactively labeled precursors are used, unincorporated precursors are washed away and levels of incorporated precursors are measured by autoradiography, scintillation counting, or other conventional methods of radiation quantification.

When BrdU and the like are used, unincorporated precursors are washed away and antibodies or other reagents capable of specifically binding to the precursor are used to detect precursor that has been incorporated into nuclear DNA. Additionally, reagents that label metabolically active cells can be used to follow increases in cell number. Such reagents include MTT, XTT, MTS, and WST-1, which are cleaved by mitochondrial enzymes to yield products that can be readily detected and measured spectrophotometrically, with the level of cleavage products thus measured being proportional to the number of metabolically active cells in the sample being tested. Such reagents are commercially available from many sources.

Numerous cell surface markers of T cell activation are known in the art, and are generally detected by antibodies (which are commercially available from numerous sources) using conventional immunohistochemical and/or FACS techniques. These markers include CD25 (the IL-2 receptor), CD26, CD30, CD69, and CD71 (the transferrin receptor).

T cell activation can also be detected by measuring cytokine release into culture medium. Inactive T cells do not release cytokines, while at least some active T cells release IL-2, IL-4, IL-5, IL-6, IL-10, IL-11, IL-12, IL-13, IL-14, gamma interferon, TNF alpha, and the TNF-related cytokine known as the FAS ligand. In addition, T cell activation may be detected by T cell surface expression of activation-specific markers including CD95 (the FAS receptor). Antibodies for detecting each of these cytokines and markers are well known in the art and are commercially available; assays using such antibodies to measure cytokines, e.g., in culture medium, are also well known in the art and are items of commerce.

A particularly sensitive assay for T cell activation is the recently developed enzyme-linked immunospot (ELISPOT) assay, which typically detects cytokine release by single T cells as spots on an antibody coated substrate upon which the T cells are cultured. Such assays are described in Taguchi et al., J Immunol Meth 1990, 128:65 and Sun et al., J Immunol 1991 146:1490. Preferably the ELISPOT assay is used to detect the secretion of gamma interferon.

Materials and methods for determining whether cellular morbidity is a result of an ongoing process of apoptosis are also well known to workers in the art. In addition to conventional histochemical stains, which allow the detection of apoptosis-associated ultrastructural changes, apoptosis detection procedures, including assays and staining techniques, have been in use in the art for many years. These procedures typically determine if cell death depends upon active metabolism (e.g., protein synthesis) or whether dying cells exhibit DNA degradation (fragmentation).

The former type of procedure involves growing replicate cultures containing dying cells in the presence or absence of a metabolic inhibitor, e.g., a protein synthesis inhibitor such as cycloheximide, an RNA synthesis inhibitor such as actinomycin D, or an immune-specific inhibitor such as cyclosporin, and determining whether such inhibition delays cell death; if it does then apoptosis is almost certainly involved. See, for example, Dhein et al., 1995, in which cell death is detected as the ability of the dye propidium iodide to enter the cell.

Procedures for the detection of DNA fragmentation may involve the isolation and size separation of DNA, typically by phenol extraction and gel electrophoresis. A newer technique involves the use of the enzyme terminal deoxynucleotidyl transferase ("TdT" or "terminal transferase"), an appropriate buffer (e.g., cacodylate buffer containing a cobalt salt and a reducing agent such as DTT, DTE, or BME) and a labeled deoxynucleotide triphosphate (dNTP) or a labeled derivative or analog thereof (e.g., BrdUTP, a biotynilated dNTP, a digoxigen labeled dNTP, or a radiolabeled dNTP, collectively referred to as a "labeled XTP").

TdT incorporates labeled XTPs onto free ends of DNA molecules. Since DNA degradation associated with apoptosis involves the generation of a great many free ends compared with a much smaller number in healthy cells, the incorporation of high levels of labeled XTPs relative to healthy cells indicates ongoing apoptosis. TdT methods for detecting apoptosis thus involve the detection of the incorporated labeled XTP (usually following washing of the cells to remove unincorporated labeled XTPs) typically using conventional techniques such as autoradiography or immunohistochemistry (e.g., using antibodies against the labeled XTP—either tagged, e.g., fluorescently or enzymatically tagged antibodies, or in conjunction with tagged secondary antibodies). A commercial kit for the practice of this method is available from ONCOR, Inc., Gaithersburg, Md., as the "APOPTAG" kit.

Another recently developed technique involves an ELISA using an anti-histone capture antibody and an anti-DNA detection antibody. This assay depends on the conventional separation of intact chromatin from fragmented chromatin, with the levels of fragmented chromatin so separated being measured by the above mentioned ELISA. A commercial kit for the practice of this method is available from Boehringer Mannheim Corporation, Indianapolis, Ind., as the "cell death detection" kit.

B. Treatment

It should be noted that the MBP 21.5 polypeptides of the invention, (e.g., MBP+X2$^{Ser81}$) have various advantages in comparison to non-human-derived MBP antigens used in prior approaches for obtaining antigen tolerization in MS patients. Such advantages include the inclusion of the full spectrum of MBP immunodominant regions, and the consequent ability of these polypeptides to induce tolerance in T cells reactive with any such MBP immunodominant regions.

Intra-antigenic and inter-antigenic spread of autoreactivity are related phenomena associated with autoimmune diseases in which additional epitopes within an antigen, or additional antigens within a target tissue, become targeted by autoreactive T cells during disease progression. Such antigen spreading has been observed during the course of the inflammatory autoimmune process in the murine models of experimental allergic encephalomyelitis (EAE) and insulin-dependent diabetes (Lehmann et al. 1992; McCarron et al. 1990; Kaufman et al. 1993; Tisch et al. 1993).

These findings of antigen spreading, as well as the demonstration of variability in the immunodominant epitopes recognized by MBP reactive activated T cells in MS patients, indicate that an effective MBP-specific therapy will need to target a heterogeneous population of MBP-specific autoreactive T cells. Therefore, in order for parenteral MBP administration to be maximally effective in the treatment of MS, the complete repertoire of its immunodominant epitopes must be presented to T lymphocytes.

In accordance with the present invention, a method for treating a patient suffering from multiple sclerosis comprises administering to the patient an MBP 21.5 polypeptide. Preferably the MBP 21.5 polypeptide comprises the complete repertoire of MBP immunodominant epitopes. The MBP 21.5 polypeptide is administered in an amount sufficient to achieve a concentration of the polypeptide in a relevant compartment (i.e., body fluid or tissue compartment) of the patient's body, e.g., the patient's blood, cerebrospinal fluid, lymph, reticuloendothelial system, liver, lymph nodes, spleen, thymus, and the like, sufficient to induce apoptosis of MBP reactive T cells. Preferably the polypeptide is administered to the patient at least two times at an interval of at least twelve hours and not more than four days.

In accordance with the present invention, the concentration of the polypeptide in the patient's body fluid or tissue compartment that is sufficient to induce apoptosis of MBP reactive T cells is determined using the materials, methods, and assays described above under "Clinical Applications" and "Detection of T Cell Responses". A concentration is considered sufficient to induce apoptosis of MBP reactive T cells when a substantial decrease in the number of T cells from peripheral blood exhibiting responses to MBP epitopes (the "precursor frequency" or "reactive T cell index") is seen following treatment (compared to T cells from blood samples taken before treatment) in response to the polypeptide, as compared to control assays, which are performed using irrelevant polypeptides (e.g., albumin). An at least 25% reduction in reactive T cell index will, in general, comprise a "substantial reduction". Smaller reductions are also considered "substantial" if they represent a statistically significant reduction, i.e., a reduction that, when analyzed by a standard statistical test, such as the student's T test, will give a probability value, p, less than or equal to 0.05 and, preferably, less than or equal to 0.015.

Alternatively, the concentration of the polypeptide in the patient's blood and/or cerebrospinal fluid that is sufficient to induce apoptosis of MBP reactive T cells may be determined by routine in vivo experimentation as the amount required to stabilize the clinical course or improve the clinical symptoms of EAE or MS.

In accordance with the invention, MPB 21.5 polypeptides may also be used to induce tolerization of MBP reactive T cells in an MS patient by administration on a schedule designed to induce tolerization without inducing apoptosis (e.g., by inducing T cell anergy). Such schedules are typically used to tolerize patients to allergens, and generally involve administration of smaller doses (typically ranging from micrograms to hundreds of micrograms) of the tolerizing agent (in this case the MBP 21.5 preparation) on a weekly, biweekly, or monthly basis.

The amount of administered polypeptide that is sufficient to achieve a desired concentration of the polypeptide in a body fluid or tissue compartment of the patient can be readily determined from routine human and animal study data using standard pharmacokinetic calculations well known to those of skill in the art. Initial in vivo studies are done in mice that have been treated to induce EAE. Preferably the dose of polypeptide is subsequently determined in a primate, e.g., a human patient or a marmoset (a monkey that is known to have MBP reactive T cells in its peripheral blood). Preferably the dosage is adjusted to achieve a clinical improvement (preferably in animals) or a substantial reduction in the number of T cells from peripheral blood exhibiting responses to MBP epitopes.

The dose will also vary depending on the manner of administration, the particular symptoms of the patient being treated, the overall health, condition, size, and age of the patient, and the judgment of the prescribing physician.

Subject to the judgment of the physician, a typical therapeutic treatment includes a series of doses, which will usually be administered concurrently with the monitoring of clinical severity of disease and reactive T cell index. Administration of the polypeptides will generally be performed by an intravascular route, e.g., via intravenous infusion by injection. Other routes of administration (e.g., subcutaneous injection, intradermal injection, intramuscular injection, inhaled aerosol, oral, nasal, vaginal, rectal, and the like) may be used if desired as determined by the physician.

Formulations suitable for injection are found in *Remington's Pharmaceutical Sciences*, Mack Publishing Company, Philadelphia, Pa., 17th ed. (1985). Such formulations must be sterile and non-pyrogenic, and generally will include a pharmaceutically effective carrier, such as saline, buffered (e.g., phosphate buffered) saline, Hank's solution, Ringer's solution, dextrose/saline, glucose solutions, and the like. The formulations may contain pharmaceutically acceptable auxiliary substances as required, such as, tonicity adjusting agents, wetting agents, bactericidal agents, preservatives, stabilizers, and the like.

The formulations of the invention can be distributed as articles of manufacture comprising packaging material and the polypeptides. The packaging material will include a label which indicates that the formulation is for use in the treatment of neurologic disease and may specifically refer to multiple sclerosis.

Without intending to limit it in any manner, the present invention will be more fully described by the following examples.

EXAMPLES

Materials and methods for these examples were as follows:

Construction of Bacterial Vectors Directing the Expression of MBP 21.5 Polypeptides and Native MBP18.5

A full-length cDNA coding for the 18.5 kDa isoform of human MBP was obtained from the ATCC (#5748; ATCC, Rockville, Md.). Plasmid pHBP-1 was used as a template in a standard PCR reaction using AmpliTaq (Perkin-Elmer, Norwalk, Conn.) for 30 cycles with denaturation at 94° C. for 1 min, annealing at 52° C. for 1 min and extension at 72° C. for 1 min. The sense oligonucleotide primer (5'-CATATGGCGT CACAGAAGAG AC-3', SEQ ID NO:13) encodes the N-terminus of hMBP18.5 (MASQKR) and contains an NdeI cloning site, whereas the antisense primer (5'-GGATCCTTAG CGTCTAGCCA TGGGTG-3', SEQ ID NO:14) encodes the C-terminal residues (PMARR) and contains a BamHI cloning site. Following an additional extension at 72° C. for 10 min, the resulting 526 base pair (bp) fragment was subcloned into PCRII (Invitrogen, San Diego, Calif.) as described by the supplier. Kanamycin-resistant *E. coli* DH10B (Gibco/BRL, Gaithersburg, Md.) transformants were selected and the insert identified by restriction analysis and verified by dideoxy sequence analysis. The MBP coding region was subcloned into the NdeI and XhoI sites of the phage T7 promoter plasmid pET14b (Novagen, Madison, Wis.) and later recloned into pET22b (Novagen, Madison, Wis.). The resulting recombinant MBP18.5 gene contains only unmodified native codons, except for an additional 18 nucleotide sequence that encodes a histidine tag at the 3' end (immediately preceding the termination codon) that is not found in the native human MBP18.5 protein, and has been added to facilitate purification of the product of this MBP18.5$^{hum.}$ gene. The resulting recombinant vector (pET22b/MBP18.5$^{hum.}$) was transformed into *E. coli* BL21(DE3) (Novagen, Madison, Wis.) where the DE3 lysogen contains the gene for T7 polymerase behind the *E. coli* lacUV5 promoter (Studier et al., 1990).

A synthetic recombinant gene encoding the 21.5 kDa isoform of human MBP was constructed in three rounds of overlapping PCR (Ho et al. 1989) (see FIG. 1). Each of three gene subdomains was synthesized in a 100 μl reaction using 5 pmole of each the appropriate pair of HPLC purified oligonucleotides and 0.5 units of Taq polymerase (Perkin-Elmer). Thirty cycles of denaturation for 1 minute at 95° C., annealing at 50° C. for 1 minute and DNA strand extension at 72° C. for 1 minute were carried out. Five percent of each purified PCR fragment was then used as a template in a second round of PCR, where two subdomains were combined using flanking oligonucleotides. Purification of these DNA fragments and a third round of PCR resulted in amplification of a 648 bp product. The PCR product was digested with EcoRI and HindIII, subcloned into pBS(-), and transformed into *E. coli* XL-1 Blue (Stratagene, LaJolla, Calif.). Ampicillin-resistant transformants were selected and the desired constructions identified by restriction and sequence analysis. Restriction fragments from several independent clones were combined to remove undesired mutations that occurred during PCR cloning, and the resulting MBP+X2$^{Cys81/Bact.}$ gene was cloned into pET22b at the NdeI and HindIII sites.

An altered gene encoding a cysteine to serine substitution at amino acid residue 81 of the 21.5 kDa isoform of human MBP was constructed by the following steps. PCR amplification of an internal MBP fragment was carried out using pET22b/MBP21.5$^{hum.}$ as template along with the mutagenic antisense primer (5'-GTCTTTGTAC ATGTT*CGA*CA GGCCCGGCTG GCTACG-3', SEQ ID NO:15, Ser$^{81}$ codon underlined, NspI site in italics) in combination with a sense oligonucleotide primer (5'-CAGCACCATG GACC-3', SEQ ID NO:16, NcoI site in italics). The NspI-NcoI restriction fragment in MBP+X2$^{Cys81/Bact.}$ was then exchanged with the mutated fragment to create MBP+X2$^{Ser81/Bact.}$.

By using the MBP18.5$^{hum.}$ gene as template in overlapping PCR, a version of MBP+X2$^{Cys81}$ was created with native human codons. A PCR fragment that includes human exon 2 sequence was generated from pET22b/rhMBP18.5 by utilizing sense oligonucleotide 5'-GGTGCGCCAA AGCGGGGCTC TGGCAAGGTA CCCTGGCTAA AGC-CGGGCCG GAGCCCTCTG CCCTCTCATG CCCG-CAGCCA GCCTGGGCTG TGCAACATGT ACAAG-GACTC ACACCACCG GCAAGAAC-3', (SEQ ID NO:17, in combination with an antisense oligonucleotide (SEQ ID NO:18) that hybridizes to the T7 terminator of plasmid pET22b. A second PCR fragment was generated using the same template but with a T7 promoter oligonucleotide (SEQ ID NO:19) in combination with an antisense oligonucleotide (5'GGCTTTAGCC AGGGTACCTT GCCAGAGCCC CGCTTTGGC 3', SEQ ID NO:20) that hybridized to the 5' end of exon 2. Fusion of both PCR products by amplification with T7 promoter and terminator oligonucleotides in a second round of PCR completed the construction of a PCR product containing the MBP+X2$^{Cys81/hum.\ gene}$. A restriction fragment obtained from this PCR product was then subcloned into pET22b at the NdeI and HindIII sites and the selection of the desired clone was confirmed by sequence analysis.

Bacterial Expression and Identification of Recombinant MBP

For expression of recombinant MBP polypeptides, *E. coli* strain BL21(DE3) was transformed with the expression plasmids and ampicillin-resistant colonies selected and grown in Terrific Broth (TB) medium (Sambrook et al. 1989) to an OD$_{600}$ of 0.6. Protein expression was induced for 4 hours with 1 mM isopropylthiogalactoside (IPTG). Analytical characterization of recombinantly expressed MBP polypeptides was carried out by removing 1 ml of induced cells at an $OD_{600}$ of 1.5. Cell pellets were lysed by boiling in 100 µl of 20 mM Tris-HCl, pH7.5 with 10% of the lysate analyzed by 16% SDS-PAGE (Novex, San Diego, Calif.). recombinantly expressed MBP polypeptides were identified by either Coomassie R-250 staining or immunoblotting with rat monoclonal antibodies specific to either the human MBP amino-terminal residues 36–50 corresponding to MBP exon 1 (MCA 408, SeroTec, Indianapolis, Ind.) or carboxy-terminal residues 129–138 corresponding to MBP exon 6 (MCA 70, SeroTec, Indianapolis, Ind.).

For fractionation of *E. coli* cells into soluble and insoluble fractions, cell pellets from two ml of each induced culture was collected at an $OD_{600}$ of 1.5 and resuspended in 400 ml of 20 mM Tris-HCl pH 8.0. To prepare a total cell lysate, the suspension was made 100 mg/ml with lysozyme and 1 mM with phenylmethylsulfonyl fluoride, then incubated at 30° C. for 15 minutes. This was followed by the addition of 10 mM $MgCl_2$ and 200 mg/ml of DNase I (Sigma, St. Louis, Mo.) and incubation for 20 minutes at room temperature. The cell lysate was divided, one-half receiving additional Tris buffer and the other half made 0.1N HCl and extracted at room temperature for 30 minutes. After centrifugation, the soluble supernatant was removed from the insoluble pellet and each fraction boiled for 5 minutes in SDS-containing loading dye. SDS-PAGE gels of 20% of each fraction were analyzed for recombinantly expressed MBP polypeptides as described above.

Purification and Characterization of Recombinant MBPs

For purification of recombinantly expressed MBP polypeptides, 1 L cultures of induced cells were harvested by centrifugation and pellets homogenized in 10 ml/g (10% w/v) of 0.1N HCl using a TEKMAR homogenizer (The Tekmar Co., Cincinnati, Ohio). Cells were mechanically disrupted by 3 passes (at 10,000 psi with nitrogen) through a MICROFLUIDIZER (Model M110-T, Microfluidics Corp., Newton, Mass.) with all manipulations performed on ice. The soluble fraction containing recombinantly expressed MBP was collected as the supernatant following centrifugation of the cell lysate at 10,000×g for 30 min at 4° C. in a Beckman JA-10 rotor. The supernatant was filtered through a WHATMAN POLYCAP TF (0.45 µm) membrane (Whatman LabSales, Hillsboro, Oreg.) and concentrated 5–10 fold using a PM-10 membrane in an AMICON stir cell apparatus (Amicon, Beverly, Mass.). Particulates were removed from the concentrated fraction by passing through a MILLEX GV (0.2 mm) syringe filter (Millipore Corporation, Bedford, Mass.) and the filtered sample loaded onto a VYDAC C4 reverse phase column (1.0 cm dia/25 cm length, VYDAC, Hesperia, Calif.) at 4.1 ml/minute. Proteins were eluted using a linear 25–40% acetonitrile/0.1% trifluoroacetic acid (TFA) gradient for 30 minutes, then lyophilized.

For purification of recombinantly expressed MBP polypeptides, the lyophilized material was resuspended in binding buffer (8M urea, 10 mM beta-mercaptoethanol, 0.1M $NaH_2PO_4$, 0.01 M Tris-HCl, pH 8.0) and bound to Ni-NTA resin according to the manufacturers instructions (Qiagen Inc., Chadsworth, Calif.). The column was washed twice with the same binding buffer, and contaminating *E. coli* proteins were removed with binding buffer that was adjusted to pH 6.3 (wash 3). rhMBP was eluted with a step gradient that included binding buffer at pH 5.9 (elution 1) and pH 4.5 (elution 2), and finally 6M guanidine hydrochloride, 0.2M acetic acid (elution 3). All fractions and a portion of the column resin were analyzed by 16% SDS-PAGE in the presence of reductant.

MBP polypeptides were quantified using a rapid analytical reversed-phase HPLC assay. A 4.6×50 mm C18 column (C18 HYTACH, Glycotech, Branford, Conn.) was used and assays were performed at 80° C. in a manner similar to the HPLC described by Kalghatgi and Horvath, 1987. Recombinantly expressed MBP polypeptides were extracted from disrupted cells with 0.1N HCL and fractionated on the C18 HYTACH reversed-phase column using a linear 10–30% acetonitrile/0.1% triflouroacetic acid (TFA) gradient over 1 minute. In the linear assay range, measurement of the MBP polypeptide peak height is directly proportional to the quantity of MBP polypeptide. The concentration of an MBP+$X2^{Cys81}$ standard was determined by amino acid composition. The molecular weight for MBP+$X2^{Cys81}$ was determined by mass spectrophotometry to be 22,188 daltons. N-terminal sequencing of the purified MBP+$X2^{Cys81}$ protein gave the amino acid sequence Ala Ser Gln Lys Arg Pro Ser Gln Arg His Gly Ser Lys Tyr Leu Ala Thr Ala Ser Thr Met Asp His Ala Arg, corresponding to the first 25 amino acids predicted from the nucleotide sequence of MBP+$X2^{Cys81/hum.}$ (SEQ ID NO:22).

Establishment of MBP18.5- and Exon 2-specific T Cell Lines and Proliferation Assays Native human MBP was prepared as described previously (Voskuhl et al. 1993a). MBP exon 2-encoded synthetic peptide was purchased from Synthecell Corp. (Rockville, Md.) and was greater than 95% pure by HPLC analysis. Peripheral blood lymphocytes were isolated by leukapheresis and separation on FICOLL gradients. Cells were then cryopreserved in RPMI 1640 (Whittaker Bioproducts, Walkersville, Md.) with 10% DMSO and stored in liquid nitrogen until use. T cell lines were generated using a limiting cell concentration, as described previously (Voskuhl et al. 1993a). 2A2 and 3H5 are human T cell lines that were obtained from normal individuals. 1H7, 1G1 and 3A11 are human T cell lines obtained from MS patients and are specific for the exon 2-encoded region of MBP. T cell lines were rested for 10 days after the last restimulation, then used as responders at a concentration of $2 \times 10^5$ cells/ml. Autologous irradiated (3000 rad) peripheral blood lymphocytes (PBL) were used as stimulators at a concentration of $1 \times 10^6$/ml. Fifty microliters of both responder and stimulator cells were mixed in each well of a round bottomed 96-well microtiter plate (Nunc, Roskilde, Denmark) with 100 µl of the particular MBP antigen or medium alone. For the recombinant MBPS, lyophilized preparations from the reversed-phase HPLC purification were resuspended in PBS at a concentration of 8–10 mg/ml then diluted with medium immediately prior to use. Assays were done in triplicate and carried out in Iscove's Modified Dulbecco's Medium (IMDM, Gibco, Grand Island, N.Y.) containing 2 mM L-glutamine, 100 U/ml penicillin and 100 mg/ml streptomycin (all Whittaker Bioproducts, Walkersville, Md.) supplemented with 10% pooled human serum (obtained from 4–7 normal AB NIH blood bank donors, heat inactivated and sterile filtered before use) Cultures were incubated for 72 h at 37° C. in 5% $CO_2$. During the last 18 h of culture, cells were pulsed with 1 mCi/well $^3$[H]-thymidine, harvested onto glass fiber filters, and thymidine incorporation measured by scintillation counting.

Results

Construction and Bacterial Expression of Recombinant Human MBP Genes

A synthetic gene was constructed to encode the fetal isoform of adult human MBP (21.5 kDa isoform, MBP+

Figure 2:
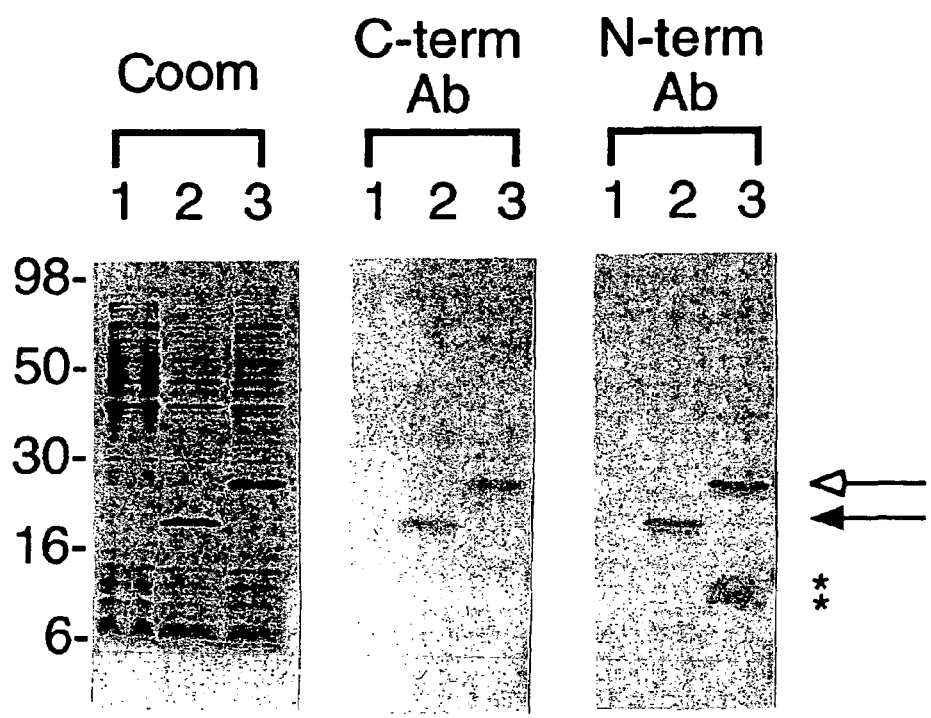
FIG. 2. Recombinant MBP expression and subcellular localization in bacterial cells—unfractionated whole cell lysates. Cell lysates were prepared from induced cultures of BL21(DE3) cells that were transformed with control pET22b vector without added insert ("1"), pET22b/MBP18.5$^{hum.}$ ("2") or pET22b/MBP+X2$^{Cys81/Bact.}$ ("3"). Whole cell lysates were separated by 16% SDS-PAGE under reducing conditions (note that under these conditions, no dimers are seen), then Coomassie stained (Coom) or immunoblotted with monoclonal antibodies that recognize either a carboxy-terminal epitope ("C-term Ab") or an amino-terminal epitope ("N-term Ab") of human brain MBP. Asterisks highlight the position of two fragments of MBP+X2$^{Cys81}$ that are recognized by only the "N-term Ab" mAb. Molecular weights in kilodaltons (as determined by electrophoreising marker proteins) appear on the left. The open and closed arrows mark the positions of MBP+X2$^{Cys81}$ and MBP18.5, respectively.

$X2^{Cys81}$) (see FIGS. 1 and 2). While others have typically constructed synthetic genes by ligating numerous oligonucleotides that encompass the complete sense and antisense strands of a particular coding region (Jayarman et al. 1991; Williams et al. 1988; Hernan et al. 1992; Wosnick et al. 1987), only six oligonucleotides (SEQ ID NO:5, SEQ ID NO:6, SEQ ID NO:7, SEQ ID NO:8, SEQ ID NO:9, and SEQ ID NO:10) were utilized here to synthesize the 644 bp gene encoding recombinant human MBP+$X2^{Cys81}$. The HPLC-purified oligonucleotides ranged in size from 110 to 130 bp, with 20–25 bp overlapping regions designed for hybridization of sense and antisense strands during 3 rounds of PCR (FIG. 1). For optimal bacterial expression of the recombinant MBP gene, many of the human codons were converted to preferred bacterial codons based on codon bias tables created for all known (Wada et al. 1992) or highly expressed (Grosjean and Fiers, 1982) *E. coli* genes. Significant codon changes were employed, especially for those encoding arginine, proline and lysine, which comprise 26% of the amino acid residues in MBP21.5.

Several independent clones were sequenced and each had multiple nucleotide substitutions or deletions attributed to either rejection of the synthetic DNA by the bacterial cloning strain or PCR-based errors. All of these errors were corrected except for cytosine to thymine substitutions that were identified at nucleotide positions 462, 528 and 532. These changes were not corrected, as they conserve the encoded MBP+$X2^{Cys81}$ amino acid sequence and are not deleterious to the bacterial codon preference (Wada et al. 1992). For recombinant expression of the adult human brain derived (18.5 kDa) isoform of MBP, a cDNA clone with native human codons encoding this isoform (MBP18.5/$^{hum.}$, encoding MBP18.5) was modified by PCR to include the appropriate restriction sites for cloning into the same expression vector.

The expression of recombinant MBP polypeptides in bacteria was initially characterized using small-scale shake flask cultures grown in rich TB medium. Following induction of 10 ml cultures with IPTG, both recombinant forms of MBP were expressed to high levels in BL21(DE3) cells. MBP18.5 and MBP+$X2^{Cys81}$ were the major proteins identified by Coomassie dye staining of total bacterial proteins separated by SDS-PAGE (FIG. 2, "Coom") and were recognized specifically by antibodies directed to either the carboxy-(FIG. 2, "C-term Ab") or amino-(FIG. 2, "N-term Ab") terminus of human MBP. Two smaller MBP-immunoreactive polypeptides (between 6–16 kDa) could be identified in the MBP+$X2^{Cys81}$ lysate, but only by immunoblot analysis with the N-terminal antibody, indicating that premature termination of translation near the carboxy terminus, rather that proteolysis, was responsible for their presence. This was confirmed in pulse-chase labeling experiments which showed that the smaller polypeptides were stable during the course of the experiment.

Figure 3:
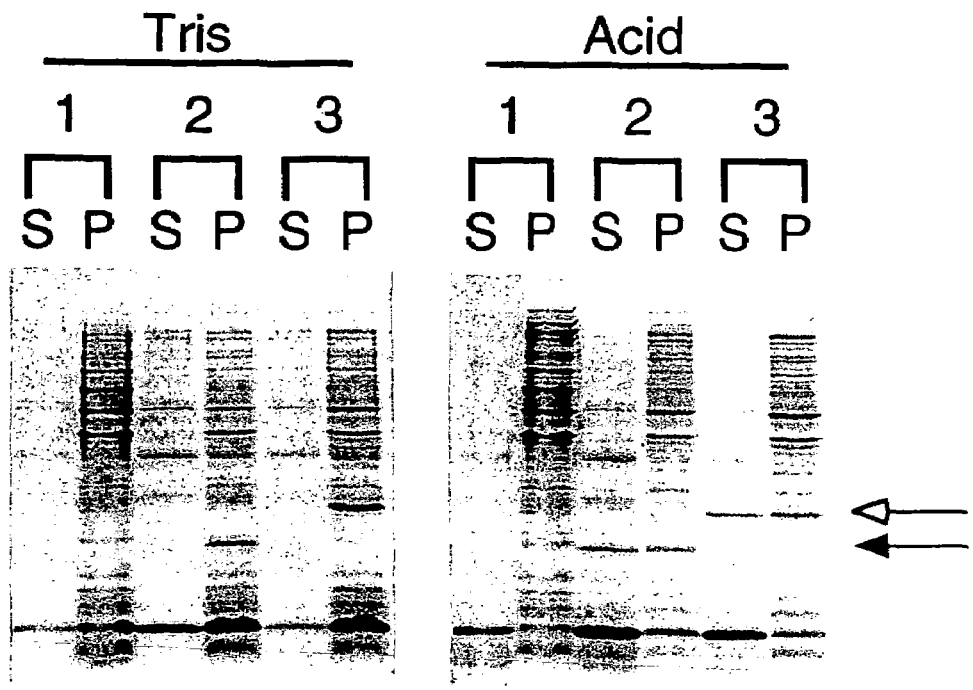
FIG. 3. Recombinant MBP expression and subcellular localization in bacterial cells—soluble vs. insoluble fractions. Cell lysates were prepared from induced cultures of BL21(DE3) cells that were transformed with control pET22b vector without insert ("1"), pET22b/MBP18.5$^{hum.}$ ("2") or pET22b/MBP+X2$^{Cys81/Bact.}$ ("3"). Bacterial lysates were fractionated into soluble ("S") or insoluble pellet ("P") fractions using either neutral buffer ("Tris") or 0.1N HCl ("Acid") conditions as described above. Shown are the Coomassie stained gels obtained by SDS-PAGE of the cell fractions under reducing conditions (note that under these conditions, no dimers are seen). The open and closed arrows mark the positions of MBP+X2$^{Cys81}$ and MBP18.5, respectively. Note that the acid extraction (but not the neutral extraction) allowed recovery of the MBP+X2$^{Cys81}$ and the MBP18.5 polypeptides in the soluble fractions.

Although inclusion bodies were not evident in shake flask experiments, recombinant MBPs were observed in the insoluble fraction of lysed bacterial cells (FIG. 3, "Tris"). Previously, a homogeneous protein purified from bovine spinal cord was shown to have encephalitogenic activity and be soluble at pH 2–3 (Einstein et al. 1962). This encephalitogenic protein was subsequently identified as MBP, and consists almost exclusively of the 18.5 kDa isoform (Deibler et. al. 1972). Since MBP is acid soluble, we reasoned that it might be possible to streamline purification by direct acid extraction of bacterial lysates. We therefore attempted to solublize rhMBPs under acidic conditions. Treatment of total cellular lysates with 0.1N HCl (FIG. 3, "Acid") released most of the rhMBPs into the soluble fraction (S). The inability to extract all of the rhMBPs from the insoluble pellet fraction (P) may be due to incomplete lysis of cells during this particular sample preparation.

Purification and Characterization of MBP Polypeptides

Figure 4:
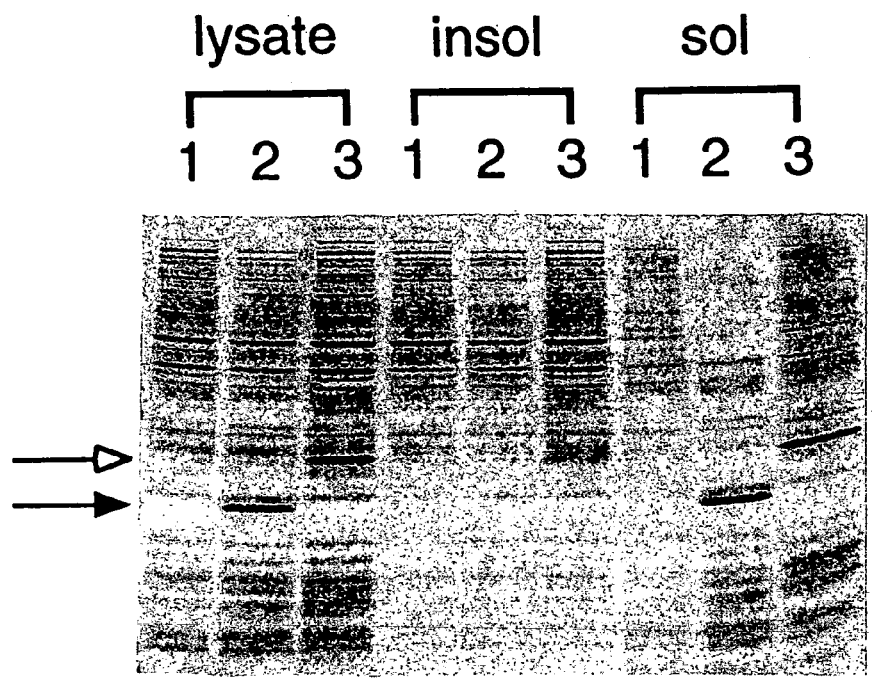
FIG. 4. Large scale acid extraction of recombinant MBP from bacterial cells. Shown is a Coomassie stained SDS/PAGE gel carried out under reducing conditions (note that under these conditions, no dimers are seen). Each group of three lanes shows whole cell lysate ("lysate") and insoluble ("insol") and soluble ("sol") fractions obtained from simultaneous acid extraction and mechanical disruption. Cells were harvested from induced cultures of BL21(DE3) cells transformed with either pET22b vector without added insert ("1"), pET22b/MBP18.5$^{hum.}$ ("2") or pET22b/MBP+X2$^{Cys81/bact.}$ ("3"). The positions of MBP+X2$^{Cys81}$ (open arrows) and MBP18.5$^{hum.}$ (closed arrows) are indicated. Note that this large scale acid extraction allowed recovery of almost all of the MBP+X2$^{Cys81}$ and the MBP18.5 polypeptides in the soluble fractions.
Figure 5:
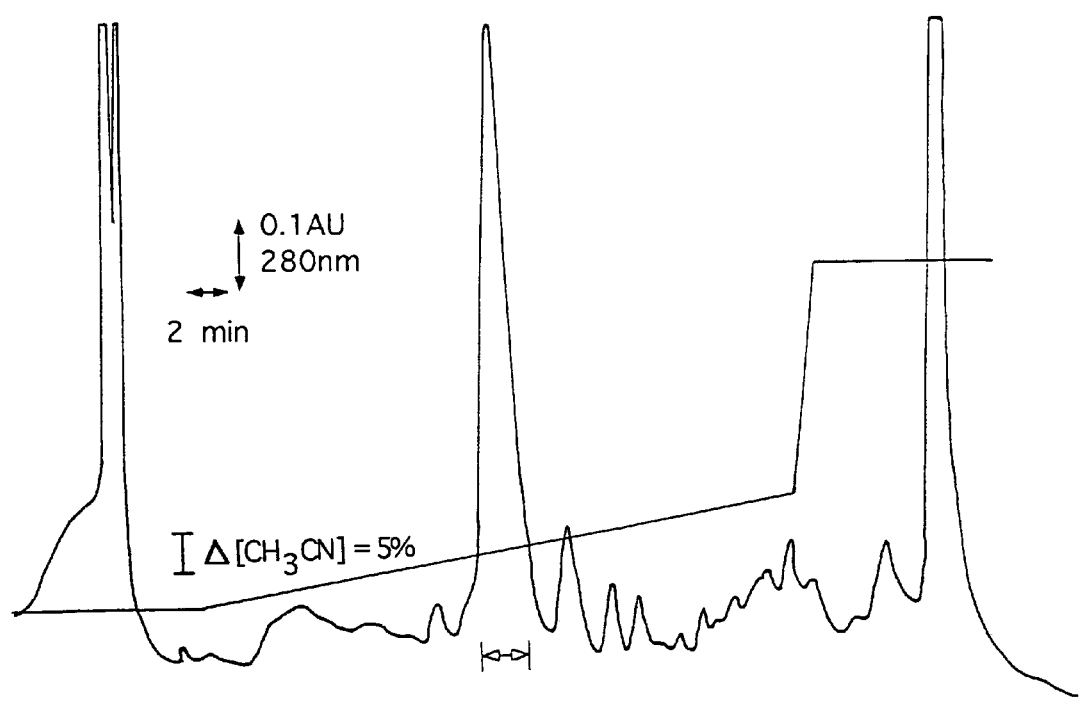
FIG. 5. Chromatograph showing reversed-phase chromatographic isolation of acid-extracted MBP+X2$^{Cys81}$. The soluble fraction recovered from the experiment shown in FIG. 4 ("sol" lane "3") was chromatographed over a VYDAC C4 reverse phase column and eluted via a 25–50% (CH$_3$CN)/0.1% TFA gradient. MBP+X2$^{Cys81}$ is found in pooled fractions that correspond to the large peak eluting between 17 and 20 minutes. A similar chromatograph was obtained for MBP18.5.
Figure 6:
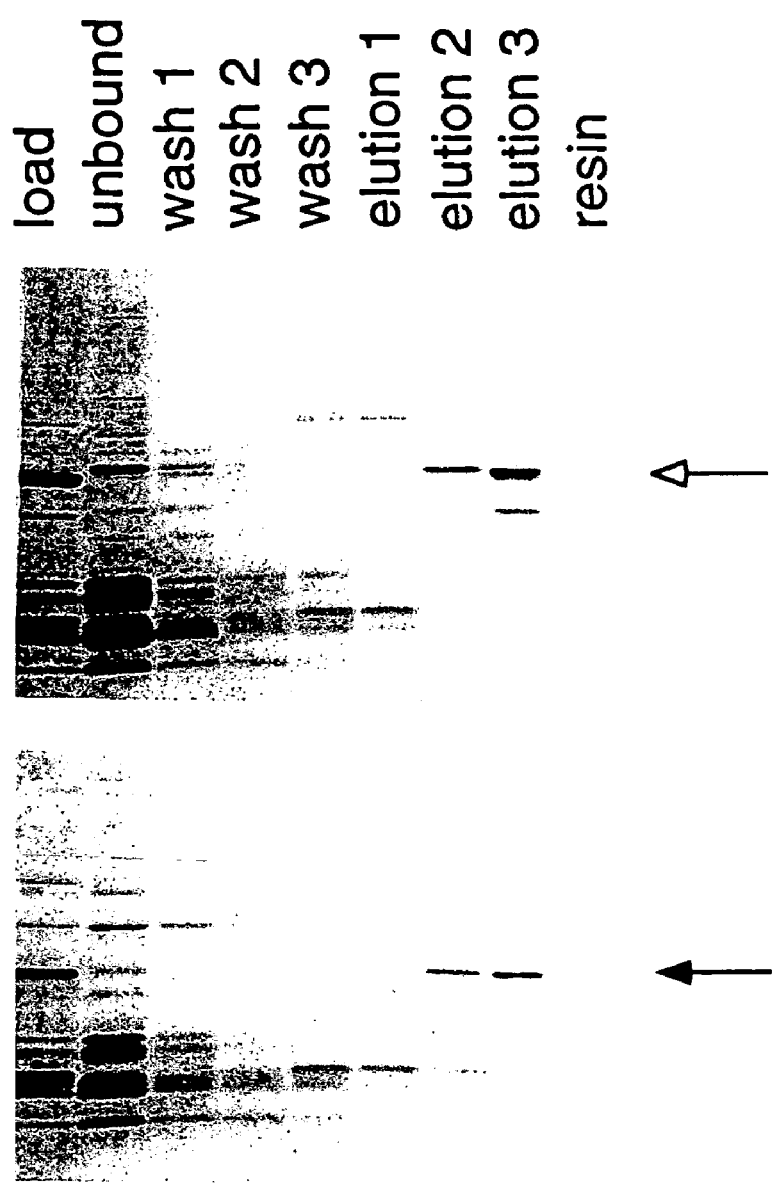
FIG. 6. Purification of MBP+X2$^{Cys81}$ (top panel) and MBP18.5 (bottom panel) by metal chelation chromatography of acid extracts of bacterial cells. Shown are Coomassie stained gels of protein fractions collected during the affinity purification and subjected to SDS-PAGE. The positions of MBP+X2$^{Cys81}$ (open arrow) and MBP18.5 (closed arrow) are indicated. Lanes are labeled "load" (the lysate loaded onto the column), "unbound" (the column flow-through, "wash 1", "wash 2", and "wash 3" (the column eluate from each wash), "elution 1", "elution 2", and "elution 3" (the column eluate from each elution step), and resin (a sample of column resin taken after the final elution, boiled in sample buffer, and loaded on the gel).

For purification of recombinantly expressed MBP polypeptides, cells from 1 L shake flask cultures were mechanically disrupted in the acidic conditions described above. Following simultaneous cell disruption and acid extraction, all of the recombinantly expressed MBP polypeptides were found in the soluble fraction (FIG. 4, "sol"). The soluble acid fraction was applied directly onto a VYDAC C4 reversed-phase column and rhMBPs eluted as a single, sharp peak at 17–20 min with a 25–40% acetonitrile/0.1% TFA gradient (FIG. 5). N-terminal sequencing of the peak fraction verified the correct amino-terminal sequence for the MBP polypeptides, as described above. The predicted molecular weight of MBP+$X2^{Cys81}$ with an additional carboxy-terminal histidine tag agreed with the mass of 22,185 daltons obtained by mass spectrophotometric analysis of the peak fraction. Coomassie stained gels of the pooled peak fractions identified the recombinant MBP polypeptides, but also showed a heterogeneous mix of truncated MBP fragments apparently produced by limited acid hydrolysis of full-length MBP polypeptides (FIG. 6, "load"). By exploiting the C-terminal histidine tag, full-length MBP material was obtained by metal chelation chromatography using denaturing conditions and acidic pH elutions (FIG. 6). The majority of the full-length MBP polypeptides eluted with either elution 2 (8M urea, 10 mM beta-mercaptoethanol, 0.1M $NaH_2PO_4$, 0.01 M Tris, pH 4.5) or elution 3 (6M guanidine hydrochloride, 0.2M acetic acid), although contaminating *E. coli* proteins were observed in the eluate from the less stringent second elution (FIG. 6, "elution 2").

Figure 7:
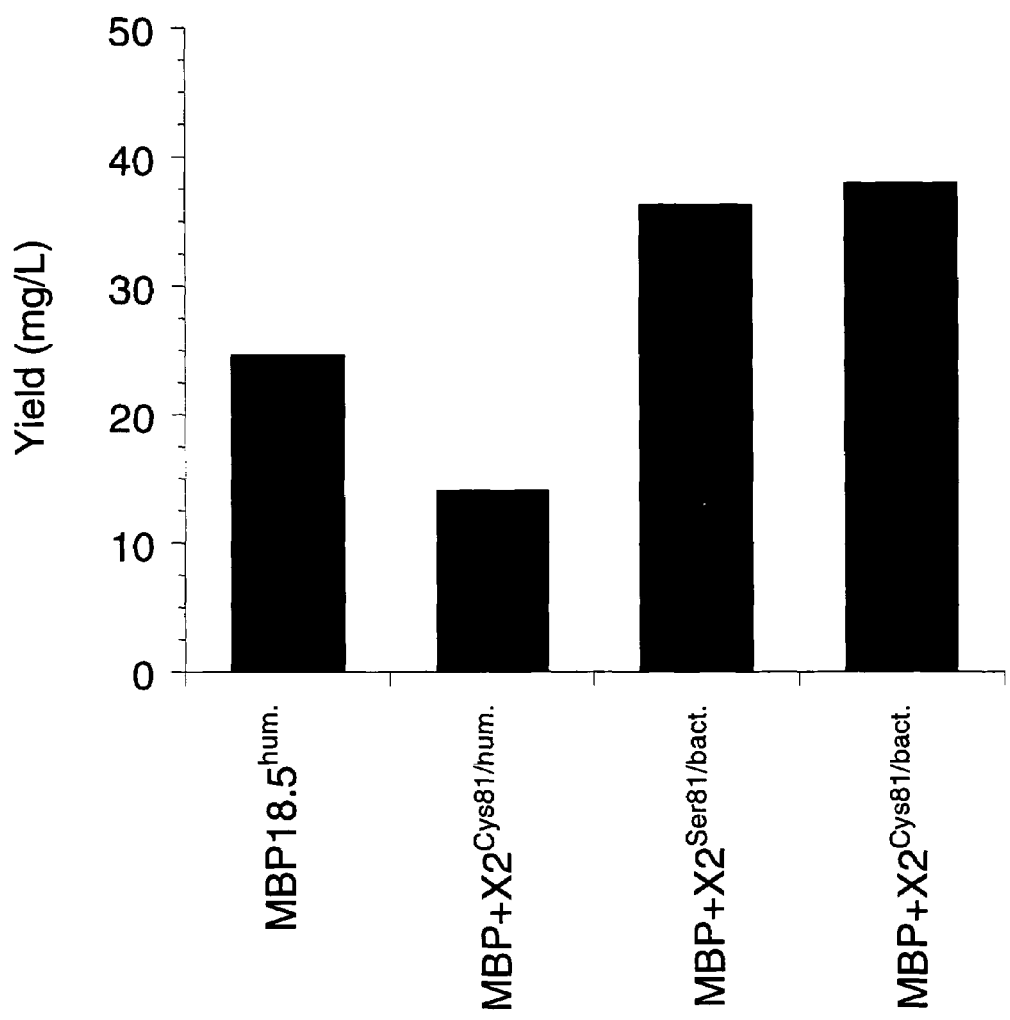
FIG. 7. Yield of bacterially expressed MBP polypeptides in bacteria transfected with nucleic acid vectors comprising the nucleic acid sequences MBP18.5$^{hum.}$ (SEQ ID NO:25), MBP+X2$^{Cys81/hum.}$ (SEQ ID NO:22), MBP+X2$^{Ser81/bact.}$ (SEQ ID NO:24) and MBP+X2$^{Cys81/bact.}$ (SEQ ID NO:23), as indicated.

To quantitatively compare the expression of the MBP+ $X2^{Cys81/bact.}$ to that of MBP18.5/$^{hum.}$, soluble acid lysates were prepared from three sets of one liter bacterial cultures and analyzed using the rapid analytical reversed-phase HPLC assay described above. Using a standard amount of MBP+$X2^{Cys81}$, as determined by amino acid analysis, and relating the peak height to protein concentration, we observed that 1.5 to 2.0-fold more MBP 21.5 polypeptide was expressed from the synthetic MBP+$X2^{Cys81/bact.}$ gene compared to the expression from the MBP18.5/$^{hum\ gene}$. The average expression level of recombinant protein from MBP genes with bacterial codons was 50 mg/L compared to 30 mg/L from genes with human codons. This reflects bacterial codon bias and not an effect of exon 2-related sequences, as a strain that expressed the MBP+$X2^{Cys81/hum.}$ gene produced a similar amount of MBP polypeptide as the strain expressing the MBP18.5/$^{hum.}$ (see FIG. 7 and Table 2).

Under physiological conditions, a fraction of MBP+ $X2^{Cys81}$, but not MBP18.5, formed an apparent dimeric molecule that was identified by Coomassie staining and Western blotting of nonreduced samples on SDS-PAGE gels. Dimers are not observed under similar conditions with reduced samples. MBP dimers also have been observed after reversed-phase HPLC fractionation of myelin proteins from bovine CNS (van Noort et al. 1994).

Such dimers are particularly undesirable in a protein preparation that is to be formulated for pharmaceutical administration, as, for such use, such proteins are generally preferred as single molecular entities with defined characteristics, including a unique molecular weight. It was thus important to devise a means by which single, monomeric forms of MBP 21.5 polypeptides could be conveniently and efficiently prepared. In order to test whether dimer formation of MBP+X2$^{Cys81}$ was mediated through the single cysteine residue at position 81 (Cys$^{81}$) of exon 2, the cysteine (Cys$^{81}$) was converted to a serine (Ser$^{81}$) by site-directed mutagenesis.

Reversed-phase HPLC showed that MBP+X2$^{Ser81}$ was expressed in bacteria at a level similar to MBP+X2$^{Cys81}$ (on average 50 mg/L, see FIG. 7) and remained monomeric in physiological solution, without reductant. As an alternative method of testing such an amino acid substitution for effective elimination of dimer formation, X2MPB peptides may be prepared and tested for dimer formation in physiological solution, without reductant.

MBP18.5- and MBP Exon 2-specific T Cells Recognize Recombinant Human (rh) MBPs

Figure 8:
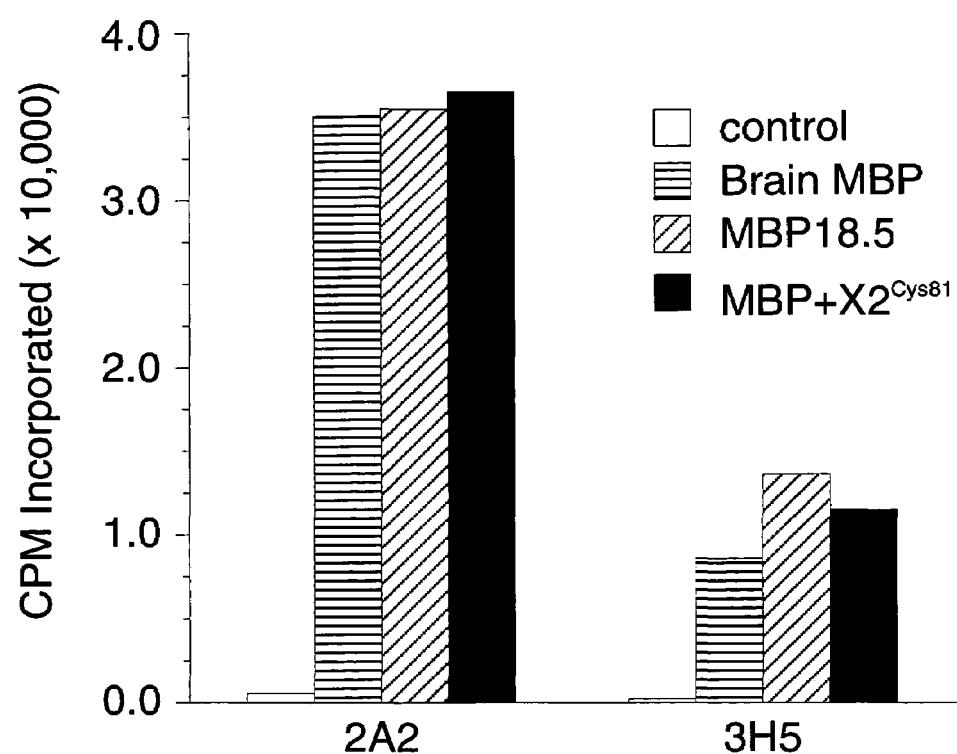
FIG. 8. MBP antigens elicit proliferative responses from human T cell clones specific for adult, brain-derived MBP. T cell lines specific for adult brain MBP18.5 were stimulated with medium alone ("control") or medium containing 10 mg of either purified adult human brain MBP ("Brain MBP"), bacterially produced MBP18.5 ("MBP18.5"), or bacterially produced MBP+X2$^{CYS81}$("MBP+X2$^{Cys81}$"). Reported are total incorporated $^3$H-CPM from one representative proliferation assay done in triplicate as described in the Examples. "2A2" and "3H5" are human T cell lines obtained from normal individuals as described in the Examples.

To assess the biological activity of recombinant forms of MBP, we tested the in vitro proliferation response of human MBP-specific T cell lines when challenged with the recombinant proteins. T cell lines were generated that respond to brain-derived human MBP18.5 or a synthetic exon 2 peptide (amino acid residues 60–85 of MBP21.5, SEQ ID NO:1). Two MBP18.5-specific lines, 2A2 (recognizing residues 31–50) and 3H5 (recognizing residues 87–106), were stimulated by incubation for 72 hours in vitro with either MBP18.5 or the MBP+X2 polypeptides. During the final 18 hours of this incubation the cells were pulsed with $^3$H-thymidine to allow measurement of cell proliferation. As shown in FIG. 8, both T cell lines responded equally well to MBP+X2$^{Cys81}$ and MBP18.5, regardless of whether purified from human brain or bacteria. We also analyzed the antigen recognition of additional human T cell lines that respond to MBP epitopes that have been described in the art. As designated in the art, and described herein, these MBP 18.5 epitopes are contained within residues 106–125, 136–155, 141–170, and 151–170 of MBP18.5, with the numbering being that used in the art, which is based on the amino acid sequence of the porcine MBP molecule. In each case, significant T cell proliferation was observed in response to native MBP18.5 and recombinant MBP+X2$^{Cys81}$.

The MBP+X2 molecules were engineered to include exon 2-encoded peptide sequences. In addition to providing a means to prepare therapeutic agents containing X2, the molecules allowed the determination of whether or not APCs could display exon 2 epitopes derived from full length MPB 21.5 in a manner that allowed recognition by T cells. This was also important for the MBP+X2$^{Ser81}$ polypeptide, as it was not known if the single cysteine residue in exon 2 was essential for T cell recognition.

Figure 9:
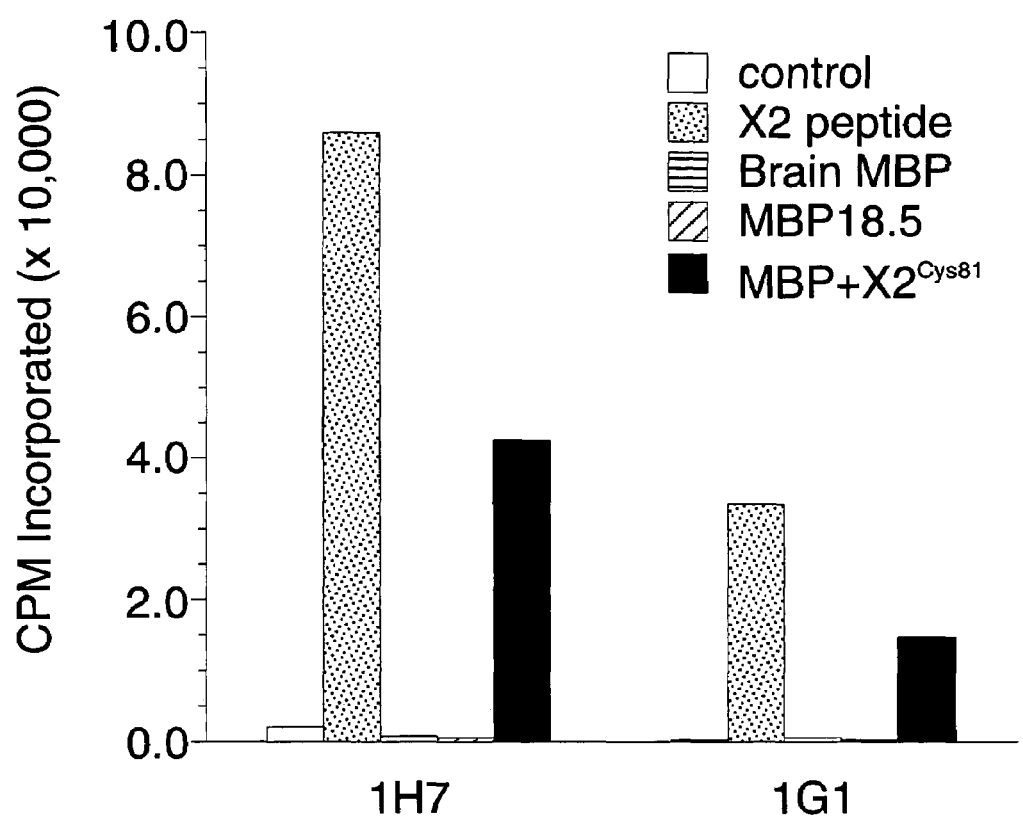
FIG. 9. Proliferative responses of exon 2-specific human T cell lines to MBP antigens. Human T cell lines 1H7 and 1G1 were stimulated with medium alone ("control") or medium containing 10 μg of either purified adult human brain MBP ("Brain MBP"), bacterially produced MBP18.5 ("MBP18.5"), bacterially produced MBP+X2$^{Cys81}$ ("MBP+X2$^{Cys81}$"), or exon 2-encoded peptide corresponding to amino acids 59 to 84 of SEQ ID NO:1 ("X2 peptide"). Presented are the total $^3$H-CPM incorporated during the proliferation assays, which were done in triplicate as described in the Examples. 1H7 and 1G1 are human T cell lines that are specific for the exon 2 encoded region of MBP and were obtained from the same MS patient as the 3A11 line used in the experiment set forth below in FIG. 10. Presented are the total $^3$H cpm incorporated during the proliferation assays, which were done in triplicate as described in the Examples.
Figure 10:
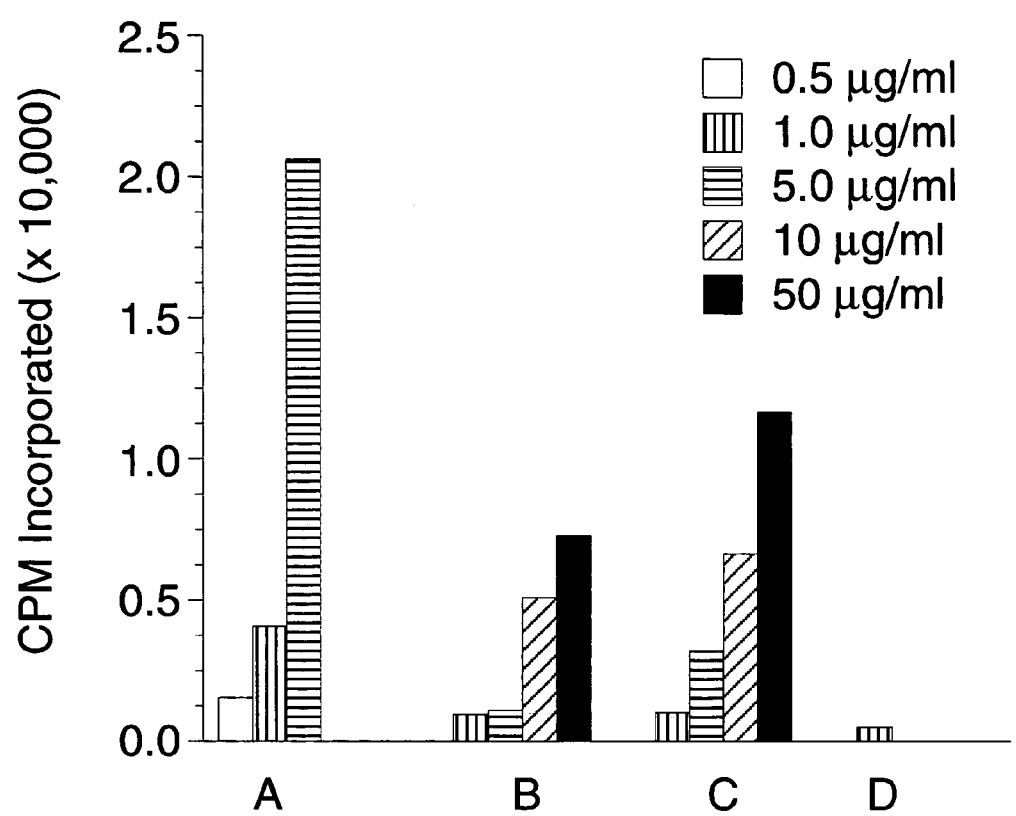
FIG. 10. Proliferative responses of exon 2-specific human T cell lines to MBP+X2$^{Cys81}$ and MBP+X2$^{Ser81}$. Human T cell line 3A11 was stimulated with varying doses of exon 2 peptide ("A"), MBP+X2$^{Cys81}$ ("B"), MBP+X2$^{Ser81}$ ("C"), or medium alone ("D"). 3A11 is a human T cell line that is specific for the exon 2 encoded region of MBP and was obtained from the same MS patient as the 1H7 and 1G1 lines used in the experiment described in FIG. 9. Presented are the total $^3$H cpm incorporated during the proliferation assays, which were done in triplicate as described in the Examples.
Figure 12:
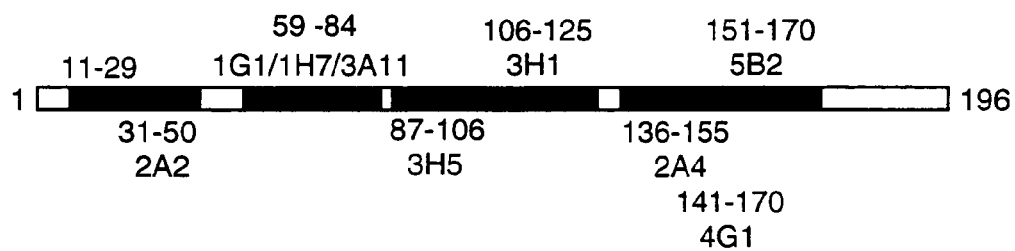
FIG. 12. Diagrammatic representation of location of MBP epitopes of recombinant human MBP 21.5 ("rhMBP21.5"). numbers indicate amino acid residues of SEQ ID NO:1 corresponding to the known epitope specificity of the T cell lines tested (indicated by number letter number designations or "Gimer"). Each of the T cell lines shown gave a positive T cell response to the purified rhMBP21.5 molecules of the invention.

Proliferation assays with two independent exon 2-peptide-specific human T cell lines clearly demonstrated that only synthetic exon 2 peptide, MBP+X2$^{Cys81}$ (FIG. 9) and MBP+X2$^{Ser81}$ (FIG. 10) could elicit a T cell response. In addition, dose response assays (FIG. 10) revealed that both MBP+X2$^{Cys81}$ and MBP+X2$^{Ser81}$ were efficiently displayed to the T cells in vitro. This indicates that Cys$^{81}$ is dispensable for presentation of the exon 2-encoded epitope recognized by the clones tested. T cell proliferation data are also summarized in FIG. 12 and FIG. 13.

These results demonstrate that human T cells can respond to processed X2 epitopes derived from full length MBP 21.5 molecules, and that the bacterially expressed recombinant forms of MBP, including MBP18.5, MBP+X2$^{Cys81}$, and MBP+X2$^{Ser81}$, can be as effective in stimulating encephalitogenic T cells as the native MBP18.5 protein.

Throughout this application various publications and patent disclosures are referred to. The teachings and disclosures thereof, in their entireties, are hereby incorporated by reference into this application to more fully describe the state of the art to which the present invention pertains.

Although preferred and other embodiments of the invention have been described herein, further embodiments may be perceived by those skilled in the art without departing from the scope of the invention as defined by the following claims.

TABLE 1

| amino acid | codon | huMBP 21.5 | recMBP 21.5 | amino acid | codon | huMBP 21.5 | recMBP 21.5 |
|---|---|---|---|---|---|---|---|
| Arg | CGT | 2 | 19 | Ser | TCT | 3 | 7 |
| | CGC | 4 | 1 | | TCC | 7 | 9 |
| | CGA | | | | TCA | 4 | |
| | CGG | 2 | | | TCG | 2 | |
| | AGA | 9 | 1 | | AGT | 2 | |
| | AGG | 4 | | | AGC | 4 | 6 |
| Gly | GGT | 2 | 4 | Ala | GCT | 3 | 3 |
| | GGC | 13 | 24 | | GCC | 5 | 6 |
| | GGA | 10 | | | GCA | 2 | |
| | GGG | 3 | | | GCG | 3 | 4 |
| Lys | AAA | 2 | 14 | Val | GTT | 2 | |
| | AAG | 12 | | | GTC | 2 | |
| Leu | CTT | 2 | | | GTA | 1 | |
| | CTC | 1 | | | GTG | 2 | 5 |
| | CTA | | | His* | CAT | 3 | 6 |
| | CTG | 8 | 10 | | CAC | 8 | 11 |
| | TTA | | | Gln | CAA | 1 | |
| | TTG | | 1 | | CAG | 7 | 8 |
| Pro | CCT | 1 | | Asn | AAT | | |
| | CCC | 5 | | | AAC | 3 | 3 |
| | CCA | 4 | | Asp | GAT | 3 | 3 |
| | CCG | 7 | 17 | | GAC | 6 | 6 |
| Thr | ACT | 1 | | Glu | GAA | 2 | 2 |
| | ACC | 2 | 8 | | GAG | | |
| | ACA | 2 | | Ile | ATT | 2 | 2 |
| | ACG | 3 | | | ATC | 2 | 2 |

TABLE 1-continued

| amino acid | codon | huMBP 21.5 | recMBP 21.5 | amino acid | codon | huMBP 21.5 | recMBP 21.5 |
|---|---|---|---|---|---|---|---|
| Phe | TTT | 4 | | | ATA | | |
| | TTC | 5 | 9 | Tyr | TAT | 2 | 2 |
| Cys | TGT | | | | TAC | 3 | 3 |
| | TGC | 1 | 1 | Trp | TGG | 2 | 2 |
| Met | ATG | 4 | 4 | | | | |

*recMBP21.5 contains six additional Histidines at the C-terminus.

TABLE 2

| GENE | $OD_{600}$ | WET WT (g) | 0.1 N HCL (g/ml) | PEAK HT (cm) | LYSATE VOL (ml) |
|---|---|---|---|---|---|
| MBP + X2$^{Cys81/bact.}$ | 2.70 | 8.0 | 0.080 | 4.3 | 126 |
| MBP + X2$^{Ser81/bact.}$ | 1.89 | 8.8 | 0.088 | 3.6 | 126 |
| MBP18.5$^{hum.}$ | 1.96 | 8.0 | 0.080 | 2.8 | 126 |
| MBP + X2$^{Cys81/hum.}$ | 1.76 | 6.0 | 0.060 | 1.6 | 126 |

REFERENCES

Abbas et. al. 1994. *Cell and Mol Immunology*, pp. 377–391.
Adorini et al. 1993. *Immunol Today* 14, pp. 285–289.
Alderson et al. 1994. *J Exp Med* 181, pp. 71–77
Allegretta et. al. 1990. *Science* 247, pp. 718–722
Boehme and Lenardo 1993. *Eur J Immunol* 23, pp. 1552–1560.
Brown and McFarlin 1981. *Lab Invest* 45, pp. 278–284.
Bruck et al. 1994. *Ann Neurol* 35, pp. 65.
Burns et al. 1989 *J Exp Med* 169, 27.
Chou et al. 1989 *J Neurosci Res* 23, 207.
Chou et al. 1992. *J Neuroimmunol* 38, 105–114.
Cohen et al., 1992. *Ann Rev Immunol* 10, pp. 267.
Cotter et al., 1990. *Anticancer Research* 10, pp. 1153.
Crispe 1994. *Immunity* 1, pp. 347–349
Critchfield et al. 1994. *Science* 263, pp. 1139–1143.
Deibler et al. 1972. *Prep Biochem* 2, pp. 139–165.
Duvall and Wyllie, 1986. *Immunol Today* 7, pp. 115.
Einstein et al. 1962. *J Neurochem* 9, 353.
Endoh et al. 1986. *J of Immunol* 137, pp. 3832–3835.
Evans and Scarpulla, 1989. *Gene* 84, 135.
Fritz et al. 1983. *J of Immunol* 130, pp. 191–194.
Fritz and Zhao. 1994. *J. Neuroimmunol* 51, pp. 1–6.
Greer et al. 1992. *J of Immunol* 149, pp. 783–788.
Grosjean and Fiers, 1982. *Gene* 18, 199.
Hauser 1994. *Harrison's Principles of Int Med*, Thirteenth Ed., pp. 2287–2295.
Hernan et al. 1992 *Biochemistry* 31, 8619.
Ho et al. 1989. *Gene* 77, pp. 51–59.
Huang and Gorman, 1990. *Mol Cell Biol* 10, 1805.
Jayarman et al. 1991. *Proc Natl Acad Sci USA* 88, 4084.
Kalghatgi and Horvath. 1987 *J Chromatogr.* 398, 335.
Kamholtz et al. 1988. *J Neurosci Res* 21, pp. 62–70.
Kaufman et al. 1993. *Nature* 366, 69.
Kawabe and ochi, 1991. *Nature* 349, pp. 245–248.
Kennedy et al. 1990. *J of Immunol* 144, pp. 909–915.
Kerlero de Rosbol et al. 1993. *J Clin Invest.* 92, 2602.
Kerr et al., 1991. *Apoptosis: the molecular basis of cell death*, Tomei and Cope (eds.), Cold Spring Harbor Laboratory Press, Plainview, N.Y., pp. 5.
Kronquist et al. 1987. *J of Neurosci Res* 18, pp. 395–401.
Kuchroo et al. 1992. *J of Immunol* 148, pp. 3776–3782.
Kuchroo et al. 1994. *J of Immunol* 150, pp. 3326–3336.
Lees and Mackin. 1988. *Neuronal and Glial Proteins*. Academic Press, San Diego, pp. 267–298
Lehmann et al. 1992. *Nature* 358, pp. 155–157.
Lenardo 1991. *Nature* 353, pp. 858–860
Linthicum et al. 1982. *Cell Immunol* 73, pp. 299.
Lockshin and Zakeri, 1991. *Apoptosis: the molecular basis of cell death*, Tomei and Cope (eds.), Cold Spring Harbor Laboratory Press, Plainview, N.Y., pp. 47.
Marrack and Kappler, 1987. *Science* 238, pp. 1073.
Martin et al. 1990. *J Immunol* 145, 540.
Martin et al. 1992. *Ann Rev Immunol* 10, pp. 153–187.
Matis et. al. 1983. *Proc Natl Acad Sci USA* 80, pp. 6019–6023
McCarron et al. 1990. *J Neuroimmunol* 29, 73.
McRae et al. 1992. *J of Neuroimmunol* 38, pp. 229–240.
Meinl et al. 1993. *J Clin Invest* 92, 2633.
Miller et al. 1992. *J Neuroimmunol* 39, 243.
Miller and Karpus. 1994. *Immunol Today*, pp. .
Mitchison 1964. *Proc R Soc London Ser B* 161, pp. 275–280.
Morgenstern and Land, 1990. *Nucl Acids Res* 18, 3587.
Oettinger et al. 1993. *J Neuroimmunol* 44, 157.
Ota et al. 1990. *Nature* 346, 183.
Paul, 1989. *Fundamental Immunology*. 2nd Ed. Paul (ed.), Raven Press, New York.
Pette et al. 1990. *Neurology* 40, 1770.
Richert et al. 1989. *J Neuroimmunol* 23, 55.
Smith et al., 1989. *Nature* 337, pp. 181–184.
Pelfry et al. 1993. *J of Neuroimmunol* 46, pp. 33–42.
Pelfry et al. 1994. *J of Neuroimmunol* 53, pp. 153–161.
Prineas et al. 1993. *Ann Neurol* 3 3, pp. 137.
Raine and Wu. 1993. *J Neuropathol Exp Neurol* 52, pp. 199.
Remington's Pharmaceutical Sciences, Mack Publishing Co., Philadelphia, Pa., 17th ed. (1985)
Roth et al. 1987. *J of Neurosci Res* 17, pp. 321–328.
Russell et. al. 1993 *Proc Natl Acad Sci USA* 90, pp. 4409–4413.
Saeki et. al. 1992. *Proc Natl Acad Sci USA* 89, pp. 6157–6161.
Sakai et al. 1989. *Proc Natl Acad Sci* 86, pp. 9470–9474.
Sambrook et al. 1990. *Molecular Cloning: A Laboratory Manual* (Cold Spring Harbor Press, Cold Spring Harbor, N.Y.)
Sato et al. 1994. *J Biol Chem* 269, 17267.
Schwartz, 1993. *Fundamental Immunology*. 3rd Ed. pp. 1033–1083.
Segal et al. 1994. *J of Neuroimmunol* 51, pp. 7–19.
Sercarz et. al. 1959. *Nature* 184, pp. 1080–1082.
Singer et. al. 1994. *Immunity* 1, pp. 365–371.
Sobel et al. 1992. *J of Immunol* 149, pp. 1444–1451.
Sprent 1994. *Cell* 76, pp. 315–322.
Sriram et al. 1983. *Cell Immunol* 75, pp. 378–382.
Studier et al. 1990. *Meth Enzymol* 185, pp. 60–89.

Su and Sriram. 1991. *J of Neuroimmunol* 34, pp. 181–190.
Sun et al. 1991. *Eur J Immunol* 21, pp. 1461–1468.
Tabira. 1988. *Ann NY Acad Sci* 540, pp. 187–201.
Trotter et al. 1987. *J of Neurosci Res* 79, pp. 173–188.
Trotter et al. 1991. *J of Neuroimmunol* 33, pp. 55–62.
Tuohy et al. 1988. *J of Immunol* 141, pp. 1126–1130.
Tuohy et al. 1989. *J of Immunol* 142, pp. 1523–1527.
Tuohy et al. 1992. *J of Neuroimmunol* 39, pp. 67–74.
Van der Venn et al. 1989. *J of Neuroimmunol* 21, pp. 183–191.
Van der Venn et al. 1990. *J of Neuroimmunol* 26, pp. 139–145.
Van der Venn et al. 1992. *J of Neuroimmunol* 38, pp. 139–146.
van Noort et al. 1994. *J Chromatogr B* 653, 155.
von Boehmer, 1988. *Ann Rev Immunol* 6, pp. 309.
Voskuhl et al. 1993a. *J of Neuroimmunol* 42, pp. 187–192.
Voskuhl et al. 1993b. *J of Neuroimmunol* 46, pp. 137–144.
Voskuhl et al. 1994. *J Immunol* 149, 4834.
Wada et al. 1992. *Nucl Acids Res* 20 (Supplement), pp. 2111–2118.
Wauben et al. 1994. *J of Immunol* 150, pp. 4211–4220.
Weimbs and Stoffel. 1992. *Biochemistry* 31, pp. 12289–12296.
Weiner et al. 1993. *Science* 259, 1321.
Whitham et al. 1991. *J of Immunol* 147, pp. 101–107.
Whitham et al. 1991. *J of Immunol* 147, pp. 3803–3808.
Williams et al. 1988. *Nucl Acids Res* 16, 10453.
Wosnick et al. 1987. *Gene* 60, 115.
Yoon, 1993 *Science* 259, 1263.
Zamvil et al. 1986. *Nature* 324, 258.
Zhang et al. 1993. *Science* 261, pp. 1451–1454.
Zhang et al. 1994. *J Exp Med* 179, pp. 973–984.

What is claimed is:

1. A composition comprising (a) an isolated polypeptide comprising amino acid residues 59 to 84 of SEQ ID NO: 1, wherein the amino acid residue at position 81 is a standard amino acid that is not cysteine and (b) a carrier.

2. The composition of claim 1 wherein the amino acid residue at position 81 is serine.

3. An assay comprising:
isolating and partially purifying T cells from a patient,
combining the isolated T cells with an isolated polypeptide comprising amino acid residues 59 to 84 of SEQ ID NO: 1, wherein the amino acid residue at position 81 is a standard amino acid that is not cysteine, and
measuring the level of a T cell response induced by the polypeptide.

4. A kit for the detection of MBP reactive T cells, the kit comprising an isolated polypeptide in close confinement and/or proximity with an agent for use in the detection of a T cell response, wherein said polypeptide comprises amino acid residues 59 to 84 of SEQ ID NO: 1, and wherein the amino acid residue at position 81 is a standard amino acid that is not cysteine.

5. The kit of claim 4 wherein the kit further comprises a label indicating that the kit is for use in the clinical assessment of multiple sclerosis.

6. An isolated polypeptide comprising the amino acid sequence set forth in SEQ ID NO: 1 except that the amino acid residue at position 81 is a standard amino acid other than cysteine.

7. The polypeptide of claim 6, wherein the standard amino acid is an uncharged amino acid having a molecular weight of less than about 150.

8. The polypeptide of claim 7, wherein the standard amino acid is serine.

9. The polypeptide of claim 6, wherein the amino acid at position 81 is selected from the group consisting of alanine, asparagine, glycine, proline, threonine, and serine.

10. The composition of claim 1, wherein the polypeptide comprises the amino acid sequence of SEQ ID NO: 1, wherein the amino acid residue at position 81 is a standard amino acid that is not cysteine.

11. The composition of claim 1, wherein the amino acid at position 81 is selected from the group consisting of alanine, asparagine, glycine, proline, threonine, and serine.

12. The assay of claim 3, wherein the polypeptide comprises the amino acid sequence of SEQ ID NO: 1, wherein the amino acid residue at position 81 is a standard amino acid that is not cysteine.

13. The assay of claim 3, wherein the amino acid at position 81 is selected from the group consisting of alanine, asparagine, glycine, proline, threonine, and serine.

14. The kit of claim 4, wherein the polypeptide comprises the amino acid sequence of SEQ ID NO: 1, wherein the amino acid residue at position 81 is a standard amino acid that is not cysteine.

15. The kit of claim 4, wherein the amino acid at position 81 is selected from the group consisting of alanine, asparagine, glycine, proline, threonine, and serine.

16. An isolated polypeptide comprising a peptide comprising amino acid residues 59 to 84 of SEQ ID NO: 1, wherein the amino acid residue at position 81 is a standard amino acid that is not cysteine.

17. The polypeptide of claim 16 wherein the amino acid residue at position 81 is an uncharged amino acid having a molecular weight of less than about 150.

18. The polypeptide of claim 16 wherein the amino acid residue at position 81 is serine.

19. The polypeptide of claim 16, wherein the amino acid at position 81 is selected from the group consisting of alanine, asparagine, glycine, proline, threonine, and serine.

* * * * *